(12) United States Patent
Emerson et al.

(10) Patent No.: US 11,254,980 B1
(45) Date of Patent: Feb. 22, 2022

(54) METHODS OF PROFILING TARGETED POLYNUCLEOTIDES WHILE MITIGATING SEQUENCING DEPTH REQUIREMENTS

(71) Applicant: Adaptive Biotechnologies Corp., Seattle, WA (US)

(72) Inventors: Ryan O. Emerson, Seattle, WA (US); Anna M. Sherwood, Seattle, WA (US); Harlan S. Robins, Seattle, WA (US)

(73) Assignee: Adaptive Biotechnologies Corporation, Seattle, WA (US)

( * ) Notice: Subject to any disclaimer, the term of this patent is extended or adjusted under 35 U.S.C. 154(b) by 394 days.

(21) Appl. No.: 16/197,629

(22) Filed: Nov. 21, 2018

Related U.S. Application Data

(60) Provisional application No. 62/592,022, filed on Nov. 29, 2017.

(51) Int. Cl.
*C12Q 1/6869* (2018.01)
*C12Q 1/6806* (2018.01)
*C12Q 1/6851* (2018.01)
*C12Q 1/686* (2018.01)

(52) U.S. Cl.
CPC ......... *C12Q 1/6869* (2013.01); *C12Q 1/6806* (2013.01); *C12Q 1/686* (2013.01); *C12Q 1/6851* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,189,147 A | 2/1993 | Saito et al. |
| 5,213,960 A | 5/1993 | Chang |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,418,134 A | 5/1995 | Morley |
| 5,506,126 A | 4/1996 | Seed et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,925,517 A | 7/1999 | Tyagi et al. |
| 5,935,793 A | 8/1999 | Wong |
| 5,981,176 A | 11/1999 | Wallace |
| 6,087,096 A | 7/2000 | Dau et al. |
| 6,091,000 A | 7/2000 | Haynes |
| 6,136,566 A | 10/2000 | Sands et al. |
| 6,172,214 B1 | 1/2001 | Brenner |
| 6,207,371 B1 | 3/2001 | Zambrowicz et al. |
| 6,214,613 B1 | 4/2001 | Higuchi et al. |
| 6,228,589 B1 | 5/2001 | Brenner |
| 6,255,071 B1 | 7/2001 | Beach et al. |
| 6,258,568 B1 | 7/2001 | Nyren |
| 6,291,183 B1 | 9/2001 | Pirrung et al. |
| 6,300,065 B1 | 10/2001 | Kieke et al. |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,423,538 B1 | 7/2002 | Wittrup et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,753,147 B2 | 6/2004 | Vogelstein et al. |
| 6,787,308 B2 | 9/2004 | Balasubramanian et al. |
| 6,919,434 B1 | 7/2005 | Goto et al. |
| 6,964,850 B2 | 11/2005 | Bevilacqua |
| 6,969,597 B2 | 11/2005 | Lukyanov et al. |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

US 6,331,391 B1, 12/2001, Wittrup et al. (withdrawn)
US 8,642,750, 2/2014, Faham et al. (withdrawn).
Abbott, et al. "Design and use of signature primers to detect carry-over of amplified material", *J Virol Methods*, 46(1):51-59, Abstract Only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).
Aird, et al., "Analyzing and minimizing PCR amplification bias in Illumina sequencing libraries." Genome Biology (2011); 12: R18, pp. 1-14.

(Continued)

*Primary Examiner* — Samuel C Woolwine
*Assistant Examiner* — Carolyn L Greene
(74) *Attorney, Agent, or Firm* — Shweta Chandra; Edward J. Baba; Bozicevic, Field & Francis LLP

(57) ABSTRACT

Methods and compositions are provided for quantifying the number of biological input molecules of one or more target genes of interest in a PCR. The method comprises steps for amplifying multiple synthetic templates and high throughput sequencing. The method further comprises steps for achieving equal sequencing coverage between targets that do not occur in equal ratios, while mitigating the need for costly deep sequencing methods.

22 Claims, 5 Drawing Sheets

Specification includes a Sequence Listing.

(56) References Cited

U.S. PATENT DOCUMENTS

| | | |
|---|---|---|
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,323,306 B2 | 1/2008 | Dunn et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,709,197 B2 | 5/2010 | Drmanac |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,955,794 B2 | 6/2011 | Shen et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,685,898 B2 | 4/2014 | Wiley |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 | 1/2016 | Faham et al. |
| 9,279,159 B2 | 3/2016 | Robins et al. |
| 9,290,811 B2 | 3/2016 | Quake et al. |
| 9,371,558 B2 | 6/2016 | Robins et al. |
| 9,394,567 B2 | 7/2016 | Asbury et al. |
| 9,416,420 B2 | 8/2016 | Faham et al. |
| 9,506,119 B2 | 11/2016 | Faham et al. |
| 9,512,487 B2 | 12/2016 | Faham et al. |
| 9,708,657 B2 | 7/2017 | Asbury et al. |
| 9,809,813 B2 | 11/2017 | Robins et al. |
| 10,066,265 B2 | 9/2018 | Klinger et al. |
| 10,077,473 B2 | 9/2018 | Asbury et al. |
| 10,077,478 B2 | 9/2018 | Faham et al. |
| 10,150,996 B2 | 12/2018 | Robins et al. |
| 10,155,992 B2 | 12/2018 | Faham et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0018489 A1 | 1/2004 | Ma et al. |
| 2004/0033490 A1 | 2/2004 | Laird et al. |
| 2004/0121364 A1 | 6/2004 | Chee et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0275752 A1 | 7/2006 | Sindhi |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0233802 A1 | 9/2009 | Bignell et al. |
| 2009/0253581 A1 | 10/2009 | Van Eijk et al. |

(56) References Cited

U.S. PATENT DOCUMENTS

| | | |
|---|---|---|
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0129874 A1 | 5/2010 | Mitra et al. |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0323355 A1 | 12/2010 | Dittmer |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0166034 A1 | 7/2011 | Kwong et al. |
| 2011/0183863 A1 | 7/2011 | Wagner et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0010096 A1 | 1/2012 | Wohlgemuth et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2012/0308999 A1 | 12/2012 | Sarma et al. |
| 2013/0005584 A1 | 1/2013 | Faham |
| 2013/0017957 A1 | 1/2013 | Faham et al. |
| 2013/0045221 A1 | 2/2013 | Stauss et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0137108 A1 | 5/2013 | Tripathi et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0273647 A1 | 10/2013 | Sahin et al. |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0065629 A1 | 3/2014 | Barken et al. |
| 2014/0094376 A1 | 4/2014 | Han |
| 2014/0127699 A1 | 5/2014 | Han |
| 2014/0141982 A1 | 5/2014 | Jacobson et al. |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0227705 A1 | 8/2014 | Vogelstein et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017630 A1 | 1/2015 | Oved et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0087535 A1 | 3/2015 | Patel et al. |
| 2015/0133317 A1 | 5/2015 | Robinson et al. |
| 2015/0154352 A1 | 6/2015 | Johnson et al. |
| 2015/0167080 A1 | 6/2015 | Moorhead et al. |
| 2015/0203897 A1 | 7/2015 | Robins et al. |
| 2015/0215062 A1 | 7/2015 | Li et al. |
| 2015/0218656 A1 | 8/2015 | Kirsch et al. |
| 2015/0232936 A1 | 8/2015 | Shoemaker et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |
| 2015/0299785 A1 | 10/2015 | Livingston et al. |
| 2015/0299786 A1 | 10/2015 | Robins et al. |
| 2015/0299800 A1 | 10/2015 | Faham et al. |
| 2016/0024493 A1 | 1/2016 | Robins et al. |
| 2016/0115532 A1 | 4/2016 | Faham |
| 2016/0138011 A1 | 5/2016 | Dewitt et al. |
| 2016/0186260 A1 | 6/2016 | Klinger et al. |
| 2016/0201133 A1 | 7/2016 | Faham et al. |
| 2016/0251721 A1 | 9/2016 | Robins et al. |
| 2016/0251728 A1 | 9/2016 | Faham et al. |
| 2016/0258025 A1 | 9/2016 | Klinger et al. |
| 2016/0304956 A1 | 10/2016 | Robins et al. |
| 2016/0319340 A1 | 11/2016 | Robins et al. |
| 2017/0037469 A1 | 2/2017 | Robins et al. |
| 2017/0292149 A1 | 10/2017 | Emerson et al. |
| 2017/0335386 A1 | 11/2017 | Livingston et al. |
| 2017/0335390 A1 | 11/2017 | Asbury et al. |
| 2017/0335391 A1 | 11/2017 | Emerson et al. |
| 2017/0349954 A1 | 12/2017 | Faham et al. |
| 2018/0023143 A9 | 1/2018 | Faham et al. |
| 2018/0037953 A1 | 2/2018 | Emerson et al. |
| 2018/0073015 A1 | 3/2018 | Robins et al. |
| 2018/0080090 A1 | 3/2018 | Faham et al. |
| 2018/0087109 A1 | 3/2018 | Klinger et al. |
| 2018/0112278 A1 | 4/2018 | Faham et al. |

(56) References Cited

U.S. PATENT DOCUMENTS

| | | |
|---|---|---|
| 2018/0312832 A1 | 11/2018 | Robins et al. |
| 2018/0355429 A1 | 12/2018 | Klinger et al. |

FOREIGN PATENT DOCUMENTS

| | | |
|---|---|---|
| CN | 103097888 A | 5/2013 |
| EA | 007958 B1 | 2/2007 |
| EP | 0303459 A2 | 2/1989 |
| EP | 0799897 A1 | 10/1997 |
| EP | 1516929 A2 | 3/2005 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088205 A1 | 8/2009 |
| EP | 2088432 A1 | 8/2009 |
| EP | 2418287 A2 | 2/2012 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2011-505123 A | 2/2011 |
| JP | 2012-508011 A | 4/2012 |
| JP | 2013-524848 A | 6/2013 |
| JP | 2013-524849 A | 6/2013 |
| WO | WO 1993/001838 A1 | 2/1993 |
| WO | WO 1995/028481 A1 | 10/1995 |
| WO | WO 1997/013868 A1 | 4/1997 |
| WO | WO 1997/013877 A1 | 4/1997 |
| WO | WO 1997/018330 A1 | 5/1997 |
| WO | WO 1997/046706 A1 | 12/1997 |
| WO | WO 1998/001738 A2 | 1/1998 |
| WO | WO 1998/044151 A1 | 10/1998 |
| WO | WO 1999/019717 A1 | 4/1999 |
| WO | WO 1999/020798 A1 | 4/1999 |
| WO | WO 2001/014424 A2 | 3/2001 |
| WO | WO 2002/024322 A2 | 3/2002 |
| WO | WO 2003/008624 A2 | 1/2003 |
| WO | WO 2003/044225 A2 | 5/2003 |
| WO | WO 2003/052101 A1 | 6/2003 |
| WO | WO 2003/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/003375 A2 | 1/2005 |
| WO | WO 2005/005651 A2 | 1/2005 |
| WO | WO 2005/010200 A2 | 2/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/008759 A2 | 1/2007 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/152928 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/083456 A1 | 7/2010 |
| WO | WO 2010/151416 A1 | 12/2010 |
| WO | WO 2011/017151 A2 | 2/2011 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/012703 A2 | 1/2012 |
| WO | WO 2012/017081 A1 | 2/2012 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/122484 A1 | 9/2012 |
| WO | WO 2012/142213 A2 | 10/2012 |
| WO | WO 2012/148497 A2 | 11/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/123442 A1 | 8/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2014/145992 A1 | 9/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2015/134787 A2 | 9/2015 |
| WO | WO 2015/153788 A1 | 10/2015 |
| WO | WO 2015/160439 A2 | 10/2015 |
| WO | WO 2016/069886 A1 | 5/2016 |

(56) References Cited

FOREIGN PATENT DOCUMENTS

| WO | WO 2016/138122 A1 | 9/2016 |
|---|---|---|
| WO | WO 2016/161273 A1 | 10/2016 |

OTHER PUBLICATIONS

Akamatsu, Y. et al., "Essential Residues in V(D)J Recombination Signals." The Journal of Immunology (1994); 153 (10): 4520-4529.
Akatsuka, Y. et al., "Rapid screening of T-cell receptor (TOR) variable gene usage by multiplex PCR: Application for assessment of clonal composition", Tissue Antigens, 53(2):122-134 (1999).
Alatrakchi et al. "T-cell clonal expansion in patients with B-cell lymphoproliferative disorders", Journal of Immunotherapy, 21(5):363-370 (1998).
Alexandre, D. et al. "H. sapiens rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.
Alexandre, D. et al. "H. sapiens rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Altman, et al. "Phenotypic analysis of antigen-specific T lymphocytes", The Journal of Immunology, 187(1):7-9 (2011).
Andreasson, et al. "The human IgE-encoding transcriptome to assess antibody repertoires and repertoire evolution", J Mol Biol., 362(2):212-227 (2006). Epub Aug. 14, 2006.
Armand, P. et al., "Detection of circulating tumour DNA in patients with aggressive B-cell non-Hodgkin lymphoma", Brit. J. Haematol., vol. 163, pp. 123-126 (2013).
Arstila, T.P., et al., "A direct estimate of the human αβ T cell receptor diversity," Science, 286(5441): 958-961 (1999).
Aslanzadeh. "Preventing PCR amplification carryover contamination in a clinical laboratory", Ann Clin Lab Sci., 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", Blood, 96(2): 640-646 (2000).
Attaf, et al., "αβ T cell receptors as predictors of health and disease." Cellular & Molecular Immunology (Jul. 2015); 12 (4): 391-399. Epub Jan. 26, 2015.
Babrzadeh et al. "Development on High-throughput Sequencing Technology: emPCR Titration and Barcode Design", Stanford School of Medicine, 2 pages (2011).
Bagnara, et al. "IgV gene intraclonal diversification and clonal evolution in B-cell chronic lymphocytic leukaemia", British Journal of Haematology, 133(1):50-58 (2006).
Barbas III, et al., "Assembly of combinatorial antibody libraries on phage surfaces: the gene III site." Proc Natl Acad Sci U S A. (Sep. 1991); 88(18): 7978-7982.
Barker, et al. "A second type II restriction endonuclease from Thermus aquaticus with an unusual sequence specificity", Nucleic Acids Res., 12(14): 5567-5581 (1984).
Barnard, et al., "PCR Bias Toward the Wild-Type k-rasand p53 Sequences: Implications for PCR Detection of Mutations and Cancer Diagnosis." BioTechniques (Oct. 1998); 25: 684-691.
Baum and McCune et al. "Direct measurement of T-cell receptor repertoire diversity with AmpliCot", Nat Methods, 3(11): 895-901 (2006).
Becton-Dickinson T-Cell Research Tools, "Novel multicolor flow cytometry tools for the study of CD4+ T-cell differentiation and plasticity", 16 pages (2009).
Becton-Dickinson, CD marker handbook, bdbiosciences.com/go/mousecdmarkers, p. 1-47 (2010).
Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", Blood, 83(8):2238-2247 (1994).
Béné and Kaeda, "How and why minimal residual disease studies are necessary in leukemia: a review from WP10 and WP12 of the European LeukaemiaNet", Haematologica, 94(8):1135-1150 (2009).
Benichou, J. et al., "The restricted DH gene reading frame usage in the expressed human antibody repertoire is selected based upon its amino acid content", J Immunol., 190(11): 5567-77, 29 pages (2013).
Benichou, J et al., "Rep-Seq: uncovering the immunological repertoire through next-generation sequencing", Immunology, 135(3): 183-191 (2011).
Berger, et al. "The clonotypic T cell receptor is a source of tumor-associated antigens in cutaneous T cell lymphoma", Annals of the New York Academy of Sciences, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.
Bernard et al. "Color multiplexing hybridization probes using the apolipoprotein E locus as a model system for genotyping", Anal Biochem., 273(2):221-228 (1999).
Bernardin, F. et al., "Estimate of the total number of CD8+ clonal expansions in healthy adults using a new DNA heteroduplex-tracking assay for CDR3 repertoire analysis", Journal of Immunological Methods, 274(I-2):159-175 (2003).
Bertness, et al. "T-Cell Receptor Gene Rearrangements as Clinical Markers of Human T-Cell Lymphomas", The New England Journal of Medicine, 313:534-538 (1985).
Bessette, et al., "Rapid isolation of high-affinity protein binding peptides using bacterial display." Protein Engineering, Design and Selection (Oct. 2004); 17(10): 731-739.
Bhatia, et al., "Rolling Adhesion Kinematics of Yeast Engineered to Express Selectins." Biotechnology Progress (2003); 19(3): 1033-1037.
Bidwell, "Advances in DNA-based HLA-typing methods." Immunol Today (Jul. 1994); 15 (7): 303-307.
Biggerstaff, et al. "Enumeration of leukocyte infiltration in solid tumors by confocal laser scanning microscopy", BMC Immunol., 7:16, 13 pages (2006).
Boder and Wittrup, "Yeast surface display for screening combinatorial polypeptide libraries." Nat Biotechnol. (Jun. 1997); 15(6): 553-557.
Bolotin, D.A. et al., "Next generation sequencing for TCR repertoire profiling: Platform-specific features and correction algorithms", Eur. J. Immunol., 42:3073-3083 (2012).
Bonarius, H.P.J. et al. "Monitoring the T-Cell Receptor Repertoire at Single-Clone Resolution", PLOS One, 1(e55):1-10 (2006).
Bonilla, F.A. et al., "Adaptive Immunity." J. Allergy Clin. Immunol. (2010); 125: S33-S40.
Boria, et al. "Primer sets for cloning the human repertoire of T cell receptor variable regions", BMC Immunology, 9:50, 9 pages (2008).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", Molecular Immunology, 45: 2437-2445 (2008).
Boulware and Daugherty, "Protease specificity determination by using cellular libraries of peptide substrates (CLiPS)." PNAS (May 2006); 103 (20): 7583-7588.
Boyce, et al. "Human regulatory T-cell isolation and measurement of function", BD Biosciences, pp. 1-20 (2010).
Boyd, S.D. et al., "Individual Variation in the Germline Ig Gene Repertoire Inferred from Variable Region Gene Rearrangements", The Journal of Immunology, 184(12): 6986-6992 (2010). Epub 2010.

(56) References Cited

OTHER PUBLICATIONS

Boyd, S.D. et al., "Measurement and Clinical Monitoring of Human Lymphocyte Clonality by Massively Parallel V-D-J Pyrosequencing," *Science Translational Medicine*, 1:12ra23, 40 pages, including Supplementary Materials (2009).
Bradbury, et al., "Use of Living Columns to Select Specific Phage Antibodies." BioTechnology (1993); 11: 1565-1568.
Bradfield, et al. "Graft-versus-leukemia effect in acute lymphoblastic leukemia: the importance of tumor burden and early detection", Leukemia, 18(6): 1156-1158 (2004).
Brehm-Stecher and Johnson. "Single-cell microbiology: tools, technologies, and applications", *Microbiology and Molecular Biology Reviews*, 68(3):538-559 (2004).
Brenan, C. et al., "High throughput, nanoliter quantitative PCR," *Drug Discovery Today: Technologies*, 2(3):247-253 (2005).
Brennan et al. "Predictable αβ T-cell receptor selection toward an HLA-B*3501- restricted human cytomegalovirus epitope", J. Virol., 81(13): 7269-7273 (2007).
Brisco, et al. "Determining the repertoire of IGH gene rearrangements to develop molecular markers for minimal residual disease in B-lineage acute lymphoblastic leukemia", *J Mol Diagn.*, 11(3):194-200 (2009).
Brisco, et al. "Outcome prediction in childhood acute lymphoblastic leukaemia by molecular quantification of residual disease at the end of induction", Lancet, 343:196-200 (1994).
Brochet et al. "IMGT/V-QUEST: the highly customized and integrated system for IG and TR standardized V-J and V-D-J sequence analysis", *Nucleic Acids Research*, vol. 36, Web Server issue W503-W508 (2008).
Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.
Brody, et al., "Immunotransplant for mantle cell lymphoma: Phase I/II study preliminary results", *Journal of Clinical Oncology*, ASCO Annual Meeting Abstracts Part 1, Suppl; abstr 2509: vol. 29, No. 15, 1 page (2011).
Brüggemann, et al. "Clinical significance of minimal residual disease quantification in adult patients with standard-risk acute lymphoblastic leukemia", *Blood*, 107(3):1116-1123 (2006). Epub Sep. 29, 2005.
Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).
Brüggemann, et al. "Standardized MRD quantification in European ALL trials: proceedings of the Second International Symposium on MRD assessment in Kiel, Germany, Sep. 18-20, 2008", *Leukemia*, 24(3):521-535 (2010). doi: 10.1038/leu.2009.268. Epub Dec. 24, 2009.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Bupp and Roth, "Altering retroviral tropism using a random-display envelope library." Mol Ther. (Mar. 2002); 5(3): 329-335.
Butkus, B. "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.
Bystrykh. "Generalized DNA Barcode Design Based on Hamming Codes", *PLoS ONE*, 7(5): e36852, 1-8 (2012).
Campana, et al. "Role of minimal residual disease monitoring in adult and pediatric acute lymphoblastic leukemia", *Hematol Oncol Clin North Am.*, 23(5): 1083-1098 (2009). doi: 10.1016/j.hoc.2009. 07.010.
Campana. "Minimal residual disease in acute lymphoblastic leukemia", *Semin Hematol.*,46(1): 100-106 (2009).

Campbell et al. "Subclonal phylogenetic structures in cancer revealed by ultra-deep sequencing," *PNAS*, 105(35):13081-13086 (2008).
Caporaso, J.G. et al. "Global patterns of 16S rRNA diversity at a depth of millions of sequences per sample", *PNAS*, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", *Blood*, 113(15): 3553-3557 (2009). doi: 10.1182/blood-2008-08-174839. Epub Feb. 6, 2009.
Carlson et al. "Profiling the repertoire of TCRB usage in induced and natural Treg cells", *The Journal of Immunology*, 186: 62.5, Abstract (2011).
Carlson, C.S. et al. "Using synthetic templates to design an unbiased multiplex PCR assay", *Nature Communications*, 4:2680, pp. 1-9 (2013).
Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.
Casali, et al. "Human monoclonals from antigen-specific selection of B lymphocytes and transformation by EBV", *Science*, 234(4775): 476-479, Abstract Only (1986).
Casbon et al. "A method for counting PCR template molecules with application to next-generation sequencing", *Nucleic Acids Research*, 39(12): e81, 8 pages (2011).
Catherwood, M.A. et al., "Improved clonality assessment in germinal centre/post germinal centre non-Hodgkin's lymphomas with high rates of somatic hypermutation", *J. Clin. Pathol.*, 60:524-528, Abstract (2007).
Cha et al., "Improved Survival with T Cell Clonotype Stability After Anti-CTLA-4 Treatment in Cancer Patients." Sci Transl Med (2014); 6(238): 238ra70.
Chan et al. "Evaluation of Nanofluidics Technology for High-Throughput SNP Genotyping in a Clinical Setting", *The Journal of Molecular Diagnostics*, 13(3): 305-312 (2011).
Charbit, et al., "Versatility of a vector for expressing foreign polypeptides at the surface of Gram-negative bacteria." Gene (1988); 70(1): 181-189.
Chen et al. "A novel approach for the analysis of T-cell reconstitution by using a T-cell receptor β-based oligonucleotide microarray in hematopoietic stem cell transplantation", *Exp Hematol.*, 35(5):831-841 (2007).
Chen, et al. "Microfluidic cell sorter with integrated piezoelectric actuator", *Biomed Microdevices*, 11(6): 1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).
Chestnut, et al., "Selective isolation of transiently transfected cells from a mammalian cell population with vectors expressing a membrane anchored single-chain antibody." J Immunol Methods. (Jun. 1996);193(1): 17-27.
Chinese Application No. 201380042163.X, Search Report dated Apr. 12, 2016 (English translation), 2 pages.
Chinese Patent Application No. 2014800254909, Search Report and English translation, dated May 25, 2017, dated by the Chinese Patent Office on Jun. 6, 2017, 5 pages.
Chinese Patent Application No. 201510054401.X, Search Report dated Jul. 14, 2016, 2 pages.
Chiu, et al. "Non-invasive prenatal assessment of trisomy 21 by multiplexed maternal plasma DNA sequencing: large scale validity study", *BMJ*, 342:c7401, 9 pages (2011). doi: 10.1136/bmj.c7401.
Choi, et al. "Clonal evolution in B-lineage acute lymphoblastic leukemia by contemporaneous $V_H$-$V_H$ gene replacements and $V_H$-$DJ_H$ gene rearrangements", *Blood*, 87(6):2506-2512 (1996).
Choi, et al. "Relapse in children with acute lymphoblastic leukemia involving selection of a preexisting drug-resistant subclone", *Blood*, 110(2):632-639 (2007).
Chothia, C. et al. "Canonical structures for the hypervariable regions of immunoglobulins," *J. Mol. Biol.*, 196:901-917, Abstract only (1987).

(56) References Cited

OTHER PUBLICATIONS

Chothia, C. et al. "Conformations of immunoglobulin hypervariable regions," *Nature*, 342:877-883 (1989).
Chou, et al., "Expression of Chimeric Monomer and Dimer Proteins on the Plasma Membrane of Mammalian Cells." Biotechnol Bioeng (Oct. 1999); 65(2): 160-169.
Churchill and Waterman. "The Accuracy of DNA Sequences: Estimating Sequence Quality", *Genomics*, 14:89-98 (1992).
Chute, et al. "Detection of immunoglobulin heavy chain gene rearrangements in classic Hodgkin lymphoma using commercially available BIOMED-2 primers", *Diagn Mol Pathol.*, 17(2): 65-72 (2008).
Citri et al. "Comprehensive qPCR profiling of gene expression in single neuronal cells", *Nature Protocols*, 7(1): 118-127 (2012).
Cleary, et al. "Production of complex nucleic acid libraries using highly parallel in situ oligonucleotide synthesis", *Nat Methods*, 1(3): 241-248 (2004). Epub Nov. 18, 2004.
Clemente, et al. "Deep sequencing of the T -cell receptor repertoire in CD8+ T -large granular lymphocyte leukemia identifies signature landscapes", Blood, 122(25): 4077-85 (2013). doi: 10.1182/blood-2013-05-506386. Epub Oct. 22, 2013.
Craig et al. "Identification of genetic variants using bar-coded multiplex sequencing", *Nature Methods*, 5(10): 887-893 (2008) and Supplemental Materials.
Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.
Cronn et al. "Multiplex sequencing of plant chloroplast genomes using Solexa sequencing-by-synthesis technology", *Nucleic Acids Research*, 36(19):e122, 1-11 (2008).
Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", *The Journal of Immunology*, 172:1935-1944 (2004).
Curran-Everett, D., "Multiple comparisons: philosophies and illustrations", *Am J Physiol Regulatory Integrative Comp Physiol.*, 279:R1-R8 (2000).
Currier and Robinson. "Spectratype/immunoscope analysis of the expressed TCR repertoire", *Current Protocols in Immunology*, Supplement 38:10.28.1-10.28.24 (2000).
Dane, et al., "Isolation of cell specific peptide ligands using fluorescent bacterial display libraries." J Immunol Methods. (Feb. 2006); 309(1-2): 120-129. Epub Jan. 11, 2006.
Dash, P. et al., "Paired analysis of TCR[alpha] and TCR[beta] chains at the single-cell level in mice", *Journal of Clinical Investigation*, 121(1):288-295 (2011).
Daugherty, et al., "Quantitative analysis of the effect of the mutation frequency on the affinity maturation of single chain Fv antibodies." PNAS (Feb. 2000); 97 (5): 2029-2034.
Davi, et al. "Lymphocytic progenitor cell origin and clonal evolution of human B-lineage acute lymphoblastic leukemia", *Blood*, 88(2):609-621 (1996).
Davis, et al. "Interrogating the repertoire: broadening the scope of peptide-MHC multimer analysis", *Nat Rev Immunol.*, 11(8):551-558 (2011). doi: 10.1038/nri3020.
Davis, et al. "Staining of cell surface human CD4 with 2'-F-pyrimidine-containing RNA aptamers for flow cytometry", *Nucleic Acids Research*, 26(17):3915-3924 (1998).
Day, et al., "Identification of non-amplifying CYP21 genes when using PCR-based diagnosis of 21-hydroxylase deficiency in congenital adrenal hyperplasia (CAH) affected pedigrees." Hum Mol Genet. (Dec. 1996); 5(12): 2039-2048.
De Cárcer, et al. "Strategy for Modular Tagged High-Throughput Amplicon Sequencing." Applied and Environmental Microbiology (Sep. 2011); 77(17): 6310-6312.

Dean, et al. "Rapid amplification of plasmid and phage DNA using Phi 29 DNA polymerase and multiply-primed rolling circle amplification", *Genome Res.*, 11(6): 1095-1099 (2001).
Dedhia, et al. "Evaluation of DNA extraction methods and real time PCR optimization on formalin-fixed paraffin-embedded tissues", *Asian Pac J Cancer Prev.*, 8(1): 55-59 (2007).
Dekosky et al. "High-throughput sequencing of the paired human immunoglobulin heavy and light chain repertoire", *Nature Biotechnology*, 31(2): 166-169 (2013).
Deng et al. "Gene profiling involved in immature CD4+ T lymphocyte responsible for systemic lupus erythematosus", *Molecular Immunology*, 43:1497-1507 (2006).
Deschoolmeester, et al. "Tumor infiltrating lymphocytes: an intriguing player in the survival of colorectal cancer patients", *BMC Immunology*, 11:19, 12 pages (2010).
Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).
Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.
DeWitt, et al., "Dynamics of the Cytotoxic T Cell Response to a Model of Acute Viral Infection." J. Virol. (Apr. 2015); 89 (8): 4517-4526. Epub Feb. 4, 2015.
Dictor et al. "Resolving T-cell receptor clonality in two and genotype in four multiplex polymerase chain reactions", *Haematologica*, 90(11): 1524-1532 (2005).
Diederichsen, et al. "Prognostic value of the CD4+/CD8+ ratio of tumour infiltrating lymphocytes in colorectal cancer and HLA-DR expression on tumour cells", *Cancer Immunol Immunother.*, 52(7):423-428 (2003). Epub Apr. 1, 20035.
Diehl, et al. "BEAMing: single-molecule PCR on microparticles in water-in-oil emulsions", *Nat Methods*, 3(7):551-559, Abstract Only (2006).
Ding, et al. "Clonal evolution in relapsed acute myeloid leukaemia revealed by whole-genome sequencing", *Nature*, 481(7382):506-510 (2012).
Diviacco, et al. "A novel procedure for quantitative polymerase chain reaction by coamplification of competitive templates", *Gene*, 122(2):313-320 (1992).
Dobosy, J. et al. "RNase H-dependent PCR (rhPCR): improved specificity and single nucleotide polymorphism detection using blocked cleavable primers", *BMC Biotechnology*, 11(80):1-18 (2011).
Dohm, et al. "Substantial biases in ultra-short read data sets from high throughput DNA sequencing", *Nucleic Acids Research*, 36:e105, 10 pages (2008).
Dou, et al. "Analysis of T cell receptor $V_\beta$ gene usage during the course of disease in patients with chronic hepatitis B", *Journal of Biomedical Science*, 5(6):428-434 (1998).
Dressman, et al. "Transforming single DNA molecules into fluorescent magnetic particles for detection and enumeration of genetic variations", PNAS, 100(15):8817-8822 (2003). Epub Jul. 11, 2003.
Drmanac, et al. "Human genome sequencing using unchained base reads on self-assembling DNA nanoarrays", *Science*, 327(5961):78-81 (2010). Epub Nov. 5, 2009.
Droege, et al. "The Genome Sequencer FLX System—longer reads, more applications, straight forward bioinformatics and more complete data sets", *J Biotechnol.*, 136(1-2):3-10 (2008). doi: 10.1016/j.jbiotec.2008.03.021. Epub Jun. 21, 2008.
Droese, J., et al. "Validation of BIOMED-2 multiplex PCR tubes for detection of TCRB gene rearrangements in T-cell malignancies," *Leukemia*, 18:1531-1538 (2004).
Du et al. "TCR spectratyping revealed T lymphocytes associated with graft-versus-host disease after allogeneic hematopoietic stem cell transplantation", *Leukemia & Lymphoma*, 48(8):1618-1627 (2007).
Dueñas, M., et al. "In vitro immunization of naive human B cells yields high affinity immunoglobulin G antibodies as illustrated by phage display." Immunology (1996); 89.1: 1-7.

(56) References Cited

OTHER PUBLICATIONS

Dunn, et al. "Focus on TILs: Prognostic significance of tumor infiltrating lymphocytes in human glioma", *Cancer Immun.*, 7:12, 16 pages (2007).

Dziubianau, M., et al., "TCR repertoire analysis by next generation sequencing allows complex differential diagnosis of T cell-related pathology." Am J Transplant (Nov. 2013); 13(11): 2842-2854. doi: 10.1111/ajt.12431. Epub Sep. 10, 2013.

Eason et al. "Characterization of synthetic DNA bar codes in *Saccharomyces cerevisiae* gene-deletion strains," PNAS, 101(30): 11046-11051 (2004).

Edd et al. "Controlled encapsulation of single cells into monodisperse picoliter drops", *Lab Chip*, 8(8): 1262-1264 (2008).

Efron and Thisted, "Estimating the number of unseen species: How many words did Shakespeare know?" Biometrika (1976); 63(3): 435-447.

Eichler, et al. "Haplotype and interspersion analysis of the FMR1 CGG repeat identifies two different mutational pathways for the origin of the fragile X syndrome", *Hum Mol Genet.*, 5(3):319-330 (1996).

Eichler, et al. "Length of uninterrupted CGG repeats determines instability in the FMR1 gene", *Nat Genet.*, 8(1):88-94, Abstract Only (1994).

Eid et al. "Real-time DNA sequencing from single polymerase molecules", *Science*, 323(5910): 133-138 (2009). Epub Nov. 20, 2008.

Eis, et al. "An invasive cleavage assay for direct quantitation of specific RNAs", *Nat Biotechnol.*, 19(7):673-676, Abstract Only (2001).

Eisenstein. "Personalized, sequencing-based immune profiling spurs startups", Nat Biotechnol., 31(3):184-186 (2013). doi: 10.1038/nbt0313-184b.

Elkord et al. "T regulatory cells in cancer: recent advances and therapeutic potential", *Expert Opinion on Biological Therapy*, 10(11): 1573-1586 (2010).

Emerson et al. "Defining the Alloreactive T Cell Repertoire Using High-Throughput Sequencing of Mixed Lymphocyte Reaction Culture", *PLoS One*, 9(11): e111943 (2014).

Emerson, et al. "CD4+ and CD8+ T cell β antigen receptors have different and predictable V and J gene usage and CDR3 lengths", Presented at the Annual Meeting of The American Association of Immunologists 2012 in Boston, MA May 2012. Poster.

Emerson, et al. "Correlation of TCR diversity with immune reconstitution after cord blood transplant", Presented at the American Society of Clinical Oncology's annual meeting. May 2012. Poster. 1 page.

Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.

Emerson, et al., "De novo detection and HLA-association of public T cell responses to Cytomegalovirus using high-throughput immune repertoire sequencing (VIR1P.1134)." The Journal of Immunology (May 2015); 194 (1 Supplement): 74.1, Abstract.

Emerson, et al., "Immunosequencing identifies signatures of cytomegalovirus exposure history and HLA-mediated effects on the T cell repertoire." Nature Genetics (May 2017); 49 (3): 659-665. Epub Apr. 3, 2017.

Emerson, R.O. et al. "High-throughput sequencing of T-cell receptors reveals a homogeneous repertoire of tumour-infiltrating lymphocytes in ovarian cancer", *Journal of Pathology*, 231: 433-440 (2013).

Esendagli et al. "Malignant and non-malignant lung tissue areas are differentially populated by natural killer cells and regulatory T cells in non-small cell lung cancer", *Lung Cancer*, 59(1): 32-40 (2008).

Estorninho, et al. "A novel approach to tracking antigen-experienced CD4 T cells into functional compartments via tandem deep and shallow TCR clonotyping", J Immunol., 191(11): 5430-5440 (2013). doi: 10.4049/jimmunol.1300622. Epub Oct. 25, 2013.

European Application No. 09764927.1, European Opposition dated Oct. 15, 2014 (in French only).

European Application No. 09764927.1, Notice of Opposition dated Oct. 14, 2014, Reference# 547-7.

European Application No. 09764927.1, Notice of Opposition dated Oct. 14, 2014, Reference# BRO-0001EP.

European Application No. 10732172.1, Extended European Search Report dated May 29, 2012, 5 pages.

European Application No. 16162568.6, Extended European Search Report dated Jul. 20, 2016, 6 pages.

European Patent Application No. 09764927.1, EPO's Communication of Notices of Opposition, dated Nov. 21, 2014.

European Patent Application No. 09764927.1, Opponent's Response to Submission of the Patentee dated Nov. 23, 2015.

European Patent Application No. 09764927.1, Patentee's Observations/Response dated May 27, 2015.

European Patent Application No. 11777704.5, European Search Report dated Jul. 26, 2013, 6 pages.

European Patent Application No. 13195379.6, Extended European Search Report and Opinion dated Mar. 13, 2014, 6 pages.

European Patent Application No. 13757482.8, Extended European Search Report dated Jun. 6, 2016, 5 pages.

European Patent Application No. 13775514.6, Extended European Search Report dated Dec. 1, 2015, 12 pages.

European Patent Application No. 13804085.2, Extended European Search Report dated Nov. 16, 2015, 10 pages.

European Patent Application No. 13828563.0, Extended European Search Report dated Feb. 12, 2016, 10 pages.

European Patent Application No. 14819680.1, Extended European Search Report dated Feb. 10, 2017, 10 pages.

European Patent Application No. 15758762.7, Extended European Search Report dated Sep. 22, 2017, 12 pages.

European Patent Application No. 15772627.4, Extended European Search Report dated Jul. 19, 2017, 8 pages.

European Patent Application No. 15779750.7, Extended European Search Report dated Aug. 9, 2017, 9 pages.

European Patent Application No. 15854358.7, Extended European Search Report dated Mar. 12, 2018, 12 pages.

European Patent Application No. 16165939.6, Extended European Search Report dated Oct. 7, 2016, 9 pages.

European Patent Application No. 16183402.3, Extended European Search Report dated Feb. 21, 2017, 8 pages.

European Patent Application No. 16756268.5, Extended European Search Report dated Oct. 22, 2018, 20 pages.

European Patent Application No. 16756268.5, Partial Supplementary European Search Report dated Jun. 19, 2018, 21 pages.

European Patent Application No. 16774304.6, Extended European Search Report dated Oct. 15, 2018, 9 pages.

European Patent Application No. 18153536.0, Extended European Search Report dated Jun. 6, 2018, 7 pages.

European Patent Application No. 18184843.3, Extended European Search Report dated Aug. 13, 2018, 10 pages.

Faham, M. et al. "Deep-sequencing approach for minimal residual disease detection in acute lymphoblastic leukemia", *Blood*, 120(26): 5173-5180 (2012).

Fanning, et al., "Development of the immunoglobulin repertoire." Clin Immunol Immunopathol. (Apr. 1996); 79(1): 1-14.

Feldhaus, et al., "Flow-cytometric isolation of human antibodies from a nonimmune *Saccharomyces cerevisiae* surface display library." Nat Biotechnol. (Feb. 2003); 21(2):163-70. Epub Jan. 21, 2003.

Ferradini et al. "Analysis of T Cell Receptor Variability in Tumor-infiltrating Lymphocytes from a Human Regressive Melanoma", *J. Clin. Invest.*, pp. 1183-1190 (1993).

Ferrero, et al. "Multiple myeloma shows no intra-disease clustering of immunoglobulin heavy chain genes", *Haematologica*, 97(6): 849-853 (2012). doi: 10.3324/haematol.2011.052852. Epub Dec. 29, 2011.

Flaherty et al. "Ultrasensitive detection of rare mutations using next-generation targeted resequencing", *Nucleic Acids Research*, 40(1): e2, 12 pages (2012).

Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", *Leukemia*, 22:771-782 (2008).

(56) References Cited

OTHER PUBLICATIONS

Födinger et al., "Multiplex PCR for rapid detection of T-cell receptor-gamma chain gene rearrangements in patients with lymphoproliferative diseases." British Journal of Haematology (1996); 94(1): 136-139.
Frank. "BARCRAWL and BARTAB: software tools for the design and implementation of barcoded primers for highly multiplexed DNA sequencing," *BMC Bioinformatics*, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", *Biotechniques*, 6(1): 112-125 (1999).
Freeman, J.D., et al. "Profiling the T-Cell Receptor Beta-Chain Repertoire by Massively Parallel Sequencing", *Genome Research*, 19(10):1817-1824 (2009). Epub Jun. 18, 2009.
Fridman, et al. "Prognostic and predictive impact of intra- and peritumoral immune infiltrates", *Cancer Research*, 71(17): 5601-5605 (2011). Epub Aug. 16, 2011.
Fritz et al. "Alterations in the spinal cord T cell repertoire during relapsing experimental autoimmune encephalomyelitis," *J Immunol*, 164:6662-6668 (2000).
Fu et al. "Counting individual DNA molecules by the stochastic attachment of diverse labels", *PNAS*, 108(22): 9026-9031 and Supporting Materials, 8 pages (2011).
Fuller, et al. "The challenges of sequencing by synthesis", *Nat Biotechnol.*, 7(11): 1013-1023 (2009) (Abstract only). Epub Nov. 6, 2009.
García-Castillo and Núnez, et al. "Detection of clonal immunoglobulin and T-cell receptor gene recombination in hematological malignancies: monitoring minimal residual disease", *Cardiovascular & Haematological Disorders-Drug Targets*, 9:124-135 (2009).
Gauss, et al. "Mechanistic constraints on diversity in human V(D)J recombination", *Mol Cell Biol.*, 16(1):258-269 (1996).
Gawad, et al. "Massive evolution of the immunoglobulin heavy chain locus in children with B precursor acute lymphoblastic leukemia", *Blood*, 120(22):4407-4417 (2012). Epub Aug. 28, 2012.
Gerlinger and Swanton. "How Darwinian models inform therapeutic failure initiated by clonal heterogeneity in cancer medicine", *British Journal of Cancer*, 103(8):1139-1143 (2010). Epub Sep. 28, 2010.
Gerlinger, M. et al. "Ultra deep T cell receptor sequencing reveals the complexity and intratumour heterogeneity of T cell clones in renal cell carcinomas", *Journal of Pathology*, 231:424-432 (2013).
Germano, et al. "Clonality profile in relapsed precursor-B-ALL children by GeneScan and sequencing analyses. Consequences on minimal residual disease monitoring", *Leukemia*, 17(8):1573-1582 (2003).
Giannoni, et al. Allelic exclusion and peripheral reconstitution by TCR transgenic T cells arising from transduced human hematopoietic stem/progenitor cells, Mol Ther., 21 (5):1044-1054 (2013). Epub Feb. 5, 2013.
Gilbert, et al. "The isolation of nucleic acids from fixed, paraffin-embedded tissues-which methods are useful when?", *PLoS One*, 2(6):e537, 12 pages (2007).
Giuggio, et al. "Evolution of the intrahepatic T cell repertoire during chronic hepatitis C virus infection", *Viral Immunology*, 18(1):179-189 (2005).
Gloor et al. "Microbiome profiling by Illumina sequencing of combinatorial sequence-tagged PCR products," *PLoS ONE*, 5(10): e15406, 15 pages (2010).
Godelaine, et al. "Polyclonal CTL responses observed in melanoma patients vaccinated with dendritic cells pulsed with a MAGE-3.A1 peptide", *J Immunol.*, 171(9):4893-4897 (2003).
Golembowski, et al. "Clonal evolution in a primary cutaneous follicle center B cell lymphoma revealed by single cell analysis in sequential biopsies", *Immunobiology*, 201(5):631-644 (2000).
Gonzalez et al., "Incomplete DJH rearrangements as a novel tumor target for minimal residual disease quantitation in multiple myeloma using real-time PCR", Leukemia, 17:1051-1057 (2003).

Gonzalez, et al. "Incomplete DJH rearrangements of the IgH gene are frequent in multiple myeloma patients: immunobiological characteristics and clinical implications", *Leukemia*, 17:1398-1403 (2003).
Gonzalez, S.F., et al. "Trafficking of B Cell Antigen in Lymph Nodes", *Ann. Rev. Immunol.*, 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", *J Immunol.*, 152(10):5109-5119 (1994).
Gottenberg, et al. "Markers of B-lymphocyte activation are elevated in patients with early rheumatoid arthritis and correlated with disease activity in the ESPOIR cohort", *Arthritis Res Ther.*, 11(4): R114 (2009). Epub Jul. 23, 2009.
Gratama and Kern. "Flow cytometric enumeration of antigen-specific T lymphocytes", *Cytometry A*, 58(1): 79-86 (2004).
Gratama, et al. "Measuring antigen-specific immune responses", 2008 update. *Cytometry A.*, 73(11): 971-974 (2008).
Green, et al. "Clonal diversity of Ig and T-cell-receptor gene rearrangements identifies a subset of childhood B-precursor acute lymphoblastic leukemia with increased risk of relapse", *Blood*, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", *Nature*, 446(7132): 153-158 (2007).
Grupp, et al. "Chimeric antigen receptor-modified T cells for acute lymphoid leukemia", N Engl J Med., 368(16):1509-1518 (2013). Epub Mar. 25, 2013.
Gulliksen, et al. "Real-time nucleic acid sequence-based amplification in nanoliter volumes", *Anal Chem.*, 76(1): 9-14, Abstract Only (2004).
Gunderson et al. "Decoding Randomly Ordered DNA Arrays", *Genome Research*, 14: 870-877 (2004).
Guo, et al. "Sequence changes at the V-D junction of the $V_H1$ heavy chain of anti-phosphocholine antibodies alter binding to and protection against *Streptococcus pneumoniae*", *Int Immunol.*, 9(5):665-677 (1997).
Gurrieri, et al. "Chronic lymphocytic leukemia B cells can undergo somatic hypermutation and intraclonal immunoglobulin $V_HDJ_H$ gene diversification", *J Exp Med.*, 196(5):629-639 (2002).
Hadrup, et al. "Parallel detection of antigen-specific T-cell responses by multidimensional encoding of MHC multimers", *Nat Methods*, 6(7): 520-526 (2009) (Abstract Only), doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for suboptimal specimens", *Leukemia & Lymphoma*, 48(7): 1338-1343 (2007).
Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.
Han et al. "Immunorepertoire analysis by multiplex PCR amplification and high throughput sequencing", *The Journal of Immunology*, 182:42.6, 1 page (2009).
Han, et al., "Linking T-cell receptor sequence to functional phenotype at the single-cell level." Nat Biotechnol. (2014); 32 (7): 684-692. Epub Jun. 22, 2014.
Hanahan, et al. "Hallmarks of cancer: the next generation", *Cell*, 144(5): 646-674 (2011). doi: 10.1016/j.cell.2011.02.013.
Hanes and Plückthun, "In vitro selection and evolution of functional proteins by using ribosome display." Proc Natl Acad Sci U S A. (May 1997); 94(10): 4937-4942.
Harismendy et al. "Evaluation of next generation sequencing platforms for population targeted sequencing studies", *Genome Biology*, 10:R32, 13 pages (2009).

(56) References Cited

OTHER PUBLICATIONS

Hawkins, et al. "Whole genome amplification—applications and advances", Curr Opin Biotechnol., 13(1): 65-67 (2002).

He, et al. "IgH gene rearrangements as plasma biomarkers in Non-Hodgkin's lymphoma patients", Oncotarget, 2(3): 178-185 (2011).

Hedegaard and Klemm, "Type 1 fimbriae of Escherichia coli as carriers of heterologous antigenic sequences." Gene (Dec. 1989); 85(1): 115-124.

Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.

Henegariu, O. et al., "Multiplex PCR: Critical Parameters and Step-by-Step Protocol," Biotechniques, Informa HealthCare, 23(3):504-511 (1997).

Hensel et al. "Simultaneous identification of bacterial virulence genes by negative selection", Science, 269(5222): 400-403 (1995).

Hesse, et al., "V(D)J recombination: a functional definition of the joining signals." Genes Dev. (Jul. 1989); 3(7): 1053-1061.

Hill, et al. "Using ecological diversity measures with bacterial communities", FEMS Microbiol Ecol., 43(1):1-11 (2003). doi: 10.1111/j.1574-6941.2003.tb01040.x.

Hirohata, et al. "Regulation of human B cell function by sulfasalazine and its metabolites", Int Immunopharmacol., 2(5): 631-640, Abstract Only (2002).

Hodges, E. et al. "Diagnostic role of tests for T cell receptor (TOR) genes", J Clin Pathol., 56(1): 1-11 (2003).

Hofnung, M., "Chapter 4 Expression of Foreign Polypeptides at the Escherichia coli Cell Surface." Methods in Cell Biology (1991); 34: 77-105.

Holmes and Al-Rubeai, "Improved cell line development by a high throughput affinity capture surface display technique to select for high secretors." J Immunol Methods. (Nov. 1999); 230(1-2): 141-147.

Holt and Jones. "The new paradigm of flow cell sequencing", Genome Research, 18:839-846 (2008).

Holt. "Q &A: BC cancer agency's Robert Holt on sequencing the immune repertoire in immune reconstitution," Genome Web (www.genomeweb.com) Jun. 30, 2009.

Hoogenboom, et al. "Multi-subunit proteins on the surface of filamentous phage: methodologies for displaying antibody (Fab) heavy and light chains", Nucleic Acids Res., 19(15): 4133-4137 (1991).

Hoogendoorn, et al. "Primary allogeneic T-cell responses against mantle cell lymphoma antigen-presenting cells for adoptive immunotherapy after stem cell transplantation", Clin Cancer Res., 11(14): 5310-5318 (2005).

Hoos, et al. "Improved endpoints for cancer immunotherapy trials", J Natl Cancer Inst., 102(18): 1388-1397 (2010). Epub Sep. 8, 2010.

Hosono, et al. "Unbiased whole-genome amplification directly from clinical samples", Genome Res., 13(5): 954-964 (2003). Epub Apr. 14, 2003.

Hoven, et al. "Detection and isolation of antigen-specific B cells by the fluorescence activated cell sorter (FACS)", J Immunol Methods, 117(2): 275-284, Abstract Only, 2 pages (1989).

Howe, et al. "T cell receptor clonotype analysis of T cell responses: Diagnostic application of a clonotypic database", Blood (2003); 102 (11): Abstract 3918, p. 54b, 1 page.

Howie, et al., "High throughput pairing of T cell receptor α and β sequences." Science Translational Medicine (2015); 7(301): 301ra131, and supplementary materials, 19 pages.

Huh, et al. "Microfluidics for flow cytometric analysis of cells and particles", Physiol Meas., 26(3): R73-98, Abstract Only (2005). Epub Feb. 1, 2005.

Huijsmans, et al. "Comparative analysis of four methods to extract DNA from paraffin-embedded tissues: effect on downstream molecular applications", BMC Res Notes, 3:239, 9 pages (2010).

Huse, et al. "Generation of a large combinatorial library of the immunoglobulin repertoire in phage lambda", Science, 246(4935): 1275-1281, Abstract Only (1989).

Hwang, H.Y. et al. "Identification of a Commonly used CDR3 Region of Infiltrating T Cells Expressing Vβ13 and Vβ15 Derived from Psoriasis Patients", The Journal of Investigative Dermatology, 120(3):359-364 (2003).

Iancu, et al. "Profile of a serial killer: cellular and molecular approaches to study individual cytotoxic T-cells following therapeutic vaccination", J Biomed Biotechnol., 2011: 452606 (2011). doi: 10.1155/2011/452606. Epub Nov. 14, 2010.

Ilakovac, V., "Statistical hypothesis testing and some pitfalls." Biochemia Medica (2009); 19(1): 10-16, 4 pages, [online], [Retrieved on Apr. 12, 2016], Retrieved from the Internet: <URL:http://www.biochemia-medica.com/contentlstatistical-hypothesis-testing-and-some-pitfalls>PDF.

Illumina Systems & Software, Technology Spotlight, DNA Sequencing with Solexa® Technology, Illumina, Inc., Pub. No. 770-2007-002, 4 pages (2007).

Illumina. "Technical Note: Systems and Software. Calling sequencing SNPs", 3 pages (2010).

Illumina. Data Sheet, "TruSeq™ exome enrichment kit", 5 pages (2011).

Illumina. Data Sheet: Sequencing. Genomic Sequencing. Pub. No. 770.2008-016 Reference states: "Current as of Jan. 30, 2009", 6 pages, Copyright 2010.

Illumina. TruSeq Sample Preparation Kit and Data Sheet. Illumina, Inc., San Diego, CA, 4 pages (2011).

Ishii et al. "Isolation and expression profiling of genes upregulated in the peripheral blood cells of systemic lupus erythematosus patients," DNA Research, 12:429-439 (2005).

Jabara et al. "Accurate sampling and deep sequencing of the HIV-1 protease gene using a Primer ID", PNAS, 108(50): 20166-20171 (2011).

Jacobi et al. "Activated memory B cell subsets correlate with disease activity in systemic lupus erythematosus: delineation by expression of CD27, IgD, and CD95", Arthritis & Rheumatism, 58(6):1762-1773 (2008).

Jacobi et al. "Correlation between circulating CD27$^{high}$ plasma cells and disease activity in patients with systemic lupus erythematosus" Arthritis & Rheumatism, 48(5):1332-1342 (2003).

Jaffe, et al. "Classification of lymphoid neoplasms: the microscope as a tool for disease discovery", Blood, 112(12): 4384-4399 (2008). doi: 10.1182/blood-2008-07-077982.

Jalla, et al. "Enumeration of lymphocyte subsets using flow cytometry: Effect of storage before and after staining in a developing country setting", Indian J Clin Biochem., 19(2): 95-99 (2004). doi: 10.1007/BF02894264.

Jena, et al. "Amplification of genes, single transcripts and cDNA libraries from one cell and direct sequence analysis of amplified products derived from one molecule", J. Immunol. Methods, 190:199-213 (1996).

Jochems and Schlom. "Tumor-infiltrating immune cells and prognosis: the potential link between conventional cancer therapy and immunity", Exp Biol Med (Maywood), 236(5):567-579 (2011). Epub Apr. 12, 2011.

Jung, et al. "Unraveling V(D)J recombination: insights into gene regulation", Cell, 116(2): 299-311 (2004).

Jurkat, Clone 6-1 (ATCC TIB-152) Webpage retrievable from the ATCC under http://www.lgcstandards-atcc.org/Products/ All MB-152.aspx#characteristics. Accessed Oct. 14, 2014.

Kanagawa, T., "Bias and artifacts in multitemplate polymerase chain reactions (PCR)." J Biosci Bioeng. (2003); 96(4): 317-323.

Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt.2012.06.005. Epub Jun. 12, 2012.

Kato et al. "Analysis of accumulated T cell clonotypes in patients with systemic lupus erythematosus," Arthritis & Rheumatism, 43(12):2712-2721 (2000).

(56) References Cited

OTHER PUBLICATIONS

Katz, S.C. et al. "T Cell Infiltrate Predicts Long-Term Survival Following Resection of Colorectal Cancer Liver Metastases," Ann. Surg. Oncol., 16:2524-2530 (2009).
Kedzierska, et al. "Tracking phenotypically and functionally distinct T cell subsets via T cell repertoire diversity", Mol Immunol., 45(3): 607-618 (2008). Epub Aug. 24, 2007.
Kiianitsa, et al., "Development of Tools for T-Cell Repertoire Analysis (TCRB Spectratyping) for the Canine Model of Hematopoietic Cell Transplantation", Blood, ASH—Annual Meeting Abstracts, 110 (11): Abstract 4873, 2 pages (2007).
Kim, et al. "An efficient and reliable DNA extraction method for preimplantation genetic diagnosis: a comparison of allele drop out and amplification rates using different single cell lysis methods", Fertility and Sterility, 92: 814-818 (2009).
Kim, et al. "Polony multiplex analysis of gene expression (PMAGE) in mouse hypertrophic cardiomyopathy", Science, 316(5830):1481-1484 (2007).
Kinde et al. "Detection and quantification of rare mutations with massively parallel sequencing," PNAS, 108(23): 9530-9535 and Supporting Information, 16 pages (2011).
Kircher, et al. "Improved base calling for the Illumina Genome Analyzer using machine learning strategies", Genome Biol., 10(8): R83, 9 pages (2009). doi: 10.1186/GB-2009-10-8-r83. Epub Aug. 14, 2009.
Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.
Kita, et al. "T cell receptor clonotypes in skin lesions from patients with systemic lupus erythematosus", Journal of Investigative Dermatology,110(1): 41-46 (1988).
Kivioja et al. "Counting absolute numbers of molecules using unique molecular identifiers," Nature Methods, 9(1): 72-76 (2012).
Klarenbeek, P.L. et al. "Deep sequencing of antiviral T-cell responses to HCMV and EBV in humans reveals a stable repertoire that is maintained for many years." PLoS Pathogens (2012); 8.9: e1002889.
Klarenbeek, P.L. et al. "Human T-cell memory consists mainly of unexpanded clones", Immunology Letters, 133: 42-48 (2010).
Klauser, et al., "Extracellular transport of cholera toxin B subunit using Neisseria IgA protease beta-domain: conformation-dependent outer membrane translocation." The EMBO Journal (Jun. 1990); 9(6): 1991-1999.
Klenerman, et al. "Tracking T cells with tetramers: new tales from new tools", Nat Rev Immunol., 2(4):263-272 (2002).
Klinger et al. "Combining next-generation sequencing and immune assays: a novel method for identification of antigen-specific T cells", PLoS One, 8(9): e74231, 1-9 (2013).
Kneba, et al. "Characterization of clone-specific rearrangement T-cell receptor gamma-chain genes in lymphomas and leukemias by the polymerase chain reaction and DNA sequencing", Blood, 84(2):574-581 (1994).
Kneba, M., et al. "Analysis of Rearranged T-cell Receptor β-Chain Genes by Polymerase Chain Reaction (PCR) DNA Sequencing and Automated High Resolution PCR Fragment Analysis", Blood, 86:3930-3937 (1995).
Kobari, et al. "T cells accumulating in the inflamed joints of a spontaneous murine model of rheumatoid arthritis become restricted to common clonotypes during disease progression", Int Immunol., 16(1):131-138 (2004).
Koboldt et al., "VarScan: variant detection in massively parallel sequencing of individual and pooled samples", Bioinformatics, 25(17): 2283-2285 (2009).
Koch, et al. "Tumor infiltrating T lymphocytes in colorectal cancer: Tumor-selective activation and cytotoxic activity in situ," Ann Surg., 244(6): 986-992; discussion 992-993 (2006).
Kohlmann, et al. "Integration of next-generation sequencing into clinical practice: are we there yet?", Semin Oncol., 39(1): 26-36, Abstract Only (2012).
Kojima et al. "PCR amplification from single DNA molecules on magnetic beads in emulsion: application for high-throughput screening of transcription factor targets", Nucleic Acids Research, 33:17, e150, 9 pages (2005).
Krause et al. "Epitope-Specific Human Influenza Antibody Repertoires Diversify by B Cell Intraclonal Sequence Divergence and Interclonal Convergence", The Journal of Immunology, 187: 3704-3711 (2011).
Krueger, et al. "Large scale loss of data in low-diversity illumina sequencing libraries can be recovered by deferred cluster calling", PLoS One, 6(1): e16607, 7 pages (2011).
Ku, et al. "Exome sequencing: dual role as a discovery and diagnostic tool", Ann Neurol., 71(1):5-14, Abstract Only (2012). doi: 10.1002/ana.22647.
Kumar, et al. "PEG-labeled nucleotides and nanopore detection for single molecule DNA sequencing by synthesis", Sci Rep., 2:684, 8 pages (2012). Epub Sep. 21, 2012.
Kwak, et al. "Induction of immune responses in patients with B-cell lymphoma against the surface-immunoglobulin idiotype expressed by their tumors", N Engl J Med., 327(17):1209-1215 (1992).
Kyu et al. "Frequencies of human influenza-specific antibody secreting cells or plasmablasts post vaccination from fresh and frozen peripheral blood mononuclear cells", Journal of Immunological Methods, 340: 42-47 (2009).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", Blood, vol. 120 , No. 21, Abstract 788 (Conference Abstract), Entire Abstract (2012).
Ladetto, M. et al. "Real-time polymerase chain reaction in multiple myeloma: Quantitative analysis of tumor contamination of stem cell harvests", Experimental Hematology, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", American Society for Blood and Marrow Transplantation, 6(3):241-253 (2000).
Langerak, et al. "Immunoglobulin/T-cell receptor clonality diagnostics", Expert Opin. Med. Diagn., 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-CT98-3936", Leukemia, 21(2):222-229 (2007).
Laplaud et al. "Blood T-cell receptor β chain transcriptome in multiple sclerosis. Characterization of the T cells with altered CDR3 length distribution", Brain, 127:981-995 (2004).
Laplaud et al. "Serial blood T cell repertoire alterations in multiple sclerosis patients; correlation with clinical and MRI parameters", Journal of Neuroimmunology, 177(1-2):151-160 (2006).
Larijani, et al., "The role of components of recombination signal sequences in immunoglobulin gene segment usage: a V81x model." Nucleic Acids Research (Jan. 1999); 27(11): 2304-2309.
Larimore, K., et al. "Shaping of Human Germline IgH Repertoires Revealed by Deep Sequencing", The Journal of Immunology, 189(6): 3221-3230 (2012).
Lassmann, et al. "Application of BIOMED-2 primers in fixed and decalcified bone marrow biopsies: analysis of immunoglobulin H receptor rearrangements in B-cell non-Hodgkin's lymphomas", J Mol Diagn., 7(5): 582-591 (2005).
Lee, et al. "Characterization of circulating T cells specific for tumor-associated antigens in melanoma patients", Nat Med., 5(6): 677-685, Abstract Only (1999).
Lee, et al. "Prognostic implications of type and density of tumour-infiltrating lymphocytes in gastric cancer", Br J Cancer, 99(10): 1704-1711 (2008). Epub Oct. 21, 2008.
Lee, et al., "A Functional Analysis of the Spacer of V(D)J Recombination Signal Sequences." PLoS Biology (2003); 1(1): e1, pp. 056-059.
Lefranc. "IMGT, the international ImMunoGeneTics database", Nucleic Acids Res., 31(1):307-310 (2003).
Leiden, J.M. et al. "The Complete Primary Structure of The T -Cell Receptor Genes From an Alloreactive Cytotoxic Human T-Lymphocyte Clone", Immunogenetics, 24(1): 17-23 (1986).

(56) References Cited

OTHER PUBLICATIONS

Leisner, et al. "One-pot, mix-and-read peptide-MHC tetramers", *PLoS One*, 3(2):e1678, 11 pages (2008).

Leone, et al. "Molecular beacon probes combined with amplification by NASBA enable homogeneous, real-time detection of RNA", *Nucleic Acids Research*, 26(9): 2150-2155 (1998).

Leproust, et al. "Synthesis of high-quality libraries of long (150mer) oligonucleotides by a novel depurination controlled process", *Nucleic Acids Res.*, 38(8): 2522-2540 (2010). Epub Mar. 22, 2010.

Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).

Li, et al. "An improved one-tube RT-PCR protocol for analyzing single-cell gene expression in individual mammalian cells", *Anal. Bioanal. Chem.*, 397:1853-1859 (2010).

Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).

Li, et al. "Detailed clonality analysis of relapsing precursor B acute lymphoblastic leukemia: implications for minimal residual disease detection", *Leukemia Research*, 25:1033-1045 (2001).

Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).

Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).

Li, et al. "β cell-specific CD4+ T cell clonotypes in peripheral blood and the pancreatic islets are distinct", *J Immunol.*, 183(11): 7585-7591 (2009). Epub Nov. 16, 2009.

Liedtke, et al. "A comparison of methods for RNA extraction from lymphocytes for RT-PCR", *PCR Methods and Applications*, 4(3): 185-187 (1994).

Lin, et al. "Multiplex genotype determination at a large number of gene loci", *Proc Natl Acad Sci USA*, 93(6): 2582-2587 (1996).

Linnemann, et al., "High-throughput identification of antigen-specific TCRs by TCR gene capture." Nature Medicine (Nov. 2013); 19 (11): 1534-1541. Epub Oct. 13, 2013.

Linnemann, et al., "TCR repertoires of intratumoral T-cell subsets." Immunological Reviews (2014); 257 (1): 72-82.

Liu, et al. "CD127 expression inversely correlates with FoxP3 and suppressive function of human CD4+ T reg cells", *J Exp Med.*, 203(7): 1701-1711 (2006). Epub Jul. 3, 2006.

Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.

Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).

Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).

Lorimer, I. A., and Pastan, Ira. "Random recombination of antibody single chain Fv sequences after fragmentation with DNaseI in the presence of Mn2+." Nucleic Acids Research (1995); 23.15: 3067-3068.

Lossius, et al., "High-throughput sequencing of TCR repertoires in multiple sclerosis reveals intrathecal enrichment of EBV-reactive CD8+ T cells." European Journal of Immunology (Nov. 2014); 44 (11): 3439-3452. Epub Sep. 16, 2014.

Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.

Lovisa, et al. "IGH and IGK gene rearrangements as PCR targets for pediatric Burkitt's lymphoma and mature B-ALL MRP analysis", *Lab Invest.*, 89(10):1182-1186 (2009).

Lowe, T., et al., "A computer program for selection of oligonucleotide primers for polymerase chain reactions," Nucleic Acids Research (1990); 18(7):1757-1761.

Lowman, et al. "Monovalent phage display: a method for selecting variant proteins from random libraries", *Methods: A Companion to Methods in Enzymology*, 3: 205-216, Abstract Only (1991).

Lu, et al., "Expression of thioredoxin random peptide libraries on the *Escherichia coli* cell surface as functional fusions to flagellin: a system designed for exploring protein-protein interactions." Biotechnology (NY). (Apr. 1995); 13(4): 366-372.

Lúcio, P. et al. "Flow cytometric analysis of normal B cell differentiation: a frame of reference for the detection of minimal residual disease in precursor-B-ALL", *Leukemia*, 13:419-427 (1999).

Luo et al. "Analysis of the interindividual conservation of T cell receptor α- and β-chain variable regions gene in the peripheral blood of patients with systemic lupus erythematosus", *Clinical & Experimental Immunology*, 154(3):316-324(2008).

Lyamichev, et al. "Polymorphism identification and quantitative detection of genomic DNA by invasive cleavage of oligonucleotide probes", *Nat Biotechnol.*, 17(3): 292-396 (1999).

Mackay, et al. "Real-time PCR in virology", *Nucleic Acids Res.*, 30(6): 1292-1305 (2002).

Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.

Manion et al., "Reducing Error in Next Generation Sequencing Data with NextGENe Software's Condensation Tool™", Mar. 2009, pp. 1-3.

Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.

Mar et al. "Inferring steady state single-cell gene expression distributions from analysis of mesoscopic samples", *Genome Biology*, 7(12): R119, 12 pages (2006).

Mardis. "Next-generation DNA sequencing methods", *Annu. Rev. Genomics Hum. Genet.*, 9:387-402 (2008). doi: 10.1146/annurev.genom.9.081307.164359.

Margulies, et al. "Genome sequencing in microfabricated high-density picolitre reactors", *Nature*, 437(7057):376-380 (2005). Epub Jul. 31, 2005.

Mariani, S. et al., "Comprehensive assessment of the TCRBV repertoire in small T-cell samples by means of an improved and convenient multiplex PCR method," *Experimental Hematology*, 37(6):728-738 (2009).

Markoulatos, P. et al., "Multiplex Polymerase Chain Reaction: A Practical Approach", Journal of Clinical Laboratory Analysis, 16:47-51 (2002).

Martin-Jimenez, et al. "Molecular characterization of heavy chain immunoglobulin gene rearrangements in Waldenstrom's macroglobulinemia and IgM monoclonal gammopathy of undetermined significance", *Haematologica*, 92(5): 635-642 (2007).

Mary et al. "Analysis of gene expression at the single-cell level using microdroplet-based microfluidic technology", *Biomicrofluidics*, 5: 024109-1-024109-10 (2011).

Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).

Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).

Mato et al. "Correlation of clonal T cell expansion with disease activity in systemic lupus erythematosus", *Int Immunol.*, 9(4):547-554 (1997).

(56) References Cited

OTHER PUBLICATIONS

Matolcsy, et al. "Clonal evolution of B cells in transformation from low- to high-grade lymphoma", *Eur. J. Immunol.*,29(4):1253-1264 (1999).
Matsumoto et al. "CDR3 spectratyping analysis of the TCR repertoire in Myasthenia Gravis", *The Journal of Immunology*, 176:5100-5107 (2006).
Matsumoto et al. "Complementarity-determining region 3 spectratyping analysis of the TCR repertoire in multiple sclerosis", *The Journal of Immunology*, 170:4846-4853 (2003).
Mazor et al. "Antibody internalization studied using a novel IgG binding toxin fusion", *Journal of Immunological Methods*, 321: 41-59 (2007).
Mazumder, et al., "Detection of multiple myeloma cells in peripheral blood using high-throughput sequencing assay" *Blood*, vol. 120 , No. 21, Abstract 321 (Conference Abstract), Entire Abstract (2012).
McCafferty, et al., "Phage antibodies: filamentous phage displaying antibody variable domains." Nature (Dec. 1990); 348(6301): 552-554.
McCloskey et al. "Encoding PCR products with batch-stamps and barcodes," *Biochem. Genet.*, 45: 761-767 (2007).
McLean et al. "Recognition of human cytomegalovirus by human primary immunoglobulins identifies an innate foundation to an adaptive immune response", J. Immunol., 174(8): 4768-4778 (2005).
Mei et al. "Blood-borne human plasma cells in steady state are derived from mucosal immune responses", *Blood*, 113(11): 2461-2469 (2009).
Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).
Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.
Meier, et al. "The influence of different stimulation conditions on the assessment of antigen-induced CD154 expression on CD4+ T cells", *Cytometry A.*, (11):1035-1042 (2008). doi: 10.1002/cyto.a. 20640.
Meijer et al. "Isolation of Human Antibody Repertoires with Preservation of the Natural Heavy and Light Chain Pairing", *J. Mol. Biol.*, 358: 764-772 (2006).
Meleshko, et al. "Rearrangements of IgH, TCRD and TCRG genes as clonality marker of childhood acute lymphoblastic leukemia", *Experimental Oncology*, 27(4):319-324 (2005).
Menezes et al. "A public T cell clonotype within a heterogeneous autoreactive repertoire is dominant in driving EAE", *J Clin Invest*, 117(8):2176-2185 (2007).
Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", *Nature Reviews, Genetics*, 11:31-46 (2010).
Meyer et al. "Targeted high-throughput sequencing of tagged nucleic acid samples", *Nucleic Acids Research*, 35(15): e97, 5 pages (2007).
Miceli and Parnes. "The roles of CD4 and CD8 in T cell activation", *Seminars in Immunology*, 3(3): 133-141 (1991). Abstract only.
Michálek, et al. "Detection and long-term in vivo monitoring of individual tumor-specific T cell clones in patients with metastatic melanoma", *J Immunol.*, 178(11):6789-6795 (2007).
Michálek, et al. "Identification and monitoring of graft-versus-host specific T-cell clone in stem cell transplantation", *The Lancet*, 361(9364): 1183-1185 (2003).
Miller, et al., "Assembly algorithms for next-generation sequencing data", Genomics, 95(6): 315-327 (2010).
Miltenyi, et al. "High gradient magnetic cell separation with MACS", *Cytometry*, 11(2): 231-238 (1990).

Miner et al. "Molecular barcodes detect redundancy and contamination in hairpin-bisulfite PCR", *Nucleic Acids Research*, 32(17): e135, 4 pages (2004).
Miqueu, P et al. "Statistical analysis of CDR3 length distributions for the assessment of T and B cell repertoire biases", *Molecular Immunology*, 44:1057-1064 (2007).
Miqueu, P., et al., "Analysis of the peripheral T-cell repertoire in kidney transplant patients." Eur J Immunol. (Nov. 2010); 40(11): 3280-3290. Epub Oct. 27, 2010.
Mitra, et al. "Fluorescent in situ sequencing on polymerase colonies", *Anal Biochem.*, 320(1): 55-65, Abstract Only (2003).
Miyashita, et al. "N-Methyl substituted 2',4'—BNANC: a highly nuclease-resistant nucleic acid analogue with high-affinity RNA selective hybridization", *Chem Commun* (Camb), (36): 3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).
Molloy, et al. "Soluble T cell receptors: novel immunotherapies", *Curr Opin Pharmacol.*, 5(4): 438-443 (2005) (Abstract Only).
Monod, M.Y. et al. "IMGT/JunctionAnalysis: the first tool for the analysis of the immunoglobulin and T cell receptor complex V-J and V-D-J Junctions", *Bioinformatics*, 20(Suppl 1):i379-385 (2004).
Moody, et al. "Antigen-specific B cell detection reagents: use and quality control", *Cytometry A.*, 73(11): 1086-1092 (2008). doi: 10.1002/cyto.a.20599.
Morgan, et al. "Cancer regression in patients after transfer of genetically engineered lymphocytes", *Science*, 314(5796): 126-129 (2006). Epub Aug. 31, 2006.
Morozova et al. "Applications of New Sequencing Technologies for Transcriptome Analysis", *Annu. Rev. Genomics Hum. Genet.*, 10:135-151 (2009).
Morrissy et al. "Next-generation tag sequencing for cancer gene expression profiling", *Genome Research*, 19: 1825-1835 (2009).
Moss, et al. "The human T cell receptor in health and disease", *Annu. Rev. Immunol.*, 10:71-96 (1992).
Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.
Müller, et al., "Random peptide libraries displayed on adeno-associated virus to select for targeted gene therapy vectors." Nat Biotechnol. (Sep. 2003); 21(9): 1040-1046. Epub Aug. 3, 2003.
Muraro et al. "Molecular tracking of antigen-specific T cell clones in neurological immune-mediated disorders", *Brain*, 126(Pt 1):20-31 (2003).
Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.
Nadel, et al., "Decreased Frequency of Rearrangement due to the Synergistic Effect of Nucleotide Changes in the Heptamer and Nonamer of the Recombination Signal Sequence of the Vk Gene A2b, Which Is Associated with Increased Susceptibility of Navajos to Haemophilus influenzae Type b Disease." The Journal of Immunology (1998); 161(11): 6068-6073.
Nadel, et al., "Sequence of the Spacer in the Recombination Signal Sequence Affects V(D)J Rearrangement Frequency and Correlates with Nonrandom Vk Usage In Vivo." Jornal of Experimental Medicine (1998); 187 (9): 1495-1503.
Naito, et al. "CD8+ T cells infiltrated within cancer cell nests as a prognostic factor in human colorectal cancer", *Cancer Research*, 58(16): 3491-3494 (1998).
Nakajima, et al., "Expression of random peptide fused to invasin on bacterial cell surface for selection of cell-targeting peptides." Gene (Dec. 2000); 260 (1-2): 121-131.
Nardi, et al. "Quantitative monitoring by polymerase colony assay of known mutations resistant to ABL kinase inhibitors", *Oncogene*, 27(6):775-782 (2008). Epub Aug. 6, 2007, 1-8.
Navarrete, et al. "Upfront immunization with autologous recombinant idiotype Fab fragment without prior cytoreduction in indolent

(56) References Cited

OTHER PUBLICATIONS

B-cell lymphoma", *Blood*, 117(5): 1483-1491 (2011). doi: 10.1182/blood-201 0-06-292342. Epub Nov. 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Nelson. "CD20+ B cells: the other tumor-infiltrating lymphocytes", *The Journal of Immunology*, 185(9): 4977-4982 (2010). doi: 10.4049/jimmunol.1001323.

Newman, et al. "Identification of an antigen-specific B cell population", *J Immunol Methods*, 272(1-2): 177-187, Abstract Only (2003).

Newton, et al., "Immune response to cholera toxin epitope inserted in *Salmonella flagellin*." Science (Apr. 1989); 244(4900): 70-72.

Nguyen et al. "Identification of errors introduced during high throughput sequencing of the T cell receptor repertoire" *BMC Genomics*, 12:106, 13 pages (2011).

Nielsen, et al. "Peptide nucleic acid (Pna). A DNA mimic with a pseudopeptide backbone", *Chem. Soc. Rev.*, 26:73-78, Abstract Only (1997).

Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Oble, et al. "Focus on TILs: prognostic significance of tumor infiltrating lymphocytes in human melanoma", *Cancer Immunity*, 9: 3, 20 pages (2009).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ogino and Wilson., "Quantification of PCR Bias Caused by a Single Nucleotide Polymorphism in SMN Gene Dosage Analysis." The Journal of Molecular Diagnostics (Nov. 2002); 4(4): 185-190.

Ogle, et al. "Direct measurement of lymphocyte receptor diversity", *Nucleic Acids Research*, 31 (22):e139, 6 pages (2003).

Ohlin, Mats, et al. "Light chain shuffling of a high affinity antibody results in a drift in epitope recognition." Molecular Immunology (1996); 33.1: 47-56.

Ohtani. "Focus on TILs: prognostic significance of tumor infiltrating lymphocytes in human colorectal cancer", *Cancer Immunity*, 7: 4, 9 pages (2007).

Okajima et al. "Analysis of T cell receptor Vβ diversity in peripheral CD4+ and CD8+ T lymphocytes in patients with autoimmune thyroid diseases", *Clinical & Experimental Immunology*, 155:166-172 (2008).

Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.

Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

Packer and Muraro. "Optimized clonotypic analysis of T-cell receptor repertoire in immune reconstitution", *Experimental Hematology*, 35(3):516-521 (2007).

Palmowski, et al. "The use of HLA class I tetramers to design a vaccination strategy for melanoma patients", *Immunol Rev.*, 188: 155-163 (2002) (Abstract Only).

Pan, et al. "A new FACS approach isolates hESC derived endoderm using transcription factors", *PLoS One*, 6(3): e17536, 9 pages (2011). doi: 10.1371/journal.pone.0017536.

Panzara, et al., "Analysis of the T cell repertoire using the PCR and specific oligonucleotide primers." Biotechniques (1992); 12(5): 728-735.

Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).

Parameswaran et al. "A pyrosequencing-tailored nucleotide barcode design unveils opportunities for large-scale sample multiplexing", *Nucleic Acids Research*, 35(19): e130, 9 pages (2007).

Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.

Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.

PCT/US2009/006053, International Preliminary Report on Patentability dated May 10, 2011, 5 pages.

PCT/US2009/006053, International Search Report dated Jun. 15, 2010, 6 pages.

PCT/US2009/006053, Written Opinion dated Jun. 15, 2010, 4 pages.

PCT/US2010/021264, International Preliminary Report on Patentability dated Jul. 19, 2011, 5 pages.

PCT/US2010/021264, International Search Report and Written Opinion dated Apr. 14, 2010, 7 pages.

PCT/US2010/037477, International Preliminary Report on Patentability dated Jan. 4, 2012, 7 pages.

PCT/US2010/037477, International Search Report and Written Opinion dated Sep. 24, 2010, 10 pages.

PCT/US2011/000791, International Preliminary Report on Patentability dated Nov. 6, 2012, 10 pages.

PCT/US2011/000791, International Search Report and Written Opinion dated Sep. 22, 2011, 13 pages.

PCT/US2011/049012, International Preliminary Report on Patentability dated Feb. 26, 2013, 5 pages.

PCT/US2011/049012, International Search Report and Written Opinion dated Apr. 10, 2012, 9 pages.

PCT/US2013/028942, International Preliminary Report on Patentability dated May 5, 2015, 9 pages.

PCT/US2013/028942, International Search Report and Written Opinion dated May 9, 2013, 10 pages.

PCT/US2013/035857, International Preliminary Report on Patentability dated Oct. 14, 2014, 8 pages.

PCT/US2013/035857, International Search Report and Written Opinion dated Aug. 7, 2013,10 pages.

PCT/US2013/040221, International Preliminary Report on Patentability dated Apr. 24, 2014, 41 pages.

PCT/US2013/040221, International Search Report and Written Opinion dated Sep. 23, 2013, 15 pages.

PCT/US2013/045276, International Preliminary Reporton Patentability dated Dec. 16, 2014, 2014, 7 pages.

PCT/US2013/045276, International Search Report and Written Opinion dated Jan. 29, 2014, 11 pages.

PCT/US2013/045994, International Preliminary Reporton Patentability dated Dec. 16, 2014, 10 pages.

PCT/US2013/045994, International Search Report and Written Opinion dated Oct. 25, 2013, 15 pages.

PCT/US2013/051539, International Preliminary Reporton Patentability dated Jan. 27, 2015, 7 pages.

PCT/US2013/051539, International Search Report and Written Opinion dated Nov. 27, 2013, 9 pages.

PCT/US2013/054189, International Preliminary Reporton Patentability dated Feb. 10, 2015, 7 pages.

PCT/US2013/054189, International Search Report and Written Opinion dated Oct. 21, 2013, 10 pages.

PCT/US2014/030859, International Preliminary Reporton Patentability dated Sep. 15, 2015, 8 pages.

PCT/US2014/030859, International Search Report and Written Opinion dated Jul. 18, 2014, 14 pages.

(56) References Cited

OTHER PUBLICATIONS

PCT/US2014/044971, International Preliminary Examination Report dated Jan. 6, 2016, 12 pages.
PCT/US2014/044971, International Search Report and Written Opinion dated Oct. 30, 2014, 14 pages.
PCT/US2015/018967, International Preliminary Report on Patentability dated Oct. 18, 2016, 11 pages.
PCT/US2015/018967, International Search Report and Written Opinion dated Jul. 30, 2015, 17 pages.
PCT/US2015/019029, International Preliminary Report on Patentability dated Sep. 6, 2016, 14 pages.
PCT/US2015/019029, International Search Report and Written Opinion dated Sep. 15, 2015, 19 pages.
PCT/US2015/023915, International Preliminary Report on Patentability dated Oct. 4, 2016, 7 pages.
PCT/US2015/023915, International Search Report and Written Opinion dated Aug. 26, 2015, 11 pages.
PCT/US2015/058035, International Preliminary Report on Patentability dated May 2, 2017, 8 pages.
PCT/US2015/058035, International Search Report and Written Opinion dated Jan. 29, 2016, 14 pages.
PCT/US2016/019343, International Preliminary Report on Patentability dated Aug. 29, 2017, 14 pages.
PCT/US2016/019343, International Search Report and Written Opinion dated Jul. 22, 2016, 23 pages.
PCT/US2016/025535, International Preliminary Report on Patentability dated Oct. 3, 2017, 7 pages.
PCT/US2016/025535, International Search Report and Written Opinion dated Jul. 11, 2016, 9 pages.
Peet. "The Measurement of Species Diversity", *Annual Review of Ecology and Systematics*, 5: 285-307, Abstract Only (1974).
Pekin, D. et al. "Quantitative and sensitive detection of rare mutations using droplet-based microfluidics", *Lab Chip*, 11(3): 2156-2166 (2011).
Pels et al. "Clonal evolution as pathogenetic mechanism in relapse of primary CNS lymphoma", *Neurology*, 63(1):167-169 (2004).
Perkel, J. "Overcoming the Challenges of Multiplex PCR", *Biocompare Editorial Article*, Oct. 23, 2012, 6 Pages, can be retrieved at URL:http://www.biocompare.com/Editorial-Articles/117895-Multiplex-PCR/>.
Petrosino, et al. "Metagenomic pyrosequencing and microbial identification", *Clin Chem.*, 55(5): 856-866 (2009). doi: 10.1373/clinchem.2008.107565. Epub Mar. 5, 2009.
Pira et al. "Human naive CD4 T-cell clones specific for HIV envelope persist for years in vivo in the absence of antigenic challenge", *J Acquir Immune Defic Syndr.*, 40(2):132-139 (2005).
Plasilova et al. "Application of the Molecular Analysis of the T-Cell Receptor Repertoire in the Study of Immune-Mediated Hematologic Diseases", *Hematology*, 8(3): 173-181 (2003).
Pohl, G. and Shih. "Principle and applications of digital PCR", *Expert Rev. Mol. Diagn.*, 4(1):41-47 (2004).
Polz and Cavanaugh. "Bias in Template-to-Product Ratios in Multitemplate PCR", *Applied and Environmental Microbiology*, 64(10): 3724-3730 (1998).
Pop and Salzberg. "Bioinformatics challenges of new sequencing technology", *NIH, Trends Genet.*, 24(3): 142-149 (2008).
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Pourmand, et al. "Direct electrical detection of DNA synthesis", *PNAS*, 103(17): 6466-6470 (2006). Epub Apr. 13, 2006.
Prabakaran et al. "454 antibody sequencing—error characterization and correction", *BMC Research Notes*, 4: 404 (2011).
Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant, 13(11): 3010-3020 (2013). doi: 10.1111/ajt.12433. Epub Sep. 18, 2013..
Qu, et al., "Efficient frequency-based de novo short-read clustering for error trimming in next-generation sequencing", Genome Research, 19:1309-1315 (2009).
Qiu et al. "DNA sequence-based "bar codes" for tracking the origins of expressed sequence tags from a maize cDNA library constructed using multiple mRNA sources", *Plant Physiology*, 133(2): 475-481 (2003).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Ramsden, et al., "Conservation of sequence in recombination signal sequence spacers." Nucleic Acids Res. (May 1994); 22(10): 1785-1796.
Rasmussen, T. et al. "Quantitation of minimal residual disease in multiple myeloma using an allele-specific real-time PCR assay", *Experimental Hematology*, 28:1039-1045 (2000).
Ray, et al. "Single cell multiplex PCR amplification of five dystrophin gene exons combined with gender determination", *Molecular Human Reproduction*, 7(5): 489-494 (2001).
Reddy and Georgiou. "Systems analysis of adaptive immunity by utilization of high-throughput technologies", *Current Opinion in Biotechnology*, 22(4): 584-589 (2011).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reinartz et al. "Massively parallel signature sequencing (MPSS) as a tool for in-depth quantitative gene expression profiling in all organisms", *Brief Fund Genomic Proteomic.*, 1(1): 95-104 (2002).
Reischl and Kochanowski. "Quantitative PCR. A Survey of the Present Technology", *Molecular Biotechnology*, 3:55-71 (1995).
Ria, et al. "Collagen-specific T-cell repertoire in blood and synovial fluid varies with disease activity in early rheumatoid arthritis", *Arthritis Res Ther.*, 10(6):R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", *Lancet*, 364:355-364 (2004).
Robert, et al. "CTLA4 blockade broadens the peripheral T -cell receptor repertoire", Clin Cancer Res., 20(9):2424-32 (2014). doi: 10.1158/1078-0432.CCR-13-2648. Epub Feb. 28, 2014.
Robins et al. "Detecting and monitoring lymphoma with high-throughput sequencing" *Oncotarget*, 2:287-288 (2011).
Robins, et al. "CD4+ and CD8+ T cell β antigen receptors have different and predictable V and J gene usage and CDR3 lengths", *J. Immunol.*, 188: 115.10, Abstract (2012).
Robins, et al. "High-throughput sequencing of T -cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.
Robins, et al. "Overlap of the human CD8+ T cell receptor repertoire." Oct. 2010. Poster. 1 page.

(56) References Cited

OTHER PUBLICATIONS

Robins, et al. "Effects of aging on the human adaptive immune system revealed by high-throughput DNA sequencing of T cell receptors", *J Immunol.*, 188: 47.16, Abstract (2012).
Robins, H. et al. "Digital Genomic Quantification of Tumor Infiltrating Lymphocytes", *Science Translational Medicine*, 5:214ra169, 19 pages, Supplementary Materials (2013).
Robins, H. et al. "The Computational Detection of Functional Nucleotide Sequence Motifs in the Coding Regions of Organisms", *Exp Biol Med*, 233(6): 665-673 (2008).
Robins, H. et al. "Ultra-sensitive detection of rare T cell clones", *Journal of Immunological Methods*, 375(1-2): 14-19 (2012). Epub Sep. 10, 2011.
Robins, H. et al. "Comprehensive assessment of T-cell receptor β-chain diversity in αβ T cells", *Blood*, 114(19):4099-4107 (and Supplemental Materials) (2009).
Robins, H. et al. "Overlap and Effective Size of the Human CD8+ T Cell Receptor Repertoire", *Science Transitional Medicine*, 2(47, 47ra64): and Supplemental Materials, 17 pages (2010).
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Roh, et al., "Comparing microarrays and next-generation sequencing technologies for microbial ecology research." Trends Biotechnol. (Jun. 2010); 28(6): 291-299. Epub Apr. 8, 2010.
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Rothberg, et al. "An integrated semiconductor device enabling non-optical genome sequencing", *Nature*, 475(7356): 348-352 (2011). doi: 10.1038/nature10242.
Rougemont, et al. "Probabilistic base calling of Solexa sequencing data", *BMC Bioinformatics*, 9:431, 12 pages (2008).
Ryan et al. "Clonal evolution of lymphoblastoid cell lines", *Laboratory Investigation*, 86(11):1193-1200 (2006). Epub Oct. 2, 2006.
Saada, R. et al. "Models for antigen receptor gene rearrangement: CDR3 length", *Immunology and Cell Biology*, 85:323-332 (2007).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).
Schlissel, M.S. et al. "Leukemia and lymphoma: a cost of doing business for adaptive immunity", *Genes Dev.*, 20(12): 1539-1544 (2006).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 1 0.1371/journal.pone. 0027310.
Schmitt et al. "Detection of ultra-rare mutations by next-generation sequencing," *PNAS*, 109(36): 14508-14513 and Supporting Information, 9 pages (2012).
Schøller et al. "Analysis of T cell receptor αβ variability in lymphocytes infiltrating melanoma primary tumours and metastatic lesions", *Cancer Immunol Immunother*. 39(4):239-248 (1994).
Schrappe, M. et al. "Late MRD response determines relapse risk overall and in subsets of childhood T-cell ALL: results of the AIEOP-BFM-ALL 2000 study", *Blood*, 118(8): 2077-2084 (2011).
Schreiber et al. "Cancer immunoediting: integrating immunity's roles in cancer suppression and promotion", *Science*, 331(6024): 1565-1570 (2011). doi: 10.1126/science.1203486.
Schwab et al. "CD8+ T-cell clones dominate brain infiltrates in Rasmussen encephalitis and persist in the periphery", *Brain*, 132:1236-1246 (2009).
Schwartzman, Armin. "Empirical null and false discovery rate inference for exponential families." The Annals of Applied Statistics (2008); 2(4): 1332-1359.
Schweiger et al. "Genome-wide massively parallel sequencing of formaldehyde fixed-paraffin embedded (FFPE) tumor tissues for copy-numberr- and mutation-analysis", *PLoS One*, 4(5): e5548, 7 pages (2009). doi: 10.1371/journal.pone.0005548. Epub May 14, 2009.
Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).
Seder and Ahmed, "Similarities and differences in CD4+ and CD8+ effector and memory T cell generation." Nat Immunol. (2003); 4 (9): 835-842.
Sehouli et al. "Epigenetic quantification of tumor-infiltrating T-lymphocytes" *Epigenetics*, 6(2): 236-246 (2011). Epub Feb. 1, 2011.
Seitz, et al. "Reconstitution of paired T cell receptor α- and β-chains from microdissected single cells of human inflammatory tissues", *PNAS*, 103: 12057-12062 (2006).
Seo, et al. "Four-color DNA sequencing by synthesis on a chip using photocleavable fluorescent nucleotides", *PNAS*, 102(17): 5926-5931 (2005). Epub Apr. 13, 2005.
Sfanos et al. "Human Prostate-Infiltrating CD8+ T Lymphocytes are Oligoclonal and PD-1+", *The Prostate*, 69(15): 1694-1703 (2009).
Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.
Shen et al. "Comparing platforms for *C. elegans* mutant identification using high-throughput whole genome sequencing", *PLoS One*, 3(12):e4012, 6 pages (2008).
Shendure and Ji. "Next-generation DNA sequencing", *Nature Biotechnology*, 26(10):1135-1145 (2008).
Shendure, et al. "Advanced sequencing technologies: methods and goals", *Nat Rev Genet.*, 5(5): 335-344 (2004).
Sherwood, A. et al. "Deep Sequencing of the Human TCRγ and TCRβ Repertoires Suggests the TCR β Rearranges After ββ and γδ T Cell Commitment", Science Translational Medicine, *Sci. Transl. Med.*, 3(90): 1-7 (2011).
Sherwood, et al. "New Technologies for Measurements of Tumor Infiltrating Lymphocytes", Presented Nov. 7, 2012 Moscone Center, Exhibit Halls ABC.
sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymghocytes", *The Journal of Heart and Lung Transplant*, 31: 996-1002 (2012).

(56) References Cited

OTHER PUBLICATIONS

Shiroguchi et al. "Digital RNA sequencing minimizes sequence-dependent bias and amplification noise with ogtimized single-molecule barcodes", PNAS, 109(4): 1347-1352 (2012).
Shoemaker et al. "Quantitative phenotypic analysis of yeast deletion mutants using a highly parallel molecular bar-coding strategy," Nature Genetics, 14(4): 450-456 (1996).
Shumaker, et al. "Mutation detection by solid phase primer extension", Hum Mutat., Abstract Only (1996).
Sia, et al. "Microfluidic devices fabricated in poly(dimethylsiloxane) for biological studies", Electrophoresis, 24(21): 3563-3576, Abstract Only (2003).
Sims, et al. "Fluorogenic DNA sequencing in PDMS microreactors", Nat Methods, 8(7): 575-580 (2011). doi: 10.1038/nmeth.1629.
Sims, et al. "MHC-peptide tetramers for the analysis of antigen-specific T cells", Expert Rev Vaccines, 9(7): 765-774 (2010). doi: 10.1586/erv.10.66.
Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", Hepatology, 33(5):1288-1298 (2001).
Singapore Application No. 11201407888R, Written Opinion dated Aug. 14, 2015, 12 pages.
Singapore Application No. 11201500313Y, Search Report and Written Opinion dated Dec. 9, 2015, 11 pages.
Sint, D., et al. "Advances in multiplex PCR: balancing primer efficiencies and improving detection success", Methods in Ecology and Evolution, 3(5): 898-905 (2012).
Skulina et al. "Multiple Sclerosis: Brain-infiltrating CD8+ T cells persist as clonal expansions in the cerebrospinal fluid and blood", PNAS, 101(8):2428-2433 (2004).
Smith et al. "Rapid generation of fully human monoclonal antibodies specific to a vaccinating antigen", Nature Protocols, 4(3): 372-384 and CORRIGENDA (2009).
Smith et al. "Rapid whole-genome mutational profiling using next-generation sequencing technologies", Genome Research, 18: 1638-1642 (2008).
Smith, et al. "Comparison of biosequences", Advances in Applied Mathematics, 2: 482-489 (1981).
Smith, G.P., "Filamentous fusion phage: novel expression vectors that display cloned antigens on the virion surface." Science (Jun. 1985); 228(4705): 1315-1317.
Sobrino, et al. "SNPs in forensic genetics: a review on SNP typing methodologies", Forensic Sci Int., 154(2-3): 181-194, Abstract Only (2005). Epub Jan. 11, 2005.
Sotomayor, et al., "Conversion of tumor-specific CD4+ T-cell tolerance to T-cell priming through in vivo ligation of CD40." Nature Medicine (Jul. 1999); 5(7): 780-787.
Spellman, et al., "Advances in the selection of HLA-compatible donors: refinements in HLA typing and matching over the first 20 years of the National Marrow Donor Program Registry." Biol Blood Marrow Transplant (2008); (9 Suppl):37-44. Epub Jun. 20, 2008.
Spreafico, et al. "A circulating reservoir of pathogenic-like CD4+ T cells shares a genetic and phenotypic signature with the inflamed synovial micro-environment", Ann Rheum Dis., 0: 1-7 (2014). doi: 10.1136/annrheumdis-2014-206226. [Epub ahead of print].
Sramkova, et al. "Detectable minimal residual disease before allogeneic hematopoietic stem cell transplantation predicts extremely poor prognosis in children with acute lymphoblastic leukemia", Pediatr. Blood Cancer, 48(1):93-100 (2007).
Srinivasan et al. "Effect of fixatives and tissue processing on the content and integrity of nucleic acids", Am J Pathol., 161(6): 1961-1971 (2002).
Srivastava and Robins. "Palindromic nucleotide analysis in human T cell receptor rearrangements", PLoS One, 7(12):e52250 (2012). doi: 10.1371/joumal.pone.0052250. Epub Dec. 21, 2012.
Steenbergen, et al. "Distinct ongoing Ig heavy chain rearrangement processes in childhood B-precursor acute lymphoblastic leukemia", Blood, 82(2):581-589 (1993).
Steenbergen, et al. "Frequent ongoing T-cell receptor rearrangements in childhood B-precursor acute lymphoblastic leukemia: implications for monitoring minimal residual disease", Blood, 86(2): 692-702, Abstract Only (1995).
Stemmer, et al. "Single-step assembly of a gene and entire plasmid from large numbers of oligodeoxyribonucleotides", Gene, 164(1): 49-53 (1995).
Steward et al. "A polymerase chain reaction study of the stability of Ig heavy-chain and T-cell receptor delta gene rearrangements between presentation and relapse of childhood B-lineage acute lymphoblastic leukemia", Blood, 83(5):1355-1362 (1994).
Stewart and Schwartz. "Immunoglobulin V regions and the B cell", Blood, 83(7): 1717-1730 (1994).
Stickler, et al. "An in vitro human cell-based assay to rank the relative immunogenicity of proteins", Toxicol Sci., 77(2): 280-289 (2004). Epub Dec. 22, 2003.
Stiller et al. "Direct multiplex sequencing (DMPS)—a novel method for targeted high-throughput sequencing of ancient and highly degraded DNA", Genome Research, 19:1843-849 (2009).
Straten, Perthor, et al. "T-cell clonotypes in cancer", Journal of Translational Medicine, 2(1): 11, 10 pages (2004).
Stratton. "Exploring the genomes of cancer cells: progress and promise", Science, 331(6024): 1553-1558 (2011). doi: 10.1126/science.1204040.
Striebich, et al. "Selective Accumulation of Related CD41 T Cell Clones in the Synovial Fluid of Patients with Rheumatoid Arthritis", J Immunol., 161(8): 4428-4436 (1998).
Struyk et al. "T cell receptors in rheumatoid arthritis", Arthritis & Rheumatism, 38(5):577-589 (1995).
Sumida et al. "T cell receptor repertoire of infiltrating T cells in lips of Sjögren's syndrome patients", J Clin Invest., 89:681-685 (1992).
Sumida et al. "T cell receptor V$\alpha$ repertoire of infiltrating T cells in labial salivary glands from patients with Sjögren's syndrome", J Rheumatol., 21:1655-1661 (1994).
Swarup and Rajeswari. "Circulating (cell-free) nucleic acids—a promising, non-invasive tool for early detection of several human diseases", FEBS Letters, 581(5): 795-799 (2007). Epub Feb. 2, 2007.
Szczepanski et al. "Why and how to quantify minimal residual disease in acute lymphoblastic leukemia?", Leukemia, 21(4):622-626 (2007). Epub Feb. 15, 2007.
Szczepanski et al., "Comparative analysis of Ig and TCR gene rearrangements at diagnosis and at relapse of childhood precursor-B-ALL provides improved strategies for selection of stable PCR targets for monitoring of minimal residual disease", Blood, 99(7):2315-2323 (2002).
Szczepanski, T. et al. "Minimal residual disease in leukemia patients", Lancet Oncology, 2:409-417 (2001).
Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.
Tackenberg et al. "Clonal expansions of CD4+ $\beta$ helper T cells in autoimmune myasthenia gravis", European Journal of Immunology, 37(3):849-863 (2007).
Tajiri et al. "Cell-microarray analysis of antigen-specific B-cells: single cell analysis of antigen receptor expression and specificity", Cytometry Part A, 71A: 961-967 (2007).
Takamatsu, et al., "A comparison between next-generation sequencing and ASO-qPCRfor minimal residual disease detection in multiple myeloma", J. Clin. Oncol., 31(Supplement 1): Abstract 8601 (Conference Abstract), Entire Abstract (2013).
Tam, James P. "Synthetic peptide vaccine design: synthesis and properties of a high-density multiple antigenic peptide system." Proceedings of the National Academy of Sciences (1988); 85.15: 5409-5413.
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", Cancer Research, 70: 6181-6192 (2010).

(56) References Cited

OTHER PUBLICATIONS

Taubenheim et al. "High Rate of Antibody Secretion Is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
Ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Corrigendum: Microdroplet-based PCR enrichment for large-scale targeted sequencing", *Nature Biotechnology*, 28(2):178, 1 page (2010).
Thiel, et al. "Antigen-specific cytometry-new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes A γ Protein Expressed on the Majority of CD3+ T Cell Receptor -a/fr Circulating Lymphocytes", *J. Exp. Med.*, 167:694-699 (1988).
Tsai et al. "Discovery of rare mutations in populations: TILLING by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated May 27, 2011 for UK application No. GB1105068.9.
UK Combined Search Report and Office action dated Jun. 29, 2012 for UK application No. GB1209668.1.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Van Der Velden, V.H.J., et al. "Analysis of minimal residual disease by Ig/TCR gene rearrangements: guidelines for interpretation of real-time quantitative PCR data," *Leukemia*, 21:604-611 (2007).
Van Der Velden, V.H.J., et al. "Detection of minimal residual disease in hematologic malignancies by realtime quantitative PCR: principles, approaches, and laboratory aspects," *Leukemia*, 17:1013-1034 (2003).
Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al. "Design and standardization of PCR primers and protocols for detection of clonal immunoglobulin and I-cell receptor gene recombinations in suspect lymphoproliferations: Report of the BIOMED-2 Concerted Action BMH4-CT98-3936", *Leukemia*, 17:2257-2317 (2003).
Van Dongen, J.J.M. et al. "Prognostic value of minimal residual disease in acute lymphoblastic leukaemia in childhood", *The Lancet*, 352:1731-1738 (1998).
Van Heijst, J.W.J., et al., "Quantitative assessment of T-cell repertoire recovery after hematopoietic stem cell transplantation." Nat Med. (2013); 19(3): 372-377.
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8+ T Cell Responses to Cytomegalovirus and EBV[1]", *The Journal of Immunology*, 181:7853-7862 (2008).
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Wang, et al. "Balanced-PCR amplification allows unbiased identification of genomic copy changes in minute cell and tissue samples", *Nucleic Acids Research*, 32(9): e76, 10 pages (2004).
Wang, et al. "High throughput sequencing reveals a complex pattern of dynamic interrelationships among human T cell subsets", *PNAS*, 107(4): 1518-1528 (2010).
Wang, X. et al. "Quantitative Measurement of Pathogen Specific Human Memory T Cell Repertoire Diversity using a CDR3 B-Specific Microarray", *BMC Genomics*, 8(329): 1-13 (2007).
Warren et al. "Exhaustive T-cell repertoire sequencing of human peripheral blood samples reveals signatures of antigen selection and a directly measured repertoire size of at least 1 million clonotypes", *Genome Res.*, 21(5): 790-797 (2011). Epub Feb. 24, 2011.
Warren et al. "Profiling model T-cell metagenomes with short reads", *Bioinformatics*, 25(4):458-464 (2009).
Weiss et al. "Clonal Rearrangements of T-Cell Receptor Genes in Mycosis Fungoides and Dermatopathic Lymphadenopathy", *The New England Journal of Medicine*, 313(9):539-544 (1985).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).
Wells, et al. "Strategies for preimplantation genetic diagnosis of single gene disorders by DNA amplification", *Prenatal Diagnosis*, 18(13):1389-1401 (1998).
Weng, et al. "Minimal residual disease monitoring with high-throughput sequencing of T cell receptors in cutaneous T cell lymphoma", Sci Transl Med., 5(214):214ra171 (2013).
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).

(56) References Cited

OTHER PUBLICATIONS

Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneous detection using molecular beacons", Nucleic Acids Res., 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor- β Gene Rearrangements." Am J Pathol. (May 2001); 158(5): 1851-1857.
Wilson, et al., "The use of mRNA display to select high-affinity protein-binding peptides." PNAS (Mar. 2001); 98 (7): 3750-3755.
Wilson-Lingardo et al., "Deconvolution of Combinatorial Libraries for Drug Discovery: Experimental Comparison of Pooling Strategies." J. Med. Chem., (1996); 39 (14): 2720-2726.
Wittrup, "Protein engineering by cell-surface display." Current Opinion in Biotechnology (Aug. 2001); 12(4): 395-399.
Wlodarski et al. "Molecular strategies for detection and quantitation of clonal cytotoxic T-cell responses in aplastic anemia and myelodysplastic syndrome", *Blood*, 108(8):2632-2641 (2006).
Wlodarski et al. "Pathologic clonal cytotoxic T-cell responses: nonrandom nature of the T-cell-receptor restriction in large granular lymphocyte leukemia", *Blood*, 106:2769-2779 (2005).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Woodsworth, Daniel J., et al., "Sequence analysis of T-cell repertoires in health and disease." Genome Medicine (2013); 5: 98, 13 pages.
Wrammert et al. "Rapid cloning of high-affinity human monoclonal antibodies against influenza virus", *Nature*, 453: 667-672 (2008).
Wu et al. "Focused Evolution of HIV-1 Neutralizing Antibodies Revealed by Structures and Deep Sequencing", *Science*, 333: 1593-1602 (2011).
Wu, et al. "High-throughput sequencing detects minimal residual disease in acute T lymphoblastic leukemia", Sci Transl Med., 4 (134): 151-17, 134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Wu, Y-C. et al. "High-throughput immunoglobulin repertoire analysis distinguishes between human IgM memory and switched memory B-cell populations", *Blood Journal*, 116(7): 1070-1078, 22 pages (2010).
Xie, Yang, et al., "A note on using permutation-based false discovery rate estimates to compare different analysis methods for microarray data." Bioinformatics (2005); 21.23: 4280-4288.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
XU, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
XU, et al., "Viral immunology. Comprehensive serological profiling of human populations using a synthetic human virome." Science (Jun. 2015); 348(6239):aaa0698.
Xu, W. et al. "A Novel Universal Primer-Multiplex-PCR Method with Sequencing Gel Electrophoresis Analysis", *PLoS One*, 7(1): e22900, 10 pages (2012).
Yagi, et al., "Detection of clonotypic IGH and TCR rearrangements in the neonatal blood spots of infants and children with B-cell precursor acute lymphoblastic leukemia." Blood (2000); 96(1): 264-268.
Yao, et al. "Analysis of the CDR3 length repertoire and the diversity of TCRα chain in human peripheral blood T Lymphocytes", Cell Mol Immunol., 4(3): 215-220 (2007).
Yassai, M.B. et al. "A clonotype nomenclature for T cell receptors", *Immunogenetics*, 61:493-502 (2009).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).
Yonezawa, et al., "DNA display for in vitro selection of diverse peptide libraries." Nucleic Acids Res. (Oct. 2003); 31(19): e118.
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).
Zagnoni, et al. "Droplet Microfluidics for High-throughput Analysis of Cells and Particles", *Methods in Cell Biology*, Chapter 2, 102: 23-48 (2011).
Zaliova, et al. "Quantification of fusion transcript reveals a subgroup with distinct biological properties and predicts relapse in BCR/ABL-positive ALL: implications for residual disease monitoring", *Leukemia*,23(5):944-951(2009).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhong, Q. et al. "Multiplex digital PCR: breaking the one target per color barrier of quantitative PCR", Lab Chip, 11:2167-2174 (2011).
Zhou et al. "High throughput analysis of TCR-β rearrangement and gene expression in single cells", *Laboratory Investigation*, 86: 314-321 (2006).
Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.
Zimmerman and Mannhalter. "Technical aspects of quantitative competitive PCR", *Biotechniques*, 21: 268-279 (1996).

ASSUMING 10 reads per molecule of input (i.e., 10X amplification)

i) {
IF number of unique —————— = 100, THEN 100 unique ——————■—————— = 10X amplification per molecule, 1,000 reads ——————■—————— / 10X amplification per molecule = 1,000

THEREFORE 10,000 
}

AND ii) {
100 unique —————□—————— = 0.1X amplification per molecule,

10 ——————————— / 0.1X amplification per molecule = 10,000

THEREFORE 1,000 
}

THUS, IF  = 1,000

AND  = 10,000

THEN T cells represent 10% of initial sample

US 11,254,980 B1

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: pGEX Forward (GST 5, pGEX 5')

<400> SEQUENCE: 1
gggctggcaa gccacgtttg gtg                                            23

<210> SEQ ID NO 2
<211> LENGTH: 23
<212> TYPE: DNA
<213> ORGANISM: Artificial Sequence
<220> FEATURE:
<223> OTHER INFORMATION: pGEX Reverse (GST 3, pGEX 3')

<400> SEQUENCE: 2
ccgggagctg catgtgtcag agg                                            23
```

METHODS OF PROFILING TARGETED POLYNUCLEOTIDES WHILE MITIGATING SEQUENCING DEPTH REQUIREMENTS

CROSS-REFERENCE TO RELATED APPLICATIONS

This application is a non-provisional application which claims the benefit of priority to U.S. Provisional Application No. 62/592,022, filed Nov. 29, 2017, which is hereby incorporated by reference in its entirety.

CROSS REFERENCE TO SEQUENCE LISTING

The contents of the text file submitted electronically herewith are incorporated herein by reference in their entirety: A computer readable format copy of the Sequence Listing (filename: ADBS_031_02US_SeqList_ST25.txt, date recorded: Oct. 31, 2018, file size 1 kilobyte).

BACKGROUND OF THE INVENTION

The human adaptive immune system provides protection against an enormous variety of pathogens. This protection is mediated by receptors on the surface of B and T cells that bind to pathogenic or pathogen derived antigens. The human germline genome is limited in size, so it cannot code for a sufficient number of receptor genes to protect against the diversity of potential pathogens. The vast receptor diversity needed for protection is created dynamically by somatic rearrangement of the germline DNA at specific loci in B and T cells. Both the B cell receptor (BCR) and T cell receptor (TCR) are formed from pairing of a larger chain and smaller chain. The BCR immunoglobulin heavy chain (IGH) and the TCR beta chain (TCRB) rearrange noncontiguous variable (V), diversity (D), and joining (J) gene segments to create combinatorial diversity. At the junctions between the V-D and D-J, nucleotides are deleted and pseudo-random non-templated nucleotides are added to create massive junctional diversity. The respective small chain, immunoglobulin lambda or kappa (IGL/K) for B cells and T cell receptor alpha (TCRA) for T cells, rearranges similarly, but with V and J only. The set of B and T cells constituting the adaptive immune system are comprised of millions of different clones defined by their specific BCR or TCR sequence rearrangement. The nucleotide sequence of the BCRs and TCRs provide a nearly unique molecular tag for each clone in the adaptive immune system. Moreover, these sequences provide a primary piece of functional information for each clone, as the receptor structures determine their antigenic binding.

The highly variable CDR3 regions in both BCRs and TCRs are short, between 15 and 60 nucleotides, making them amenable to rapid interrogation by high-throughput sequencing (HTS). However, methods designed to sequence large genomic regions do not efficiently apply to these short, highly diverse regions. A new field of immunosequencing has emerged with technologies specifically tailored to sequence BCRs and TCRs, along with a set of promising applications for these technologies [1-4]. As the adaptive immune system is believed to play a role in most, if not all, human disease states, the possible applications are expansive.

There are two primary challenges in HTS of adaptive immune receptors. The first is the somatic rearrangement of the loci. The rearranged BCR and TCR loci are structurally different than in the germline genome. Although there are some known rules that govern the rearrangements, the resultant genes are not minor changes from a known template. Second, the rearranged sequences are highly diverse. The number of clones with different TCRB rearrangements in the blood of a healthy human is estimated to be 1-5 million with total T cell diversity estimated to be 20-100 million [1, 5]. The B cell repertoire diversity is currently unknown, with some lower bound estimates being much larger (>10×) than that of the T cell repertoire. An additional complication in sequencing BCRs is somatic hypermutation. Unlike TCRs, BCRs can evolve to increase antigen binding affinity through a process of point mutation and selection.

Certain groups have employed different methods to sequence both TCR and BCR sequences at high-throughput (Boyd et al., 2010; Wang et al., 2010; Warren et al., 2011; Boyd et al., 2009; Freeman et al., 2009; Weinstein et al., 2009). The inventors have developed high-throughput sequencing methods to sequence millions of adaptive immune receptor chains simultaneously (See Robins et al., 2010; Robins et al., 2009). The strategy accomplishes sequencing at such high volume by using a multiplex PCR method. The nucleotide sequence encoding the TCRβ chain is determined by somatic rearrangement of V, D, and J segments along with a set of non-templated insertions and deletions at the junctions between the V and D, and the D and J segments. A pool of primers to all V and J pairs is used in the multiplex PCR, such that the primers specifically amplify the complete VDJ junction region, known as the CDR3 region, as well as a portion of the J and V segments that is sufficient for identification.

Current immunosequencing techniques include PCR and sequencing steps and produce millions of sequence reads per input sample. The input sample includes multiple amplicons produced from a PCR, and it is advantageous to be able to estimate the absolute number of nucleic acid molecules that are present in the input material for quantitation purposes. However, estimation of the absolute number of input molecules is not a trivial process using sequencing output reads alone. Certain quantitation methods rely on a comparison of the sequencing output of target biological molecules with the sequencing output from a set of uniquely-tagged synthetic control molecules. However, this quantitative comparison requires ultra-deep sequencing of the entire set of molecules (both biological and synthetic molecules) to get an accurate measurement of each unique molecule in the input material. The calculations are only correct insofar as each uniquely-tagged synthetic control molecule in the PCR input is observed with high confidence in the sequencing output. Even using current deep sequencing methods, it is difficult to ensure that each unique control input molecule is observed with high confidence. Deep sequencing methods are also an expensive and time consuming process. Methods are needed to reduce or eliminate this barrier by allowing estimation of the absolute amount of input nucleic acid molecules in an immunosequencing reaction, while performing only a fraction of the sequencing. Such methods would be instrumental not only in quantitatively sequencing adaptive immune receptor genes, but would also be a valuable tool in quantitatively sequencing any biological amplicon produced by a multiplex PCR reaction.

SUMMARY OF THE INVENTION

The methods of the invention address the previously stated concerns by using synthetic molecules that are intended to be directly included in amplification and sequencing reactions of a sample, and whose quantity in the reaction (the exact number of molecules) can be precisely measured to improve the accuracy of multiplex PCR amplification bias correction and absolute input template quantitation, while performing a reduced amount of sequencing compared to other quantitative methods known in the art and alleviating the need for any extrinsic data to guarantee accurate and quantitative results in an efficient and cost effective manner. Amplification bias is described further in International Application No. PCT/US2013/040221, filed on May 8, 2013, which is incorporated by reference in its entirety.

In one aspect, provided herein is a method for quantifying the number of input genomes in a sample, comprising: (A) performing a multiplex polymerase chain reaction (PCR) on a composition comprising: 1) a set of one or more biological nucleotide molecules from a sample obtained from a subject, wherein each biological nucleotide molecule of the one or more biological nucleotide molecules comprises two biological nucleotide sequence priming sites; 2) a set of synthetic nucleotide molecules representing the one or more biological nucleotide molecule, wherein each synthetic nucleotide molecule in the set is represented only once and comprises: (a) a first synthetic nucleotide sequence identical to a biological nucleotide molecule of the one or more biological nucleotide molecules from (A)(1) and comprising the same two biological nucleotide sequence priming sites as the biological nucleotide molecule from the one or more biological nucleotide molecules from (A)(1)); (b) a barcode sequence located between the two biological nucleotide sequence priming sites; (c) a second synthetic nucleotide sequence that is not found in any of the one or more biological nucleotide molecules in (A)(1) and comprising two synthetic nucleotide sequence priming sites; and (d) a random oligonucleotide sequence located between the two synthetic nucleotide sequence priming sites, wherein substantially every synthetic nucleotide molecule from the set of synthetic nucleotide molecules amplified comprises a unique random oligonucleotide sequence; 3) a first set of primers comprising a first adapter sequence and a sequence capable of hybridizing to one of the two biological nucleotide sequence priming sites found in the biological nucleotide molecules of (A)(1) and the first synthetic nucleotide sequence in the set of synthetic nucleotide molecules of (A)(2) and a second set of primers comprising a second adapter sequence or no adapter sequence and a sequence capable of hybridizing to one of the two biological nucleotide sequence priming sites found in the biological nucleotide molecules of (A)(1) and the first synthetic nucleotide sequence in the set of synthetic nucleotide molecules of (A)(2), wherein the first set of primers and the second set of primers are present in equal amounts; and 4) a third set of primers comprising the first adapter sequence and a sequence capable of hybridizing to one of the two synthetic nucleotide sequence priming sites found in the second synthetic nucleotide sequence in the set of synthetic nucleotide molecules of (A)(2), wherein the one or more biological nucleotide molecules in (A)(1) and the set of synthetic nucleotide molecules in (A)(2) are amplified with the first set of primers, the second set of primers, and a third set of primers, thereby producing a plurality of first amplicons comprising the first adapter sequence and a plurality of second amplicons comprising the second adapter sequence; (B) amplifying the plurality of first amplicons in a second PCR using a set of tailing primers, wherein each tailing primer comprises a sequence complementary to the first adapter sequence and a sequencing adapter oligonucleotide sequence to produce a plurality of third amplicons; (C) performing high throughput sequencing of the plurality of third amplicons to produce a plurality of sequence reads; (D) quantifying the total number of input second synthetic nucleotide sequences of (A)(2)(c) in the first PCR by counting the total number of unique random oligonucleotide sequences observed in the sequence reads; (E) determining a sequencing coverage for the plurality of first synthetic nucleotide sequences of (A)(2)(a) by dividing a total number of observed sequence reads containing the barcode by the total number of second synthetic nucleotide sequences obtained in (D); and (F) quantifying the total number of input genomes in the sample by dividing the total number of observed sequence reads of the one or more biological nucleotide molecules in (A)(1) by the sequence coverage determined in (E). In some cases, the sample comprises T cells and/or B cells and provides an estimate of the number of input T cells and/or B cell genomes.

In some cases, the one or more biological nucleotide molecules in step A(1) comprise one or more rearranged CDR3 oligonucleotide sequences from T cells receptor (TCR) loci from T cells and/or Immunoglobulin (Ig) loci from B cells, wherein each CDR3 oligonucleotide sequence comprises a V segment and a J segment. In some cases, the one or more biological nucleotide molecules in step A(1) comprises one or more genomic control regions. In some cases, the one or more genomic control regions are selected from one or more of ACTB, B2M, C1orf34, CHMP2A, GPI, GUSB, HMBS, HPRT1, PSMB4, RPL13A, RPLPO, SDHA, SNRPD3, UBC, VCP, VPS29, PPIA, PSMB2, RAB7A, REEP5 and EMC7. In some cases, the one or more genomic control regions are PSMB2, RAB7A, PPIA, REEP5, and EMC7. In some cases, the random oligonucleotide sequence comprises from 4 to 50 nucleotides. In some cases, the random oligonucleotide sequence comprises 8 nucleotides. In some cases, the second synthetic nucleotide sequence further comprises a spacer between the sequences of (A)(2)(a) and (A)(2)(c). In some cases, the spacer is about 200 base pairs in length. In some cases, the spacer comprises a nucleotide sequence known to have significant secondary structure under typical conditions for PCR.

In some cases, the method further comprises: (G) amplifying by multiplex PCR, sequencing, and quantifying output reads from: (1) an additional set of biological nucleotide molecules comprising rearranged T cell receptor (TCR) loci from T cells or Immunoglobulin (Ig) loci from B cells and (2) an additional set of synthetic nucleotide molecules each comprising one TCR or Ig V segment, one TCR or Ig J or C segment, and a unique barcode which identifies said synthetic template as synthetic, an internal marker oligonucleotide sequence, and a random oligonucleotide sequence, wherein each random oligonucleotide sequence comprises a unique nucleotide sequence, and wherein each synthetic template molecule comprises a unique combination of V and J or C segments; (H) determining an amplification factor for each synthetic nucleotide molecule for the additional set of synthetic nucleotide molecules, wherein the amplification factor is represented by the total number of synthetic nucleotide molecules amplified and sequenced in step (G)(2) as evidenced by the number of sequencing reads from the additional set of synthetic nucleotide molecules divided by the total input number of unique synthetic nucleotide molecules amplified and sequenced in step (G)(2) as evidenced by the number of unique random oligonucleotide sequences observed for the additional set of synthetic nucleotide molecules; and (I) quantifying the total number of T cells or B cells in the sample by dividing the total number of output biological sequences from step (G)(1) as evidenced by the number of sequencing reads obtained from the additional set of biological nucleotide molecules by the corresponding amplification factor from step (H).

In some cases, the sample comprises a mixture of cells comprising T cells and/or B cells and cells that are not T cells and/or B cells. In some cases, the method further comprises determining the ratio of T cells or B cells to genomic control regions in the sample by comparing the total number of T cells or B cells in the sample determined in step (I) to the total number of one or more genomic control regions determined in step (F).

In some cases, the additional set of synthetic templates comprises a sequence of formula I: 5'-U1-B1-V-I-B2-N-J-B3-U2-3', wherein (i) V is an oligonucleotide sequence comprising at least 20 and not more than 1000 contiguous nucleotides of a TCR or Ig variable (V) region encoding gene sequence, or the complement thereof, and each synthetic template comprises a unique V-region oligonucleotide sequence; (ii) J is an oligonucleotide sequence comprising at least 15 and not more than 600 contiguous nucleotides of a TCR or Ig joining (J) region encoding gene sequence, or the complement thereof, and each synthetic template comprises a unique V-region oligonucleotide sequence; (iii) U1 comprises an oligonucleotide sequence that is selected from: (a) a first universal adaptor oligonucleotide sequence, and (b) a first sequencing platform oligonucleotide sequence that is linked to and positioned 5' to a first universal adaptor oligonucleotide sequence; (iv) U2 comprises an oligonucleotide sequence that is selected from: (a) a second universal adaptor oligonucleotide sequence, and (b) a second sequencing platform oligonucleotide sequence that is linked to and positioned 3' to a second universal adaptor oligonucleotide sequence; (v) I is an internal marker oligonucleotide sequence comprising at least 2 and not more than 100 nucleotides; (vi) N is a random oligonucleotide sequence comprising at least 2 and not more than 100 nucleotides; and (vii) B1, B2, and B3 each independently comprise either nothing or an oligonucleotide barcode sequences of at least 2 and not more than 100 nucleotides that uniquely identify, as a pair combination, (a) said unique V region oligonucleotide sequences; and (b) said unique J region oligonucleotide sequences, wherein at least one of B1, B2, and B3 are present in each synthetic template contained in said first set of oligonucleotides. In some cases, the random oligonucleotide sequence comprises at least 4 and not more than 15 nucleotides. In some cases, the random oligonucleotide sequence comprises 8 nucleotides. In some cases, the first adaptor sequence comprises a molecular tag. In some cases, the molecular tag is a mosaic tag.

In another aspect, provided herein is a method for quantifying the number of input genomes in a sample, comprising: (A) amplifying by multiplex polymerase chain reaction (PCR) a composition comprising: 1) one or more biological nucleotide molecules from a sample obtained from a subject, wherein each biological nucleotide molecule of the one or more biological nucleotide molecules comprises two biological nucleotide sequence priming sites; 2) a set of synthetic nucleotide molecules representing the one or more biological nucleotide molecule, wherein each synthetic nucleotide molecule in the set is represented only once and comprises: (a) a first synthetic nucleotide sequence identical to a biological nucleotide molecule of the one or more biological nucleotide molecules from (A)(1) and comprising the same two biological nucleotide sequence priming sites as the biological nucleotide molecule from the one or more biological nucleotide molecules from (A)(1)); (b) a barcode sequence located between the two biological nucleotide sequence priming sites; (c) a second synthetic nucleotide sequence that is not found in any of the one or more biological nucleotide molecules in (A)(1) and comprising two synthetic nucleotide sequence priming sites; and (d) a random oligonucleotide sequence located between the two synthetic nucleotide sequence priming sites, wherein substantially every synthetic nucleotide molecule from the set of synthetic nucleotide molecules amplified comprises a unique random oligonucleotide sequence; 3) a first set of primers comprising a first adapter sequence and a sequence capable of hybridizing to one of the two biological nucleotide sequence priming sites found in the biological nucleotide molecules of (A)(1) and the first synthetic nucleotide sequence in the set of synthetic nucleotide molecules of (A)(2) and a second set of primers comprising a second adapter sequence or no adapter sequence and a sequence capable of hybridizing to one of the two biological nucleotide sequence priming sites found in the biological nucleotide molecules of (A)(1) and the first synthetic nucleotide sequence in the set of synthetic nucleotide molecules of (A)(2), wherein the first set of primers is present at a lower amount than the second set of primers; and 4) a third set of primers comprising the first adapter sequence and a sequence capable of hybridizing to one of the two synthetic nucleotide sequence priming sites found in the second synthetic nucleotide sequence in the set of synthetic nucleotide molecules of (A)(2), wherein the one or more biological nucleotide molecules in (A)(1) and the set of synthetic nucleotide molecules in (A)(2) are amplified with the first set of primers, the second set of primers, and a third set of primers, thereby producing a plurality of first amplicons comprising the first adapter sequence and a plurality of second amplicons comprising the second adapter sequence; (B) amplifying the plurality of first amplicons in a second PCR using a set of tailing primers, wherein each tailing primer comprises a sequence complementary to the first adapter sequence and a sequencing adapter oligonucleotide sequence to produce a plurality of third amplicons; (C) performing high throughput sequencing of the plurality of third amplicons to produce a plurality of sequence reads; (D) quantifying the total number of input second synthetic nucleotide sequences of (A)(2)(c) in the first PCR by counting the total number of unique random oligonucleotide sequences observed in the sequence reads; (E) determining a sequencing coverage for the plurality of first synthetic nucleotide sequences of (A)(2)(a) by dividing a total number of observed sequence reads containing the barcode by the total number of second synthetic nucleotide sequences obtained in (D); and (F) quantifying the total number of input genomes in the sample by dividing the total number of observed sequence reads of the one or more biological nucleotide molecules in (A)(1) by the sequence coverage determined in (E).

In some cases, the first set of primers is present at an amount or concentration 70% lower than the second set of primers. In some cases, the first set of primers is present at an amount or concentration 80% lower than the second set of primers.

In some cases, the sample comprises T cells and/or B cells and provides an estimate of the number of input T cells and/or B cell genomes. In some cases, the one or more biological nucleotide molecules in step A(1) is one or more rearranged CDR3 oligonucleotide sequences from T cells receptor (TCR) loci from T cells and/or Immunoglobulin (Ig) loci from B cells, wherein each CDR3 oligonucleotide sequence comprises a V segment and a J segment. In some cases, the one or more biological nucleotide molecules in step A(1) comprises one or more genomic control regions. In some cases, the one or more genomic control regions are selected from one or more of ACTB, B2M, C1orf34, CHMP2A, GPI, GUSB, HMBS, HPRT1, PSMB4, RPL13A, RPLPO, SDHA, SNRPD3, UBC, VCP, VPS29, PPIA, PSMB2, RAB7A, REEP5 and EMC7. In some cases, the one or more genomic control regions are PSMB2, RAB7A, PPIA, REEP5, and EMC7. In some cases, the random oligonucleotide sequence comprises from 4 to 50 nucleotides. In some cases, the random oligonucleotide sequence comprises 8 nucleotides.

In some cases, the method further comprises: (G) amplifying by multiplex PCR, sequencing, and quantifying output reads from: (1) an additional set of biological nucleotide molecules comprising rearranged T cell receptor (TCR) loci from T cells or Immunoglobulin (Ig) loci from B cells and (2) an additional set of synthetic nucleotide molecules each comprising one TCR or Ig V segment, one TCR or Ig J or C segment, and a unique barcode which identifies said synthetic template as synthetic, an internal marker oligonucleotide sequence, and a random oligonucleotide sequence, wherein each random oligonucleotide sequence comprises a unique nucleotide sequence, and wherein each synthetic template molecule comprises a unique combination of V and J or C segments; (H) determining an amplification factor for each synthetic nucleotide molecule form the additional set of synthetic nucleotide molecules, wherein the amplification factor is represented by the total number of synthetic nucleotide molecules amplified and sequenced in step (G)(2) as evidenced by the number of sequencing reads from the additional set of synthetic nucleotide molecules divided by the total input number of unique synthetic nucleotide molecules amplified and sequenced in step (G)(2) as evidenced by the number of unique random oligonucleotide sequences observed for the additional set of synthetic nucleotide molecules; and (I) quantifying the total number of T cells or B cells in the sample by dividing the total number of output biological sequences from step (G)(1) as evidenced by the number of sequencing reads obtained from the additional set of biological nucleotide molecules by the corresponding amplification factor from step (H). In some cases, the sample comprises a mixture of cells comprising T cells and/or B cells and cells that are not T cells and/or B cells. In some cases, the method further comprises determining the ratio of T cells or B cells to genomic control regions in the sample by comparing the total number of T cells or B cells in the sample determined in step (I) to the total number of one or more genomic control regions determined in step (F).

In some cases, the additional set of synthetic templates comprises a sequence of formula I: 5'-U1-B1-V-I-B2-N-J-B3-U2-3', wherein (i) V is an oligonucleotide sequence comprising at least 20 and not more than 1000 contiguous nucleotides of a TCR or Ig variable (V) region encoding gene sequence, or the complement thereof, and each synthetic template comprises a unique V-region oligonucleotide sequence; (ii) J is an oligonucleotide sequence comprising at least 15 and not more than 600 contiguous nucleotides of a TCR or Ig joining (J) region encoding gene sequence, or the complement thereof, and each synthetic template comprises a unique V-region oligonucleotide sequence; (iii) U1 comprises an oligonucleotide sequence that is selected from: (a) a first universal adaptor oligonucleotide sequence, and (b) a first sequencing platform oligonucleotide sequence that is linked to and positioned 5' to a first universal adaptor oligonucleotide sequence; (iv) U2 comprises an oligonucleotide sequence that is selected from: (a) a second universal adaptor oligonucleotide sequence, and (b) a second sequencing platform oligonucleotide sequence that is linked to and positioned 3' to a second universal adaptor oligonucleotide sequence; (v) I is an internal marker oligonucleotide sequence comprising at least 2 and not more than 100 nucleotides; (vi) N is a random oligonucleotide sequence comprising at least 2 and not more than 100 nucleotides; and (vii) B1, B2, and B3 each independently comprise either nothing or an oligonucleotide barcode sequences of at least 2 and not more than 100 nucleotides that uniquely identify, as a pair combination, (a) said unique V region oligonucleotide sequences; and (b) said unique J region oligonucleotide sequences, wherein at least one of B1, B2, and B3 are present in each synthetic template contained in said first set of oligonucleotides. In some cases, the random oligonucleotide sequence comprises at least 4 and not more than 15 nucleotides. In some cases, the random oligonucleotide sequence comprises 8 nucleotides. In some cases, the first adaptor sequence comprises a molecular tag. In some cases, the molecular tag is a mosaic tag.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 3 illustrates the number of estimated templates using all templates (no down-sampling) compared with the number of estimated templates using 30% of the primers with the correct adaptor sequence (0.09-counter; diamonds) or using 20% of the primers with the correct adaptor sequence (0.04-counter; squares). The linear correlation shows that sampling only 30% or 20% of the input synthetic HKG molecules provides an accurate estimation of the total input genome molecules, similar to the estimated number of input genomes from sequencing all of the synthetic HKG molecules in the sample.

FIG. 4 shows the number of estimated templates (X-axis) compared with the number of estimated templates using 20% of the primers with the correct adaptor sequence for each experiment (run 1, run 2, run 3). Each experiment used a separate set of DNA and a separate PCR and sequencing setup. The linear correlation shows that sampling only 20% of the input synthetic and biologic HKG molecules provides an accurate estimation of the total input genome molecules, similar to the estimated number of input genomes from sequencing all of the synthetic HKG molecules in the sample.

DETAILED DESCRIPTION OF THE INVENTION

Figure 1A:
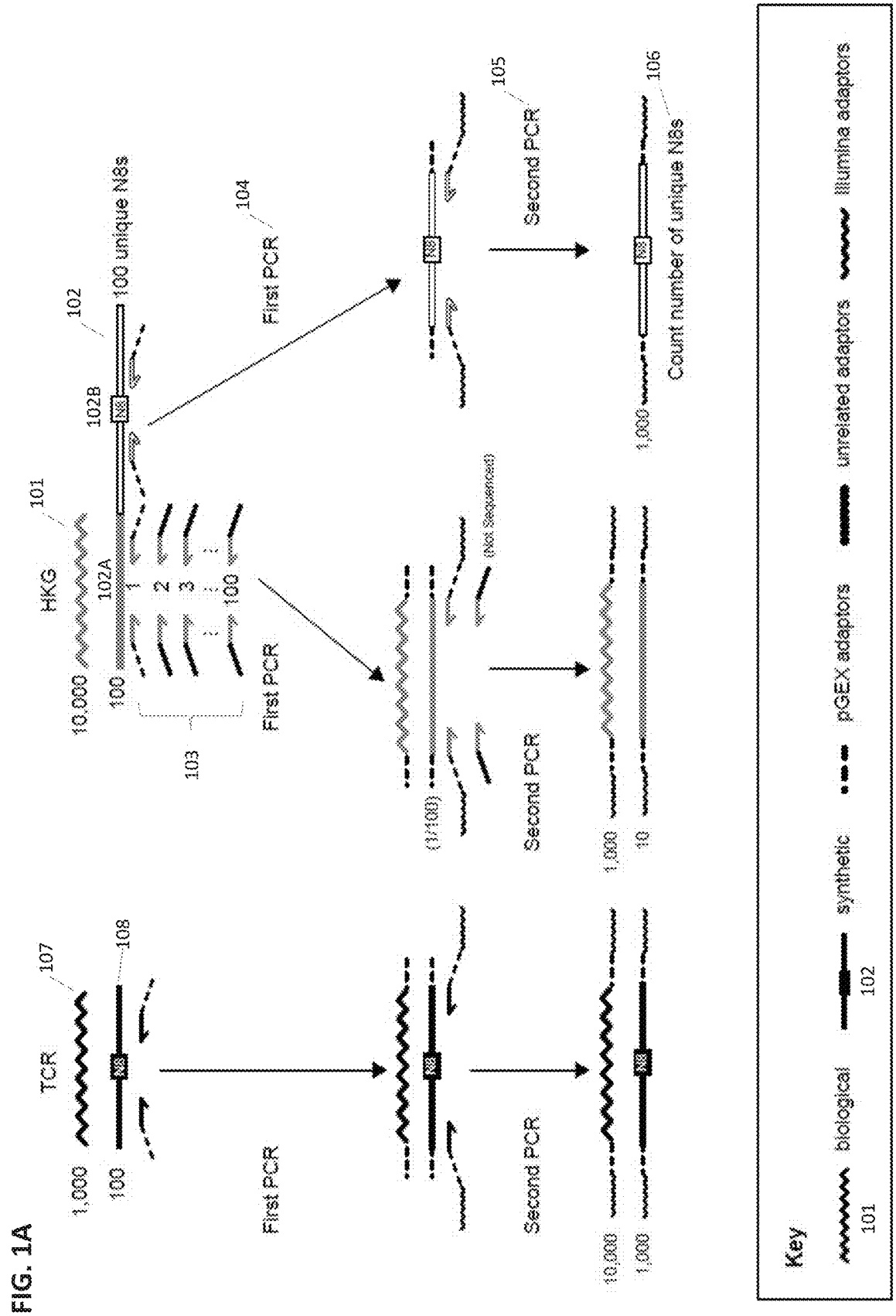
FIG. 1A illustrates an embodiment of the amplification steps of the method.

The practice of the present invention may employ, unless otherwise indicated, conventional techniques, nomenclature and descriptions of protein chemistry, analytical chemistry, synthetic organic chemistry, medicinal and pharmaceutical chemistry, molecular biology (including recombinant techniques), pharmacology, bioinformatics, cell biology, and biochemistry, which are within the skill of the art. Such conventional or standard techniques include, but are not limited to, sampling and analysis of blood cells, nucleic acid sequencing and analysis, and the like. Specific illustrations of suitable techniques can be had by reference to the examples herein below. However, other equivalent conventional procedures can, of course, also be used. Such conventional techniques and descriptions are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

While the compositions and methods described herein are exemplified using adaptive immune receptor genes as the biological template, the skilled artisan will readily understand that the method and compositions of the current invention can be used in any multiplex PCR/HTS methods regardless of the template.

General Terminology

While the following terms are believed to be well understood by one of ordinary skill in the art, the following definitions are set forth to facilitate explanation of the presently disclosed subject matter.

As used herein, the singular forms "a", "an" and "the" are intended to include the plural forms as well, unless the context clearly indicates otherwise. Additionally, the use of "or" is intended to include "and/or" unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" as used herein can refer to a range that is 15%, 10%, 8%, 6%, 4%, or 2% plus or minus from a stated numerical value. In other embodiments, the terms "about" or "approximately" when preceding a numerical value indicates the value plus or minus a range of 10%, 11%, 12%, 13% or 14%, or greater, etc. In yet other embodiments, the terms "about" or "approximately" when preceding a numerical value indicates the value plus or minus a range of 15%, 16%, 17%, 18%, 19% or 20%, or greater, etc.

Unless the context requires otherwise, throughout the present specification and claims, the word "comprise" and variations thereof, such as, "comprises" and "comprising" are to be construed in an open, inclusive sense that is as "including, but not limited to". As used herein, the terms "include," "have" and "comprise" are used synonymously, which terms and variants thereof are intended to be construed as non-limiting. By "consisting of" is meant including, and typically limited to, whatever follows the phrase "consisting of" By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and can or cannot be present depending upon whether or not they affect the activity or action of the listed elements.

Reference throughout this specification to "one embodiment" or "an embodiment" or "an aspect" means that a particular feature, structure or characteristic described in connection with the embodiment may be included in at least one embodiment of the present disclosure. Thus, the appearances of the phrases "in one embodiment" or "in an embodiment" in various places throughout this specification may not necessarily all referring to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

As used herein, an adaptive immune receptor (AIR) refers to an immune cell receptor, e.g., a T cell receptor (TCR) or a B cell receptor (BCR) found in mammalian cells. In certain embodiments, the adaptive immune receptor is encoded by a TCRB, TCRG, TCRA, TCRD, IGH, IGK, and IGL gene or gene segment.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers can have a length in the range of 14 to 40 nucleotides, or in the range of 18 to 36 nucleotides, for example. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

As used herein, the term "universal tag" also referred to as a "universal region" refers to a region of an oligonucleotide primer that has no significant homology to any segment in the genome and is localized to the 5' end of the oligonucleotide primer. The universal tag meets all the requirements for a normal oligonucleotide primer, such as lack of secondary structure, an appropriate tm, and an appropriate GC content. The "universal priming site" as used herein refers to a universal tag of a primer that may function as a site to which universal primers anneal for priming of further cycles of DNA amplification. The universal tags are heterologous to the sequences to which they will be incorporated with through PCR.

In some embodiments, as used herein, the term "gene" refers to the segment of DNA involved in producing a polypeptide chain, such as all or a portion of a TCR or Ig polypeptide (e.g., a CDR3-containing polypeptide); it includes regions preceding and following the coding region "leader and trailer" as well as intervening sequences (introns) between individual coding segments (exons), regulatory elements (e.g., promoters, enhancers, repressor binding sites and the like), or recombination signal sequences (RSSs), as described herein.

The nucleic acids of the present embodiments, also referred to herein as polynucleotides, and including oligonucleotides, can be in the form of RNA or in the form of DNA, including cDNA, genomic DNA, and synthetic DNA. The DNA can be double-stranded or single-stranded, and if single stranded, can be the coding strand or non-coding (anti-sense) strand. A coding sequence which encodes a TCR or an IG or a region thereof (e.g., a V region, a D segment, a J region, a C region, etc.) for use according to the present embodiments can be identical to the coding sequence known in the art for any given TCR or immunoglobulin gene regions or polypeptide domains (e.g., V-region domains, CDR3 domains, etc.), or can be a different coding sequence, which as a result of the redundancy or degeneracy of the genetic code, encodes the same TCR or immunoglobulin region or polypeptide.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al., U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al., U.S. Pat. No. 5,210,015 ("tagman"); Wittwer et al., U.S. Pat. Nos. 6,174,670 and 6,569,627 (intercalating dyes); Tyagi et al., U.S. Pat. No. 5,925,517 (molecular beacons); which are incorporated herein by reference. Detection chemistries for real-time PCR are reviewed in Mackay et al., Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" refers to a PCR wherein multiple target sequences (or a single target sequence and one or more reference sequences) are simultaneously carried out in the same reaction mixture, e.g. Bernard et al., Anal. Biochem., 273: 221-228 (1999)(two-color real-time PCR). Usually, distinct sets of primers are employed for each sequence being amplified. Typically, the number of target sequences in a multiplex PCR is in the range of 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, 02-microglobulin, ribosomal RNA, and the like. Techniques for quantitative PCR are well-known to those of ordinary skill in the art, as exemplified in the following references that are incorporated by reference: Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989); and the like.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

"Activation" or "immune activation" or "activated", especially in reference to T-cells, means a phase of an adaptive immune response that follows the antigen recognition phase (during which antigen-specific lymphocytes bind to antigens) and is characterized by proliferation of lymphocytes and their differentiation into effector cells, e.g. Abbas et al., Cellular and Molecular Immunology, Fourth Edition, (W.B. Saunders Company, 2000). Activation of T cells may be associated with secretion of certain cytokines that are detectable using conventional assays, such as an ELISPOT assay, and may be associated with the expression of characteristic cell surface markers, such as CD25, CD134, CD69, CD137, CD154, or the like, e.g. Gratama et al., Cytometry A, 73A: 971-974 (2008).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction. That is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al., U.S. Pat. Nos. 4,683,195; 4,965,188; 4,683,202; 4,800,159 (PCR); Gelfand et al., U.S. Pat. No. 5,210,015 (real-time PCR with "taqman" probes); Wittwer et al, U.S. Pat. No. 6,174,670; Kacian et al., U.S. Pat. No. 5,399,491 ("NASBA"); Lizardi, U.S. Pat. No. 5,854,033; Aono et al., Japanese Patent Pub. No. JP 4-262799 (rolling circle amplification); and the like.

In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonotype" or "clone" means a rearranged or recombined nucleotide sequence of a lymphocyte which encodes an immune receptor or a portion thereof. More particularly, clonotype means a recombined nucleotide sequence of a T cell or B cell which encodes a T cell receptor (TCR) or B cell receptor (BCR), or a portion thereof. In various embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, a VD rearrangement of TCR δ, a Kde-V rearrangement, or the like. Clonotypes may also encode translocation breakpoint regions involving immune receptor genes, such as Bcl1-IgH or Bcl1-IgH. In one aspect, clonotypes have sequences that are sufficiently long to represent or reflect the diversity of the immune molecules that they are derived from; consequently, clonotypes may vary widely in length. In some embodiments, clonotypes have lengths in the range of from 25 to 400 nucleotides; in other embodiments, clonotypes have lengths in the range of from 25 to 200 nucleotides.

"Clonotype profile" means a listing of distinct clonotypes and their relative abundances that are derived from a population of lymphocytes. The population of lymphocytes can be obtained from a tissue sample or a blood sample. The term "clonotype profile" is related to, but more general than, the immunology concept of an immune "repertoire" as described in references, such as the following: Arstila et al, Science, 286: 958-961 (1999); Yassai et al, Immunogenetics, 61: 493-502 (2009); Kedzierska et al, Mol. Immunol., 45(3): 607-618 (2008); and the like. The term "clonotype profile" includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversity as compared to full immune receptors. In some embodiments, clonotype profiles may comprise abundances or relative frequencies of each of the distinct clonotypes. Another measure of a clonotype profile is the clonality, which is a measurement of the diversity of the clonotypes. In one aspect, a clonotype profile is a set of distinct recombined nucleotide sequences (with their abundances) that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, nucleic acid segments defining clonotypes are selected so that their diversity (i.e. the number of distinct nucleic acid sequences in the set) is large enough so that substantially every T cell or B cell or clone thereof in an individual carries a unique nucleic acid sequence of such repertoire. That is, preferably each different clone of a sample has different clonotype. In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a clonotype profile comprising human TCR R chains or fragments thereof comprises a number of distinct nucleotide sequences in the range of from $0.1\times10^6$ to $1.8\times10^6$, or in the range of from $0.5\times10^6$ to $1.5\times10^6$, or in the range of from $0.8\times10^6$ to $1.2\times10^6$. In another embodiment, a clonotype profile comprising human IgH chains or fragments thereof comprises a number of distinct nucleotide sequences in the range of from $0.1\times10^6$ to $1.8\times10^6$, or in the range of from $0.5\times10^6$ to $1.5\times10^6$, or in the range of from $0.8\times10^6$ to $1.2\times10^6$. In a particular embodiment, a clonotype profile of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher. "Substantially all" can also mean at least 80%, 85%, 90%, 95%, 96%, 97%, 98%, 99% or 100% of the unique clones found in a sample. In another particular embodiment, a clonotype profile of the invention comprises a set of nucleotide sequences that encodes substantially all segments of the V(D)J region of a TCR R chain. In another embodiment, a clonotype profile of the invention comprises a set of nucleotide sequences having lengths in the range of from 25-600 nucleotides and including segments of the V, D, and J regions of a TCR R chain. In another embodiment, a clonotype profile of the invention comprises a set of nucleotide sequences having lengths in the range of from 25-600 nucleotides and including segments of the V, D, and J regions of an IgH chain. In another embodiment, a clonotype profile of the invention comprises a number of distinct nucleotide sequences that is substantially equivalent to the number of lymphocytes expressing a distinct IgH chain. In another embodiment, a clonotype profile of the invention comprises a number of distinct nucleotide sequences that is substantially equivalent to the number of lymphocytes expressing a distinct TCR R chain. In still another embodiment, "substantially equivalent" means that with ninety-nine percent probability, a clonotype profile will include a nucleotide sequence encoding an IgH or TCR R or portion thereof carried or expressed by every lymphocyte of a population of an individual at a frequency of 0.001 percent or greater. In still another embodiment, "substantially equivalent" means that with ninety-nine percent probability, a repertoire of nucleotide sequences will include a nucleotide sequence encoding an IgH or TCR R or portion thereof carried or expressed by every lymphocyte present at a frequency of 0.0001 percent or greater.

"Coalescing" or "clustering" means treating two candidate clonotypes with sequence differences as the same by determining that such differences are due to experimental or measurement error and not due to genuine biological differences. In one aspect, a sequence of a higher frequency candidate clonotype is compared to that of a lower frequency candidate clonotype and if predetermined criteria are satisfied then the number of lower frequency candidate clonotypes is added to that of the higher frequency candidate clonotype and the lower frequency candidate clonotype is thereafter disregarded. That is, the read counts associated with the lower frequency candidate clonotype are added to those of the higher frequency candidate clonotype.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

The term "in situ" refers to processes that occur in a living cell growing separate from a living organism, e.g., growing in tissue culture.

The term "in vivo" refers to processes that occur in a living organism.

The term "mammal" as used herein includes but is not limited to humans, non-human primates, canines, felines, murines, bovines, equines, and porcines.

Overview

Provided herein are methods and compositions for quantifying the amount of target nucleic acid in a sample. In some cases, provided herein is a method for determining an absolute number of input target nucleic acid molecules in a sequencing reaction using a fraction of the sequence reads or ultra-deep sequencing that is required in previous sequencing techniques. The methods and compositions can utilize 1) synthetic templates representing one or more target nucleic acids (synthetic target oligonucleotides), 2) synthetic templates representing one or more control genes (synthetic control gene oligonucleotides), 3) as well as primer sets directed toward a) the one or more target nucleic acids, b) the synthetic templates representing the one or more target nucleic acids (synthetic target oligonucleotides), c) the one or more control genes and/or d) the synthetic templates representing the one or more control genes (synthetic control gene oligonucleotides). The one or more target nucleic acids can be any target nucleic acid provided herein such as, for example, any or all rearranged adaptive immune receptor (AIR) sequences. The one or more control genes can be one or more housekeeping genes (HKGs). The one or more HKGs can be any housekeeping gene provided herein. The sample from which the one or more target nucleic acids are derived or extracted can be any sample provided herein.

Overall any synthetic template provided herein can include primer-annealing sites and a sequence tag identifying the template as synthetic. Further, the primer pairs for amplifying the genomic region and the synthetic templates can do so with the same efficacy, resulting in a mixed library that includes amplicons of both the synthetic and biologic templates. Synthetic templates are described further in International Pub. No. WO2013169957, filed on May 8, 2013, U.S. Ser. No. 61/644,294, filed on May 8, 2012, U.S. Ser. No. 61/726,489, filed on Nov. 14, 2012, which are each incorporated by reference in its entirety.

The methods and compositions can entail utilizing amplification reaction(s) in combination with sequencing reactions in order to generate sequence reads for the one or more target nucleic acids, the synthetic templates representing the one or more target nucleic acids (synthetic target oligonucleotides), the one or more control genes and/or the synthetic templates representing the one or more control genes (synthetic control gene oligonucleotides) and utilizing said sequence reads to determine the amount of the one or more target nucleic acids in a sample from which the one or more target nucleic acids originated. The number of sequence reads of 1) the one or more target nucleic acids, 2) the synthetic templates representing the one or more target nucleic acids, 3) the one or more control genes and/or 4) the synthetic templates representing the one or more control genes templates necessary to determine or quantify the amount of the one or more target nucleic acids in a sample can be a fraction of or a lower % of the number of said sequencing reads needed using sequencing techniques known in the art. In some embodiments, the number of sequence reads generated from the synthetic templates representing the one or more control genes (synthetic control gene oligonucleotides) are a fraction of or a lower % of the number of said sequencing reads produced from the other biological and synthetic templates. The generation of the fraction of or lower % of sequencing reads can be achieved by subjecting a lower number of amplicons to sequencing. The lower number of amplicons can be generated as provided herein such as, for example, by lowering the concentration of specific primer pairs or sets of primers pairs during one or more PCR steps utilized in the method provided herein or through the use of primers or sets of primers that have a reduced affinity for the sequence to which said primer or set of primers are directed.

Designing pairs of primers to amplify conserved regions of the genome or cDNA are understood by one of skill in the art (e.g., those trained in molecular biology). Specifically, an optimal primer pair amplifies a conserved region of the genome, specifically avoiding regions that have common single nucleotide polymorphisms and copy number variants. Additionally, researchers may desire primers to amplify one region of the genome, but as long as the primer pairs consistently amplify the same number of regions whether one or two or three, the assay can work. One of skill in the art would use skill and published literature to identify possible regions to target and verify if designed primers meet requirements by using commonly used resources like the UCSC genome browser (genome.ucsc.edu/) or Primer BLAST (www.ncbi.nlm.nih.gov/tools/primer-blast/). In addition, the primer pairs should amplify a region of the genome that is approximately the same size as the region of interest. For example, as shown herein, a region of interest in the CDR3 regions of rearranged TRB chains can be targeted. This region of interest is only carried by T lymphocytes, not all cell types. Description about designing V-segment and J-segment primers for amplifying CDR3 regions is found in U.S. Ser. No. 12/794,507 and U.S. Ser. No. 13/217,126, which are each incorporated by reference in its entirety.

Further provided herein are compositions and methods that are useful for reliably quantifying and determining the sequences of large and structurally diverse populations of rearranged genes encoding adaptive immune receptors (AIRs), such as immunoglobulins (IG) and/or T cell receptors (TCR). These rearranged genes may be present in a biological sample containing DNA from lymphoid cells of a subject or biological source, including a human subject, and/or mRNA transcripts of these rearranged genes may be present in such a sample and used as templates for cDNA synthesis by reverse transcription.

Methods are provided for quantifying an amount of synthetic template oligonucleotides (e.g., synthetic target oligonucleotides or synthetic control gene oligonucleotides) in a sample to determine a total number of input genomes from adaptive immune cells in a biological sample. In one embodiment, a sample of synthetic template oligonucleotides (e.g., synthetic target oligonucleotides or synthetic control gene oligonucleotides) is used to determine a ratio of the number of input synthetic template oligonucleotide molecules (e.g., synthetic target oligonucleotides or synthetic control gene oligonucleotides) compared with the number of total output (amplicon) synthetic template oligonucleotides (e.g., synthetic target oligonucleotides or synthetic control gene oligonucleotides). A limiting dilution of this sample is spiked-in to a biological sample (at the start of a multiplex PCR assay) and used to determine the total number of input genomes from adaptive immune cells in the biological sample. In certain embodiments, the synthetic templates in the sample comprise a stretch of random nucleic acids, for example an 8 nucleotide randomer. Therefore, limiting dilutions can be made such that each synthetic template in the sample is present only once and can be identified by the 8 nucleotide randomer contained therein. The invention is not limited by the use of an 8 nucleotide randomer, however. Randomers of various lengths, for example 4-15, or more nucleotides may be used in accordance with the methods of the current invention. The use of limiting dilutions in the methods provided herein can closely mirror the use of limiting dilutions found in WO2015/134787, the contents of which are herein incorporated by reference in their entirety.

The methods provided herein also includes determining the relative representation of adaptive immune cells in a sample that contains a mixture of cells, where the mixture comprises adaptive immune cells and cells that are not adaptive immune cells. In certain embodiments, a relative representation of DNA from adaptive immune cells (e.g., T and/or B lymphocytes having rearranged adaptive immune receptor genes, including T- and B-lineage cells of different maturational stages such as precursors, blast cells, progeny or the like) among total DNA from a sample of mixed cell types can be quantified. For instance, certain embodiments permit determination, in DNA extracted from a biological sample, of the relative representation of DNA from tumor infiltrating lymphocytes (TIL) in the DNA from the biological sample, where the sample comprises all or a portion of a tumor that contains adaptive immune cells and cells that are not adaptive immune cells (including tumor cells). Certain other embodiments, for example, permit determination, in DNA extracted from a biological sample, of the relative representation of DNA from infiltrating lymphocytes in the DNA from the biological sample, where the sample comprises all or a portion of a somatic tissue that contains adaptive immune cells and cells that are not adaptive immune cells, such as cells of a solid tissue. Alternative methods of quantifying the relative representation of adaptive immune cells in a mixture of cells are disclosed in U.S. Ser. No. 13/656,265, filed on Oct. 21, 2012, and International App. No. PCT/US2012/061193, filed on Oct. 21, 2012, which are hereby incorporated by reference in their entireties.

The cells in the mixture of cells may not all be adaptive immune cells, and certain unforeseen advantages of the herein described embodiments are obtained where the cells in the mixture of cells need not all be adaptive immune cells. As described herein, compositions and methods are provided for quantifying the proportion of cellular genomes in a sample comprising nucleic acid molecules (e.g., DNA) that are contributed by adaptive immune cells relative to the total number of cellular genomes in the sample, starting from a DNA sample that has been extracted from a mixture of cell types, such as a solid tumor or a solid tissue.

In certain embodiments, rearranged adaptive immune receptor nucleic acid molecules are amplified in a single multiplex PCR using rearranged adaptive immune receptor-specific oligonucleotide primer sets to produce adaptive immune cell-specific DNA sequences, which are used to determine the relative contribution of adaptive immune cells as compared to the total DNA extracted from a sample of mixed cell types. In other embodiments, rearranged adaptive immune cell mRNA molecules are amplified using rt-qPCR and rearranged adaptive immune receptor-specific oligonucleotide primer sets to quantify rearranged adaptive immune receptor cDNA signals and to determine the relative contribution of adaptive immune cells to the total number of genomes extracted from a sample of mixed cell types. Methods of using qPCR to determine the relative representation of adaptive immune cells in a mixture of cells are disclosed in U.S. Ser. No. 13/656,265, filed on Oct. 21, 2012, and International App. No. PCT/US2012/061193, filed on Oct. 21, 2012, which are hereby incorporated by reference in their entireties.

Furthermore, in other embodiments, where the sample includes mRNA molecules, methods of the invention include using a real time quantitative polymerase chain reaction (qPCR) assay with oligonucleotide primer sets that specifically amplify substantially all rearranged adaptive immune receptor genes (e.g., CDR3 encoding polynucleotide-containing portions of rearranged T cell receptor and/or immunoglobulin genes) that may be present in a sample, to generate a first detectable DNA signal that quantitatively reflects the production of a multiplicity of amplified rearranged adaptive immune receptor encoding DNA molecules. In certain embodiments, qPCR amplification may be monitored at one or a plurality of time points during the course of the qPCR reaction, i.e., in "real time". Real-time monitoring permits determination of the quantity of DNA that is being generated by comparing a so-measured adaptive immune receptor-encoding DNA-quantifying signal to an appropriate synthetic template (or control template DNA) quantifying signal, which may be used as a calibration standard. Methods for quantification using qPCR are described in detail in U.S. application Ser. No. 13/656,265, filed on Oct. 21, 2012, International App. No. PCT/US2012/061193, filed on Oct. 21, 2012, which are each incorporated by reference in their entireties.

Further disclosed herein are unexpectedly advantageous approaches for determining the relative representation of adaptive immune cells in a biological sample using multiplex PCR to generate a population of amplified DNA molecules from a biological sample containing rearranged genes encoding adaptive immune receptors, prior to quantitative high throughput sequencing of such amplified products. Multiplexed amplification and high throughput sequencing of rearranged TCR and BCR (IG) encoding DNA sequences are described, for example, in Robins et al., 2009 Blood 114, 4099; Robins et al., 2010 Sci. Translat. Med. 2:47ra64; Robins et al., 2011 J. Immunol. Meth. doi:10.1016/j.jim.2011.09. 001; Sherwood et al. 2011 Sci. Translat. Med. 3:90ra61; U.S. Ser. No. 13/217,126 (US Pub. No. 2012/0058902), U.S. Ser. No. 12/794,507 (US Pub. No. 2010/0330571), WO/2010/151416, WO/2011/106738 (PCT/US2011/026373), WO2012/027503 (PCT/US2011/049012), U.S. Ser. No. 61/550,311, WO/2013/169957 (PCT/US2013/040221), WO/2013/188831 (PCT/US2013/045994), and U.S. Ser. No. 61/569,118; accordingly these disclosures are incorporated by reference and may be adapted for use according to the embodiments described herein.

Further described herein, in certain embodiments, are compositions and methods for the use of synthetic template oligonucleotides (e.g., synthetic target oligonucleotides or synthetic control gene oligonucleotides) that are intended to be directly included in amplification and sequencing reactions of a sample, and whose quantity in the reaction (the number of molecules) can be precisely measured to improve the accuracy of multiplex PCR amplification bias correction and absolute input template quantitation. Amplification bias is described further in WO/2013/169957 (PCT/US2013/040221) and Carlson, C. S. et al. Using synthetic templates to design an unbiased multiplex PCR assay, Nature Communications 4, 2680, doi: 10.1038/ncomms3680 (2013), both of which are each incorporated by reference in its entirety.

The present invention is directed in certain embodiments as described herein to quantification of DNA from adaptive immune cells that are present in solid tissues, and in particular embodiments, to solid tumors, such that the relative presence of adaptive immune cells as a proportion of all cell types that may be present in the tissue (e.g., tumor) can be determined. These oligonucleotide primer sets used in the methods and compositions provided herein permit production of amplified rearranged DNA molecules and synthetic template molecules that encode portions of adaptive immune receptors as well as control genes and synthetic control gene templates. These and related embodiments feature the selection of a plurality of oligonucleotide primers that specifically hybridize to adaptive immune receptor (e.g., T cell receptor, TCR; or immunoglobulin, Ig) V-region polypeptide encoding polynucleotide sequences and J-region polypeptide encoding polynucleotide sequences. The invention includes universal primers that are specific to universal adaptor sequences and bind to amplicons comprising universal adaptor sequences. The primers promote PCR amplification of nucleic acid molecules, such as DNA, that include substantially all rearranged TCR CDR3-encoding or Ig CDR3-encoding gene regions that may be present in a test biological sample, where the sample contains a mixture of cells which comprises adaptive immune cells (e.g., T- and B-lymphocyte lineage cells) and cells that are not adaptive immune cells. For example, a cell mixture may be obtained from a solid tumor that comprises tumor cells and TILs.

The compositions provided herein can comprise (1) a set of one or more biological nucleotide molecules from a sample obtained from a subject, such that each biological nucleotide molecule comprises two biological nucleotide sequence priming sites; (2) a first set of synthetic nucleotide molecules representing the one or more biological nucleotide molecules, wherein each unique sequence of the synthetic nucleotide molecules in the set is represented only once and generally comprises: (a) a first synthetic nucleotide sequence identical to a biological nucleotide molecule of the one or more biological nucleotide molecules from (1) and comprising the same two biological nucleotide sequence priming sites as the biological nucleotide molecule from the one or more biological nucleotide molecules from (1); (b) a second synthetic nucleotide sequence that is not found in any of the one or more biological nucleotide molecules in (1) and comprising two synthetic nucleotide sequence priming sites and (c) optionally, a random oligonucleotide sequence that identifies the molecule as synthetic The compositions provided herein can further comprise (A) a first set of primers comprising a first adapter sequence and a sequence capable of hybridizing to one of the two biological nucleotide sequence priming sites found in the set of biological nucleotide molecules of (1) and the first synthetic nucleotide sequence in the set of synthetic nucleotide molecules of (2); (B) a second set of primers comprising a second adapter sequence or no adapter sequence and a sequence capable of hybridizing to the same one of said two biological nucleotide sequence priming sites found in the biological nucleotide molecules of (1) and the first synthetic nucleotide sequence in the set of synthetic nucleotide molecules of (2) as the first set of primers; and (4) a third set of primers comprising the first adapter sequence and a sequence capable of hybridizing to one of the two synthetic nucleotide sequence priming sites found in the second synthetic nucleotide sequence in the set of synthetic nucleotide molecules of (2). In some cases, the first set of primers and the second set of primers are present in equal amounts, concentrations or percentages. In some cases, the first set of primers is present at a lower amount, concentration or percentage than the second set and/or third set of primers. In some cases, the first set of primers bind to the one of said two biological nucleotide sequence priming sites at a lower affinity than the second set or primers. In preferred embodiments, the third set of primers each comprise the first adaptor sequence that is the same as the adaptor sequence found in the first set of primers. In certain embodiments, each of the first set of primer pairs and/or third set of primer pairs comprise the first adaptor sequence at the 5' ends of the primer, while the second set of primer pairs comprise the second adapter sequence at the 5' ends of the primer.

The synthetic templates (e.g., synthetic target oligonucleotides or synthetic control gene oligonucleotides) can have any structure as provided herein. In some cases, the synthetic templates (e.g., synthetic target oligonucleotides or synthetic control gene oligonucleotides) can further comprise a barcode sequence as provided herein. In some cases, the barcode sequence is located between the two biological nucleotide sequence priming sites in a synthetic template provided herein (e.g., synthetic target oligonucleotides or synthetic control gene oligonucleotides). In some cases, the synthetic templates can further comprise a random oligonucleotide sequence as provided herein. The random oligonucleotide sequence can be located between the two synthetic nucleotide sequence priming sites, wherein substantially every synthetic template from the set of synthetic templates comprises a unique random oligonucleotide sequence. A barcode sequence in any synthetic template (e.g., synthetic target oligonucleotides or synthetic control gene oligonucleotides) provided herein can be used to indicate a particular well or sample source. The unique random oligonucleotide sequence ("randomer") in any synthetic template (e.g., synthetic target oligonucleotides or synthetic control gene oligonucleotides) provided herein can be used to indicate an individual molecule in the sample and that the sequence originated from a synthetic template.

The sample can be any sample as provided herein.

In some embodiments, the first adaptor sequence on each of the first set of primers and each of the third set of primers comprises a universal adaptor sequence, such as a PGEX sequence, although any suitable adapter may be used.

```
pGEX Forward      GGGCTGGCAAGCCACGTTTGGTG
(GST 5, pGEX 5')  (SEQ ID NO: 1)

pGEX Reverse      CCGGGAGCTGCATGTGICAGAGG
(GST 3, pGEX 3')  (SEQ ID NO: 2)
```

Further to these embodiments, the second adapter sequence on each of the second set of primers can be a universal adaptor sequence that is different from the adaptor sequence on each of the first and third set of primers. For example, when a pGEX adaptor sequence is on each of the first and third set of primers, the second set of primers cannot have a pGEX adaptor sequence and vice versa.

In one embodiment, the biological nucleotide molecules are adaptive immune receptors (AIRs). The AIRs can be T-cell receptor (TCR) nucleotide molecules or genes or B-cell iummunoglobulin (Ig) nucleotide molecules or genes. In these cases, the synthetic nucleotide molecules can be referred to as synthetic target templates or synthetic target oligonucleotides. In some cases, the biological nucleotide molecules are control nucleotide molecules or genes. The control nucleotide molecules or genes can be nucleotide molecules or genes that are typically constitutive gene required for the maintenance of basic cellular function, and expressed in all cells of an organism under normal and under most patho-physiological conditions such as, for example housekeeping genes. Examples of housekeeping genes (HKGs) for use in the methods and compositions provided herein can include, but are not limited to, beta (β)-actin (ACTB), beta-2-microglobulin (B2M), C1orf34, charged multivesicular body protein 2A (CHMP2A), glucose-6-phosphate isomerase (GPI), glucuronidase, beta (GUSB), hydroxymethylbilane synthase (HMBS), hypoxanthine phosphoribosyltransferase 1 (HPRT1), proteasome subunit beta 4 (PSMB4), ribosomal protein L13a (RPL13A), ribosomal protein lateral stalk subunit PO (RPLPO), succinate dehydrogenase complex flavoprotein subunit A (SDHA), small nuclear ribonucleoprotein D3 polypeptide (SNRPD3), ubiquitin C (UBC), valosin containing protein (VCP), Vacuolar protein sorting 29 (VPS29), peptidylprolyl isomerase A (PPIA), proteasome subunit beta 2 (PSMB2), ER Membrane Protein Complex Subunit 7 (EMC7), Ras-Related Protein Rab-7a (RAB7A) and Receptor Accessory Protein 5 (REEP5), RNase P, lactate dehydrogenoase A (LDHA), Non-POU domain-containing octamer-binding protein (NONO), Phosphoglycerate kinase 1 (PGK1), and Peptidylprolyl cis-trans isomerase H (PPIH). In these cases, the synthetic nucleotide molecules can be referred to as synthetic controls or synthetic control gene oligonucleotides or templates.

The compositions provided herein comprising the first set of primers, the second set of primers, and the third set of primers can be utilized in a method that can generally comprise: performing a first polymerase chain reaction (PCR) on the composition to generate a plurality of first amplicons comprising the first adapter sequences and a plurality of second amplicons comprising the second adapter sequence; amplifying the plurality of first amplicons in a second PCR using a set of tailing primers, wherein each tailing primer comprises a sequence complementary to said first adapter sequence and a sequencing adapter oligonucleotide sequence to produce a plurality of amplicons comprising the first adapter sequence and the sequencing adapter oligonucleotide sequence; and performing high throughput sequencing of the plurality of amplicons from the second PCR to produce a plurality of sequence reads. In one embodiment, the first PCR is a multiplex PCR. The multiplex PCR can be performed as described herein. The third set of primers can be capable of amplifying the second region of the synthetic templates under the same conditions as the first set of primers (and second set of primers).

Further to the above embodiments wherein the set of biological nucleotide molecules comprise one or more control genes, the first PCR comprising the first set of primer pairs in the methods provided herein can result in amplicons (i.e., first amplicons) of both the synthetic control gene oligonucleotides and the biological control gene molecules such that each member of the amplicon (i.e., first amplicon) produced using the first set of primer pairs can comprise a) the amplified control gene sequence and b) flanking first adaptor sequences. The synthetic control gene templates in the amplicon (i.e., first amplicon) can be identified by the presence of barcode sequences. In preferred embodiments, the third set of primers each comprise the first adaptor sequence that is the same as the adaptor sequence found in the first set of primers and first set of amplicons.

In some embodiments, the first set of primer pairs can be added into the first PCR mixture at a low concentration compared with other primers in the mixture (e.g., second set of primer pairs and/or third set of primers pairs), or at a lower concentration than used for a standard PCR amplification. In some embodiments, the first set of primers is present at an amount 10%, 20%, 30%, 40%, 50%, 60%, 70%, 80%, 90%, 95% or 99% lower than the second set of primers. In some embodiments, the first set of primer pairs is included at a ratio of 1:2, or 1:3 or 1:4 or 1:5 or 1:6 or 1:7 or 1:8 or 1:9 or 1:10 or 1:15 or 1:20 or 1:25 or 1:30, or 1:40 or 1:50 or 1:100 or 1:200, or 1:300 or 1:400 or 1:500 or 1:600 or 1:700 or 1:800 or 1:1000 or 1:5000, or 1:10,000 to other primers in the mixture (e.g., second set of primer pairs and/or third set of primers pairs). Use of the lower concentration of the first set of primer pairs can result in a relatively low number of amplicons (i.e., first amplicons) comprising the biological and synthetic control gene sequence and the flanking first adaptor sequences. The use of a lower concentration of primers to produce a relatively lower number of amplicons can be called a "down-sampling" assay.

In another embodiment, each of primers in the first set of primer pairs in the composition and for use in the methods provided herein have a low binding affinity for the target control gene sequences (biological and synthetic templates). For example, the first set of primer pairs can have less than 100% complementarity to the target sequence. Each of the primers can have 1, 2, 3, or more mismatched oligonucleotide sequences in the primer sequence. The binding affinity of the first set of primers can be lower than an optimal binding affinity, and/or lower than the affinity of the second set of primer pairs that hybridize to the target sequence (i.e. "first synthetic nucleotide sequence"). This can result in fewer amplicons produced from the first PCR using the first set of primer pairs vs. the second set of primer pairs. The use of a lower binding affinity primers to produce a relatively lower number of amplicons can also be used in a "down-sampling" assay to amplify a fewer number of target sequences.

In preferred embodiments, the third set of primers each comprise the first adaptor sequence that is the same as the adaptor sequence found in the first set of primers and first set of amplicons. Further to the "downsampling" embodiments described above, the first PCR performed on the compositions comprising the first, second and third sets of primer pairs provided herein can result in three set of amplicons such that the first set of amplicons comprise the first adaptor sequence and the control gene sequence and are found in low concentrations as compared to the second set of amplicons comprising the second adaptor sequence and the control gene sequence and the third set of amplicons comprising the first adaptor sequence and the non-biological synthetic sequence ("second region").

As described herein, following the first PCR utilizing the first, second and/or third set of primers as described herein, a second PCR using a set of tailing primer pairs can be performed to amplify the amplicons from the first PCR. As provided herein, each primer in the set of tailing primer pairs can comprise 1) a sequencing oligonucleotide sequence, and 2) a sequence that is complementary to the first adaptor sequence, but not complementary to the second adaptor sequence.

Where the tailing primers are complementary to only one of the adaptor sequences (for example, the first adaptor sequence), the tailing PCR assay can result in amplification of only the amplicons that include the first adaptor sequence (not the second adaptor sequence). In embodiments where there are fewer starting amplicons with the first adaptor sequence and the first synthetic nucleotide sequence, this can result in a few amplicons with the first adaptor sequence and first synthetic nucleotide sequence. The amplicons comprising the second adaptor sequence are not amplified in the tailing reaction. The resulting amplicons can comprise the sequencing oligonucleotide, which can be compatible with a sequencing platform-specific oligonucleotide.

The various sets of amplicons using the methods and compositions provided herein are subsequently sequenced as described above. Namely, after the tailing PCR, amplicons that comprise a platform-specific sequencing oligonucleotide are sequence using any compatible high throughput sequencing platform known in the art.

In one embodiment, the amplicons comprising the first adaptor sequence and the control gene sequence ("first region" or "first synthetic nucleotide sequence") are sequenced at very low sequencing depth (e.g., taking sequencing depth to be the mean number of sequencing reads observed per molecule of material added as input to the first PCR). Put another way and as described above, methods can be used to produce fewer numbers of amplicons comprising the first adaptor sequence and the control gene sequence. For example, there can be fewer number of resulting amplicons due to use of a lower concentration of the first set of primers in the first PCR. In other embodiments, the numbers of sequencable amplicons is low due to a low binding affinity of the primers.

In any of the methods described herein, a first adaptor sequence may comprise a molecular tag. In some embodiments, a molecular tag is or comprises a mosaic tag.

In addition, the amplicons comprising the synthetic, non-biological sequence (i.e., second synthetic nucleotide sequence) can be sequenced at a normal sequencing depth by virtue of the fact that all amplicons contain the appropriate adapters and all primers can be substantially 100% complementary to the template to be amplified, using the high throughput sequencing methods provided herein. A sufficient amount of sequencing can be performed of the synthetic sequences, such that each uniquely-tagged synthetic template in the PCR input can be observed with high confidence in the sequencing read output.

The number of output sequence reads of the non-biological, synthetic sequences (i.e., second synthetic nucleotide sequence) can be used to infer the number of input synthetic templates added to the first PCR reaction. The number of resulting sequence reads of the non-biological, synthetic sequences (i.e., second synthetic nucleotide sequence) can be analyzed for the presence and number of unique random oligonucleotide tag sequences. Each unique random oligonucleotide tag sequence can correspond to a single input synthetic molecule.

An amplification factor can be determined from the number of output sequence reads of the non-biological, synthetic sequences (i.e., second synthetic nucleotide sequence) and the number of input synthetic templates.

Amplification factor=number of output sequence reads from non-biological, synthetic sequences (i.e., second synthetic nucleotide sequence)/number of unique random oligonucleotide tag sequences observed in output sequence reads from non-biological, synthetic sequences (i.e., second synthetic nucleotide sequence).

The same amplification factor applies to the other starting templates in the PCR. For example, if there are 1000 output sequence reads of the non-biological, synthetic sequences (i.e., second synthetic nucleotide sequence), and 100 starting synthetic templates, the amplification factor is 10× the number of starting input molecules.

This amplification factor can then be used to determine the number of input biological control genes are in the sample.

In embodiments where the biological control genes are amplified with the same primers as the control gene synthetic templates, the number of output sequence reads of biological control genes and the synthetic control gene templates can be quantified.

Using the amplification factor determined from the non-biological, synthetic molecules, the number of input biological control gene molecules can be calculated as follows: number of input biological control gene molecules=(number of sequencing reads from biological control gene templates)/(number of sequencing reads from synthetic control gene templates/number of unique random oligonucleotide tag sequences observed in non-biological, synthetic templates).

The number of input biological control gene molecules can be equivalent to the total number of cells that are present in the starting material.

In one embodiment, the amplification and sequencing of biological and synthetic AIR genes (e.g., TCR or IG Sequences) are performed. Further to this embodiment, the number of biological TCR or IG molecules can therefore be determined. In this embodiment, a multiplex PCR assay using V segment and J segment primers is performed on a second set of templates that include i) biological TCR or IG rearranged nucleic acid molecules and ii) synthetic templates that match all of the biological TCR or IG rearranged nucleic acid molecules that could potentially be found in the sample. The synthetic TCR of IG templates can be have a structure according to any of the formulas for synthetic templates provided herein. In general, the synthetic TCR of IG templates can include a unique random oligonucleotide tag sequence that identifies the molecule as synthetic. Further, primer sets comprising V segment and J segment primers can be used to amplify all or substantially all of the biological and synthetic TCR or IG templates in the sample. The primer pairs or sets of primer pairs for use in amplifying all or substantially all of the biological and synthetic TCR or IG templates in the sample can be the primer sets found in WO2015/134787, which is herein incorporated by reference in its entirety.

The tailing PCR and sequencing steps can be performed on the biological and synthetic TCR or IG templates as described above for the biological and synthetic control templates.

The resulting output can include a number of sequence reads for the biological TCR or IG templates and a number of sequence reads for the synthetic TCR or IG templates.

In one embodiment, quantification of the number of input biological TCR or IG molecules in a sample can be determined. Given that the number of input synthetic TCR or IG templates can be inferred based on the number of unique random oligonucleotide tag sequences observed in output sequence reads from synthetic TCR or IG sequences, the number of input TCR or IG biological molecules can= (number of sequencing reads from biological TCR or IG templates)/(number of sequencing reads from synthetic TCR or IG templates/number of unique random oligonucleotide tag sequences observed in synthetic TCR or IG templates)

In another embodiment, the quantification of the ratio of biological TCR or IG sequences to control gene sequences can be determined. The ratio of biological TCR or IG molecules to control gene sequences can be the ratio of the number of input TCR or IG biological molecules to the number of input biological control gene molecules.

In one embodiment, the method comprises sequencing an adaptive immune receptor locus (e.g., T-cell receptor such as TCRB or B-cell Ig molecule) at high sequence coverage and a control gene (e.g., housekeeping gene; HKG) at low sequence coverage and then determining the proportion of TCRB:HKG templates in the sample. The method comprises: (a) obtain a plurality of biological TCRB templates and biological HKG templates, which are each targeted by a set of gene-specific V and J segment PCR primers. The V segment and J segment primers can be any V and J segment primers known in the art such as, for example, those found in in WO2015/134787.

(b) Introduce into the sample two synthetic templates: (i) a first set of synthetic templates, each comprising a unique random oligonucleotide tag sequence (N8) and is amplified by the same primers as TCRB, and (ii) a second set of synthetic templates, each comprising two distinct, non-overlapping sequence regions. The first region (i.e., first synthetic nucleotide sequence) is amplified by the same primers as the biological HKG template and may or may not contains a unique random oligonucleotide tag sequence (N8). The second region (i.e., second synthetic nucleotide sequence) includes unique random oligonucleotide tag sequence (N8) and is a non-biological synthetic sequence (SYN). The second region is amplified by a set of primers distinct from both the TCRB and HKG gene-specific primers, and the primers do not amplify any biological nucleic acids expected to be present in the biological input material.

(c) Perform PCR with four sets of primers: one set of primers which amplify TCRB and include a pGEX tail; one set of primers which amplify HKG and include a pGEX tail (primers are at a low relative concentration); one set of primers which amplify HKG and include a non-pGex tail (high relative concentration); and one set of primers which amplify SYN and include a pGEX tail.

(d) Perform a second tailing PCR, using primers that include a pGEX sequence and an Illumina sequencing adaptor. All PCR products from the first PCR of TCRB and SYN templates have Illumina sequencing adaptors incorporated into the amplicon. A small number of biological and synthetic HKG amplicons have Illumina sequencing adaptors incorporated.

(e) Perform high-throughput sequencing of the amplicons.

(f) Calculate the number of input TCR biological templates as follows: (number of sequencing reads from biological TCRB templates)/(number of sequencing reads from synthetic TCRB templates/number of unique random oligonucleotide tag sequences observed in synthetic TCRB templates).

(g) Calculate the number of input HKG biological templates as follows: (number of sequencing reads from biological HKG templates)/(number of sequencing reads from synthetic HKG templates/number of unique random oligonucleotide tag sequences observed in synthetic SYN templates).

(h) Determine the ratio of biological TCRB:HKG sequences such that said ratio is the number derived in (f) to the number derived in (g). Thus, the ratio of biological TCRB:HKG templates has been inferred while sequencing the HKG templates with very low coverage.

Figure 1B:
FIG. 1B illustrates an embodiment of the quantification steps of the method.
Figure 1B:
Figure 1B:
Figure 1B:
Figure 1B:
Figure 1B:

An illustration of the above embodiments is shown in FIGS. 1A and 1B.

In FIG. 1A, a plurality of biological control gene templates (101), labeled as HKG, are amplified. There are a large number of biological control gene templates (for example, 10,000 molecules). A plurality of synthetic templates (102) are also amplified. These can be the synthetic control gene oligonucleotides referred to herein. There are fewer numbers of synthetic templates (for example, 100 molecules). The synthetic templates comprise a control gene sequence (102A) that matches the biological control gene sequence (HKG, 101) and are amplified with the same primers as the biological control gene templates (101). There are two sets of primers (103) that are used to amplify the biological and synthetic control gene templates. One set of primers is found in a low concentration and includes a pGEX adaptor sequence (dashed line). A second set of primers is added at a higher concentration but includes an "unrelated" adaptor (solid line). In some cases, the second set of primers can lack an adaptor sequence.

The plurality of synthetic templates (102) also includes a non-biological, synthetic sequence (102B) that is not found in any cell in the sample. These non-biological, synthetic sequences each include a unique random oligonucleotide tag sequence (N8). For example, there are 100 unique random oligonucleotide tag sequences that represent 100 unique synthetic template molecules. The non-biological synthetic sequences (102B) are amplified with primers that include a pGEX adaptor sequence (dashed line).

In a first PCR (step 104), three sets of primers are used to amplify the biological control gene templates (101) and the synthetic templates (102). The resulting amplicons include: 1) a biological control gene amplicon with a pGEX adaptor sequence, 2) a biological control gene amplicon with an unrelated adaptor sequence, 3) a synthetic control gene amplicon with a pGEX adaptor sequence, 4) a synthetic control gene amplicon with an unrelated adaptor sequence, 5) a non-biological, synthetic sequence with a pGEX adaptor sequence.

In a second PCR 105, tailing primers are used to amplify the amplicons from the first PCR. The tailing primers includes a platform-specific oligonucleotide sequence and a sequence that is complementary to the pGEX adaptor sequence. Thus, only the amplicons with the pGEX adaptor are amplified in the second PCR and include a platform-specific oligonucleotide sequence. In FIG. 1A-1B, only 1 synthetic control gene amplicon out of 100 amplicons has the pGEX adaptor sequence.

The resulting amplicons are then sequenced using any sequencing method provided herein such as, for example, Illumina HTS. Here, there are 1,000 biological control gene amplicons and 10 synthetic control gene amplicons, The sequencing step results in the following sequence reads: a) output biological control gene sequence reads, b) output synthetic control gene sequence reads, and c) output nonbiological synthetic sequence reads. The number of unique output non-biological synthetic sequence reads (106) is used to infer the number of input synthetic molecules (102) that were in the starting sample.

As shown in FIGS. 1A and 1i, a second set of reactions can be performed using TCRB biological molecules (107) and TCRB synthetic templates (108). The TCRB synthetic templates include a unique random oligonucleotide tag sequence (N8). There are many more TCRB biological molecules than synthetic templates (1000:100). The TCRB biological molecules (107) and TCRB synthetic templates (108) are amplified in a first PCR by the same set of multiplex PCR primers (V segment and J segment primers) that include pGEX adaptor sequences on the 5'-ends. The V segment and J segment primers can be any V and J segment primers known in the art such as, for example, those found in in WO2015/134787. The resulting amplicons are then amplified in a second PCR with tailing primers that have i) sequences that are complementary to the pGEX adaptor sequences and ii) High throughput sequencing (HTS) platform-specific oligonucleotide sequences. HTS is performed for the biological TCRB amplicons and the synthetic TCRB amplicons.

In FIG. 1B, quantitation steps are shown, according to an embodiment of the invention. As shown in I), the number of input biological TCRB molecules is determined. First, an amplification factor is calculated for the biological and synthetic TCRB molecules. For example, if 100 unique random oligonucleotide tag sequences are counted from the synthetic TCRB sequence reads, and there are 1000 output synthetic TCRB sequence reads, the amplification factor is 10× for each molecule.

This amplification factor can be applied to the biological TCRB molecules. The number of biological TCRB molecules is divided by the amplification factor. In this example, 10,000/10 is 1000. Thus, there were 1000 input biological TCRB molecules in the starting material.

As shown in II), the number of input biological control genes is determined. First, an amplification factor is calculated. The amplification factor is the number of output synthetic control gene sequences (10) divided by the number of unique random oligonucleotide tag sequences (10/100=0.1). Next, the number of biological control gene sequence reads is divided by the amplification factor to get the total number of input biological control gene molecules in the starting sample. Here, the calculation is 1000/0.1=10,000 input biological control gene molecules.

Finally, a ratio of the number of biological TCRB molecules to the number of total cells in the sample can be calculated. In this example, T cells represent 10% of the initial sample. (1,000 input biological TCRB molecules/10,000 input biological control gene molecules=0.1=10%).

Specifically, while TCR and IG genes are exemplified for ease of description, it is apparent to one of skill in the art that any biological molecule(s) can be quantified in accordance with the compositions and methods of the current invention. All one needs to know is the possible sequences of the biological template to be amplified such that the appropriate synthetic templates could be constructed.

Kits

Provided herein are kits comprising reagents comprising a composition comprising a plurality of synthetic control oligonucleotides, a set of oligonucleotide primers directed against the plurality of synthetic control templates or oligonucleotides and the control genes (e.g. HKGs) represented by the plurality of synthetic template oligonucleotides, a plurality of synthetic target templates or oligonucleotides and a set of oligonucleotide primers directed against the plurality of synthetic template oligonucleotides and the AIRs represented by the plurality of synthetic template oligonucleotides, and instructions for quantifying a relative representation of adaptive immune cells in a biological sample that comprises a mixture of cells comprising adaptive immune cells and cells that are not adaptive immune cells as described herein.

Also provided herein are kits comprising reagents comprising a composition comprising a plurality of synthetic template oligonucleotides and a set of oligonucleotide primers directed against the plurality of synthetic template oligonucleotides and the AIRs represented by the plurality of synthetic template oligonucleotides, and instructions for quantifying a relative representation of adaptive immune cells in a biological sample that comprises a mixture of cells comprising adaptive immune cells and cells that are not adaptive immune cells, by quantifying: (i) a synthetic template product number of amplified synthetic template oligonucleotide molecules, and (ii) a biological rearranged product number of a number of output sequences.

Synthetic Templates

As provided herein, the methods and compositions entail the use of synthetic templates. In one embodiment, the methods provided herein involve constructing and/or use of the synthetic templates.

In one embodiment, the methods and compositions provided herein comprise two sets of synthetic templates such that a first set of synthetic templates are synthetic target templates or oligonucleotides that represent one or more target genes (e.g. AIR genes such as TCR genes or B-cell receptor genes), while a second set of synthetic templates are synthetic control gene templates or oligonucleotides that represent one or more control genes (e.g., HKGs). The first set of synthetic templates (synthetic target templates or oligonucleotides) can be used for counting or quantifying a total number of input biological TCR or IG molecules in a starting biological sample. The second set of synthetic templates (synthetic control gene templates or oligonucleotides) can be used for counting or quantifying a total number of input synthetic molecules in a starting biological sample as well as determining an amplification factor of the synthetic control templates (e.g., HKGs) in a PCR. In general, the sets of synthetic templates or oligonucleotides provided herein can comprise sequences that are substantially identical to biological sequences (i.e. TCR V, J or C segments or genomic control regions (e.g., HKG)) in addition to non-naturally occurring sequences (i.e. barcodes, randomers, adaptors, etc.). The full nucleotide sequence of synthetic templates provided herein, therefore, do not occur in nature and are, instead, laboratory designed and made sequences.

In general, the set of synthetic target templates or oligonucleotides for use in methods wherein the target nucleic acids are AIR genes (e.g., TCR or B-cell receptor genes) can have the general formula (I) or (II):

5'-U1-B1-V-B2-J-B3-U2-3'       (I).

5'-U1-B1-V-I-B2-N-J-B3-U2-3'   (II).

The constituent template oligonucleotides are diverse with respect to the nucleotide sequences of the individual template oligonucleotides.

In one embodiment, U1 and U2 are each either nothing or each comprise an oligonucleotide having, independently, a sequence that is selected from (i) a universal adaptor oligonucleotide sequence, and (ii) a sequencing platform-specific oligonucleotide sequence that is linked to and positioned 5' to the universal adaptor oligonucleotide sequence.

In one embodiment, I depicted in general formula II is an internal marker oligonucleotide sequence comprising at least 2 nucleotides, and not more than 100 nucleotides.

B1, B2, and B3 can each be independently either nothing or each comprise an oligonucleotide "B" that comprises an oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 contiguous nucleotides (including all integer values therebetween). In some embodiments, B1, B2, and B3 can each comprise a unique oligonucleotide sequence that uniquely identifies, or identifies as a paired combination, (i) the unique V oligonucleotide sequence of the template oligonucleotide and (ii) the unique J oligonucleotide sequence of the template oligonucleotide.

The relative positioning of the barcode oligonucleotides B1, B2, and B3 and universal adaptors U1 and U2 advantageously permits rapid identification and quantification of the amplification products of a given unique synthetic target template oligonucleotide by short sequence reads and paired-end sequencing on automated DNA sequencers (e.g., Illumina HiSeq™ or Illumina MiSEQ®, or GeneAnalyzer™-2, Illumina Corp., San Diego, Calif.). In particular, these and related embodiments permit rapid high-throughput determination of specific combinations of a V-segment sequence and a J-segment sequence that are present in an amplification product, thereby to characterize the relative amplification efficiency of each V-specific primer and each J-specific primer that may be present in a primer set, which is capable of amplifying rearranged TCR or BCR encoding DNA in a sample. Verification of the identities and/or quantities of the amplification products may be accomplished by longer sequence reads, optionally including sequence reads that extend to B2.

V can be either nothing or a polynucleotide comprising at least 20, 30, 60, 90, 120, 150, 180, or 210, and not more than 1000, 900, 800, 700, 600 or 500 contiguous nucleotides of a DNA sequence. In some embodiments, the DNA sequence is of an adaptive immune receptor variable (V) region encoding gene sequence, or the complement thereof, and in each of the plurality of template oligonucleotide sequences V comprises a unique oligonucleotide sequence.

J can be either nothing or a polynucleotide comprising at least 15-30, 31-60, 61-90, 91-120, or 120-150, and not more than 600, 500, 400, 300 or 200 contiguous nucleotides of a DNA sequence. In some embodiments, the DNA sequence is of an adaptive immune receptor joining (J) region encoding gene sequence, or the complement thereof, and in each of the plurality of template oligonucleotide sequences J comprises a unique oligonucleotide sequence.

In constructing the "V" and "J" portions of the synthetic template oligonucleotides of formula I or II, various adaptive immune receptor variable (V) region and joining (J) region gene sequences can be used. A large number of V and J region gene sequences are known as nucleotide and/or amino acid sequences, including non-rearranged genomic DNA sequences of TCR and Ig loci, and productively rearranged DNA sequences at such loci and their encoded products, and also including pseudogenes at these loci, and also including related orphons. See, e.g., U.S. Ser. No. 13/217,126; U.S. Ser. No. 12/794,507; PCT/US2011/026373; PCT/US2011/049012, which are incorporated by reference in their entireties. Moreover, genomic sequences for TCR and BCR V region genes of humans and other species are known and available from public databases such as Genbank. V region gene sequences include polynucleotide sequences that encode the products of expressed, rearranged TCR and BCR genes and also include polynucleotide sequences of pseudogenes that have been identified in the V region loci. The diverse V polynucleotide sequences that may be incorporated into the presently disclosed templates of general formula I or II may vary widely in length, in nucleotide composition (e.g., GC content), and in actual linear polynucleotide sequence, and are known, for example, to include "hot spots" or hypervariable regions that exhibit particular sequence diversity. These and other sequences known to the art may be used according to the present disclosure for the design and production of synthetic target template oligonucleotides to be included in the presently provided template composition for standardizing amplification efficiency of an oligonucleotide primer set, and for the design and production of the oligonucleotide primer set that is capable of amplifying rearranged DNA encoding TCR or Ig polypeptide chains, which rearranged DNA may be present in a biological sample comprising lymphoid cell DNA.

The entire polynucleotide sequence of each polynucleotide V in general formula I or II can, but need not, consist exclusively of contiguous nucleotides from each distinct V gene. For example and according to certain embodiments, in the template composition described herein, each polynucleotide V of formula I or II need only have at least a region comprising a unique V oligonucleotide sequence that is found in one V gene and to which a single V region primer in the primer set can specifically anneal. Thus, the V polynucleotide of formula I or II may comprise all or any prescribed portion (e.g., at least 15, 20, 30, 60, 90, 120, 150, 180 or 210 contiguous nucleotides, or any integer value therebetween) of a naturally occurring V gene sequence (including a V pseudogene sequence), so long as at least one unique V oligonucleotide sequence region (e.g., the primer annealing site) is included that is not included in any other template V polynucleotide.

In some embodiments, the plurality of V polynucleotides that are present in the synthetic target template composition have lengths that simulate the overall lengths of known, naturally occurring V gene nucleotide sequences, even where the specific nucleotide sequences differ between the template V region and any naturally occurring V gene. The V region lengths in the synthetic templates can differ from the lengths of naturally occurring V gene sequences by no more than 1, 2, 3, 4, 5, 6, 7, 8, 9, 10, 11, 12, 13, 14, 15, 16, 17, 18, 19 or 20 percent. Optionally and according to certain embodiments, the V polynucleotide of the herein described synthetic template oligonucleotide includes a stop codon at or near the 3' end of V in general formula I or II.

The V polynucleotide in formula (I) may thus, in certain embodiments, comprise a nucleotide sequence having a length that is the same or similar to that of the length of a typical V gene from its start codon to its CDR3 encoding region and may, but need not, include a nucleotide sequence that encodes the CDR3 region. CDR3 encoding nucleotide sequences and sequence lengths may vary considerably and have been characterized by several different numbering schemes (e.g., Lefranc, 1999 *The Immunologist* 7:132; Kabat et al., 1991 In: *Sequences of Proteins of Immunological Interest*, NIH Publication 91-3242; Chothia et al., 1987 *J. Mol. Biol.* 196:901; Chothia et al., 1989 *Nature* 342:877; Al-Lazikani et al., 1997 *J. Mol. Biol.* 273:927; see also, e.g., Rock et al., 1994 *J. Exp. Med.* 179:323; Saada et al., 2007 *Immunol. Cell Biol.* 85:323).

Briefly, the CDR3 region typically spans the polypeptide portion extending from a highly conserved cysteine residue (encoded by the trinucleotide codon TGY; Y=T or C) in the V segment to a highly conserved phenylalanine residue (encoded by TTY) in the J segment of TCRs, or to a highly conserved tryptophan (encoded by TGG) in IGH. More than 90% of natural, productive rearrangements in the TCRB locus have a CDR3 encoding length by this criterion of between 24 and 54 nucleotides, corresponding to between 9 and 17 encoded amino acids. The CDR3 lengths of the presently disclosed synthetic target oligonucleotides should, for any given TCR or BCR locus, fall within the same range as 95% of naturally occurring rearrangements. Thus, for example, in a synthetic template composition described herein, the CDR3 encoding portion of the V polynucleotide cab has a length of from 24 to 54 nucleotides, including every integer therebetween. The numbering schemes for CDR3 encoding regions described above denote the positions of the conserved cysteine, phenylalanine and tryptophan codons, and these numbering schemes may also be applied to pseudogenes in which one or more codons encoding these conserved amino acids may have been replaced with a codon encoding a different amino acid. For pseudogenes which do not use these conserved amino acids, the CDR3 length may be defined relative to the corresponding position at which the conserved residue would have been observed absent the substitution, according to one of the established CDR3 sequence position numbering schemes referenced above.

The entire polynucleotide sequence of each polynucleotide J in general formula I or II may, but need not, consist exclusively of contiguous nucleotides from each distinct J gene. For example and according to certain embodiments, in the template composition described herein, each polynucleotide J of formula I or II need only have at least a region comprising a unique J oligonucleotide sequence that is found in one J gene and to which a single V region primer in the primer set can specifically anneal. Thus, the V polynucleotide of formula I or II may comprise all or any prescribed portion (e.g., at least 15, 20, 30, 60, 90, 120, 150, 180 or 210 contiguous nucleotides, or any integer value therebetween) of a naturally occurring V gene sequence (including a V pseudogene sequence) so long as at least one unique V oligonucleotide sequence region (the primer annealing site) is included that is not included in any other template J polynucleotide.

It may be preferred in certain embodiments that the plurality of J polynucleotides that are present in the herein described synthetic target template composition have lengths that simulate the overall lengths of known, naturally occurring J gene nucleotide sequences, even where the specific nucleotide sequences differ between the template J region and any naturally occurring J gene. The J region lengths in the herein described templates may differ from the lengths of naturally occurring J gene sequences by no more than 1, 2, 3, 4, 5, 6, 7, 8, 9, 10, 11, 12, 13, 14, 15, 16, 17, 18, 19 or 20 percent.

The J polynucleotide in formula I or II may thus, in certain embodiments, comprise a nucleotide sequence having a length that is the same or similar to that of the length of a typical naturally occurring J gene and may, but need not, include a nucleotide sequence that encodes the CDR3 region, as discussed above.

Genomic sequences for TCR and BCR J region genes of humans and other species are known and available from public databases such as Genbank; J region gene sequences include polynucleotide sequences that encode the products of expressed and unexpressed rearranged TCR and BCR genes. The diverse J polynucleotide sequences that may be incorporated into the presently disclosed templates of general formula I or II may vary widely in length, in nucleotide composition (e.g., GC content), and in actual linear polynucleotide sequence.

Alternatives to the V and J sequences described herein, for use in construction of the herein described synthetic target template oligonucleotides and/or V-segment and J-segment oligonucleotide primers, may be selected by a skilled person based on the present disclosure using knowledge in the art regarding published gene sequences for the V- and J-encoding regions of the genes for each TCR and Ig subunit. Reference Genbank entries for human adaptive immune receptor sequences include: TCRα: (TCRA/D): NC_000014.8 (chr14:22090057 . . . 23021075); TCRβ: (TCRB): NC_000007.13 (chr7:141998851 . . . 142510972); TCRγ: (TCRG): NC_000007.13 (chr7:38279625 . . . 38407656); immunoglobulin heavy chain, IgH (IGH): NC_000014.8 (chr14: 106032614 . . . 107288051); immunoglobulin light chain-kappa, IgLκ (IGK): NC_000002.11 (chr2: 89156874 . . . 90274235); and immunoglobulin light chain-lambda, IgLλ (IGL): NC_000022.10 (chr22: 22380474 . . . 23265085). Reference Genbank entries for mouse adaptive immune receptor loci sequences include: TCRβ: (TCRB): NC_000072.5 (chr6: 40841295 . . . 41508370), and immunoglobulin heavy chain, IgH (IGH): NC_000078.5 (chr12:114496979 . . . 117248165).

Template and primer design analyses and target site selection considerations can be performed, for example, using the OLIGO primer analysis software and/or the BLASTN 2.0.5 algorithm software (Altschul et al., *Nucleic Acids Res.* 1997, 25(17):3389-402), or other similar programs available in the art.

Accordingly, based on the present disclosure and in view of these known adaptive immune receptor gene sequences and oligonucleotide design methodologies, for inclusion in the instant template oligonucleotides those skilled in the art can design a plurality of V region-specific and J region-specific polynucleotide sequences that each independently contain oligonucleotide sequences that are unique to a given V and J gene, respectively. Similarly, from the present disclosure and in view of known adaptive immune receptor sequences, those skilled in the art can also design a primer set comprising a plurality of V region-specific and J region-specific oligonucleotide primers that are each independently capable of annealing to a specific sequence that is unique to a given V and J gene, respectively, whereby the plurality of primers is capable of amplifying substantially all V genes and substantially all J genes in a given adaptive immune receptor-encoding locus (e.g., a human TCR or IgH locus). Such primer sets permit generation, in multiplexed (e.g., using multiple forward and reverse primer pairs) PCR, of amplification products that have a first end that is encoded by a rearranged V region-encoding gene segment and a second end that is encoded by a J region-encoding gene segment.

In certain embodiments, such amplification products may include a CDR3-encoding sequence although the invention is not intended to be so limited and contemplates amplification products that do not include a CDR3-encoding sequence. The primers may be preferably designed to yield amplification products having sufficient portions of V and J sequences and/or of V-J barcode (B) sequences as described herein, such that by sequencing the products (amplicons), it is possible to identify on the basis of sequences that are unique to each gene segment (i) the particular V gene, and (ii) the particular J gene in the proximity of which the V gene underwent rearrangement to yield a functional adaptive immune receptor-encoding gene. Typically, and in preferred embodiments, the PCR amplification products will not be more than 600 base pairs in size, which according to non-limiting theory will exclude amplification products from non-rearranged adaptive immune receptor genes. In certain other preferred embodiments the amplification products will not be more than 500, 400, 300, 250, 200, 150, 125, 100, 90, 80, 70, 60, 50, 40, 30 or 20 base pairs in size, such as may advantageously provide rapid, high-throughput quantification of sequence-distinct amplicons by short sequence reads.

In one embodiment of formula I or II, V is a polynucleotide sequence that encodes at least 10-70 contiguous amino acids of an adaptive immune receptor V-region, or the complement thereof; J is a polynucleotide sequence that encodes at least 5-30 contiguous amino acids of an adaptive immune receptor J-region, or the complement thereof; U1 and U2 are each either nothing or comprise an oligonucleotide comprising a nucleotide sequence that is selected from (i) a universal adaptor oligonucleotide sequence, and (ii) a sequencing platform-specific oligonucleotide sequence that is linked to and positioned 5' to the universal adaptor oligonucleotide sequence; B1, B2, and B3 are each independently either nothing or each comprise an oligonucleotide B that comprises an oligonucleotide barcode sequence of 3, 4, 5, 6, 7, 8, 9, 10, 11, 12, 13, 14, 15, 16, 17, 18, 19 or 20 contiguous nucleotides, wherein in each of the plurality of oligonucleotide sequences, B comprises a unique oligonucleotide sequence that uniquely identifies, as a paired combination, (i) the unique V oligonucleotide sequence and (ii) the unique J oligonucleotide sequence.

In another embodiment of formula (I), V is a polynucleotide sequence of at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400 or 450 and not more than 1000, 900, 800, 700, 600 or 500 contiguous nucleotides of an adaptive immune receptor (e.g., TCR or BCR) variable (V) region gene sequence, or the complement thereof, and in each of the plurality of oligonucleotide sequences V comprises a unique oligonucleotide sequence.

Additional description about synthetic target oligonucleotides can be found in International Application No. PCT/US2013/040221, filed May 8, 2013, which is incorporated by reference in its entirety.

The synthetic target oligonucleotides of Formula I can also include adaptor sequences. The adaptor sequences can be added to the synthetic target oligonucleotides by designing primers that include adaptor sequences at their 5'-ends and that specifically hybridize to the adaptor UA and UB regions on the synthetic target oligonucleotides. An example of an adaptor sequence is an Illumina adaptor sequence, as described in the section "Adaptors" below.

In general, the set of synthetic control gene templates can comprise at least two non-overlapping regions of sequence. The first non-overlapping region comprises a "target" sequence that matches a segment or portion or all of a biological control gene sequence that is found at single copy in typical cells of the species of interest. This control gene sequence can serve as an internal control. The control gene sequence can be a housekeeping gene, for example, which can be a typically constitutive gene that is required for the maintenance of basic cellular function, and is expressed in all cells of an organism under normal and under most patho-physiological conditions. Examples of housekeeping genes include, but are not limited to, ER Membrane Protein Complex Subunit 7 (EMC7), Ras-Related Protein Rab-7a (RAB7A) and Receptor Accessory Protein 5 (REEP5), RNase P, lactate dehydrogenoase A (LDHA), Non-POU domain-containing octamer-binding protein (NONO), Phosphoglycerate kinase 1 (PGK1), and Peptidyl-prolyl cis-trans isomerase H (PPIH). The synthetic sequence may include a unique random oligonucleotide tag sequence of length N that uniquely labels each molecule of input synthetic template. N can be 4, 5, 6, 7, 8, 9, 10, 11, 12, 13, 14, 15, 16, 17, 18, 19, 20, or greater in length. In one embodiment, the synthetic sequence does not include a unique random oligonucleotide tag sequence. The second non-overlapping region of the synthetic control gene templates can comprise a separate "off-target" synthetic sequence that does not match any segment or portion or all of any DNA sequence found in typical cells of the species of interest (e.g. this sequence might constitute a purely synthetic DNA sequence, or a segment of a housekeeping gene from a species other than the species of interest). The non-biologically occurring synthetic sequence can include a unique random oligonucleotide tag sequence of length N that uniquely labels each molecule of input synthetic template. N can be 4, 5, 6, 7, 8, 9, 10, 11, 12, 13, 14, 15, 16, 17, 18, 19, 20, or greater in length. In a preferred embodiment, N is 8 nucleotides in length.

The set of synthetic control gene templates can include a spacer region (or spacer) between the first and second regions. The spacer region can be 4, 5, 6, 7, 8, 9, 10, 11, 12, 13, 14, 15, 16, 17, 18, 19, 20, 25, 30, 40, 45, 50, 60, 70, 80, 90, 100, 150, 200, 250, 300, 400, 500, 1000, 2000, 3000, 4000, 5000 or more nucleotides in length. The space region may consist of nucleotide sequence known to produce substantial secondary structure. In a preferred embodiment, the spacer is 200 nucleotides in length.

In one embodiment, the first and second regions of the set of synthetic control gene templates are amplified separately by at least two different pairs of primer sets.

The synthetic control gene templates comprise one or more barcode sequences that identify the template molecules as synthetic.

In some cases, the first non-overlapping portion of the synthetic control gene oligonucleotides in the set of synthetic control gene templates can be similar to the synthetic target oligonucleotides described herein, but do not contain a V oligonucleotide sequence or a J oligonucleotide sequence. Instead, the first non-overlapping portion of each synthetic control gene oligonucleotide or template in the set of synthetic control gene templates can comprise a plurality of template oligonucleotides of general formula (II):

5'-U1-B1-X1-B2-N-X2-B3-U2-3' (II).

The segments U1, B1, B2, N, B3, and U2 are the same as described above for the synthetic target templates. In an embodiment, X1 and X2 are either nothing or each comprises a polynucleotide comprising at least 10, 20, 30, or 40, and not more than 1000, 900, or 800 contiguous nucleotides of a DNA sequence. In some embodiments, the DNA sequence is of a genomic control gene (also referred to as an "internal control gene"), or the complement thereof. As used herein "genomic control gene" or "internal control gene" is any gene that is found in all cells (including both adaptive immune cells and cells that are not adaptive immune cells), such as a housekeeping gene like EMC7, RAB7A, REEP5, RNase P, LDHA, NONO, PGK1, and PPPIH.

Barcodes

As described herein, certain embodiments contemplate designing the synthetic template oligonucleotide sequences provided herein to contain short signature sequences that permit unambiguous identification of the template sequence, and hence of at least one primer responsible for amplifying that template, without having to sequence the entire amplification product. In the herein described synthetic target oligonucleotides of general formula (I), B1, B2, B3, and B4 are each independently either nothing or each comprises an oligonucleotide B that comprises an oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 or more contiguous nucleotides (including all integer values therebetween), wherein in each of the plurality of template oligonucleotide sequences B comprises a unique oligonucleotide sequence that uniquely identifies, as a paired combination, (i) the unique V oligonucleotide sequence of the template oligonucleotide and (ii) the unique J oligonucleotide sequence of the template oligonucleotide.

Thus, for instance, synthetic template oligonucleotides (e.g., synthetic target oligonucleotides or synthetic control gene oligonucleotides) having barcode identifier sequences may permit relatively short amplification product sequence reads, such as barcode sequence reads of no more than 1000, 900, 800, 700, 600, 500, 400, 300, 200, 100, 90, 80, 70, 60, 55, 50, 45, 40, 35, 30, 25, 20, 19, 18, 17, 16, 15, 14, 13, 12, 11, 10, 9, 8, 7, 6, 5, 4 or fewer nucleotides, followed by matching this barcode sequence information to the associated V and J sequences that are incorporated into the template having the barcode as part of the template design. By this approach, a large number of amplification products can be simultaneously partially sequenced by high throughput parallel sequencing, to identify primers that are responsible for amplification bias in a complex primer set.

Exemplary barcodes may comprise a first barcode oligonucleotide of 5, 6, 7, 8, 9, 10, 11, 12, 13, 14, 15 or 16 nucleotides that uniquely identifies each V polynucleotide in the template and a second barcode oligonucleotide of 5, 6, 7, 8, 9, 10, 11, 12, 13, 14, 15 or 16 nucleotides that uniquely identifies each J polynucleotide in the template, to provide barcodes of, respectively, 10, 11, 12, 13, 14, 15, 16, 17, 18, 19, 20, 21, 22, 23, 24, 25, 26, 27, 28, 29, 30, 31 or 32 nucleotides in length, but these and related embodiments are not intended to be so limited. Barcode oligonucleotides may comprise oligonucleotide sequences of any length, so long as a minimum barcode length is obtained that precludes occurrence of a given barcode sequence in two or more template oligonucleotides having otherwise distinct sequences (e.g., V and J sequences).

Thus, the minimum barcode length, to avoid such redundancy amongst the barcodes that are used to uniquely identify different V-J sequence pairings, is X nucleotides, where $4^x$ is greater than the number of distinct template species that are to be differentiated on the basis of having non-identical sequences. For example, for the set of 858 template oligonucleotides set forth in SEQ ID NO:1888-3003 of US20170292149A1, which is herein incorporated by reference in its entirety, the minimum barcode length would be five nucleotides, which would permit a theoretical total of 1024 (i.e., greater than 871) different possible pentanucleotide sequences. In practice, barcode oligonucleotide sequence read lengths may be limited only by the sequence read-length limits of the nucleotide sequencing instrument to be employed. For certain embodiments, different barcode oligonucleotides that will distinguish individual species of template oligonucleotides should have at least two nucleotide mismatches (e.g., a minimum hamming distance of 2) when aligned to maximize the number of nucleotides that match at particular positions in the barcode oligonucleotide sequences.

In preferred embodiments, for each distinct template oligonucleotide species having a unique sequence within the template composition of general formula (I), B1, B2, B3, and B4 will be identical.

The skilled artisan will be familiar with the design, synthesis, and incorporation into a larger oligonucleotide or polynucleotide construct, of oligonucleotide barcode sequences of, for instance, at least 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 70, 80, 90, 100, 200, 300, 300, 500 or more contiguous nucleotides, including all integer values therebetween. For non-limiting examples of the design and implementation of oligonucleotide barcode sequence identification strategies, see, e.g., de Carcer et al., 2011 *Adv. Env. Microbiol.* 77:6310; Parameswaran et al., 2007 *Nucl. Ac. Res.* 35(19):330; Roh et al., 2010 *Trends Biotechnol.* 28:291.

Typically, barcodes are placed in templates at locations where they are not found naturally, i.e., barcodes comprise nucleotide sequences that are distinct from any naturally occurring oligonucleotide sequences that may be found in the vicinity of the sequences adjacent to which the barcodes are situated (e.g., V and/or J sequences). Such barcode sequences may be included, according to certain embodiments described herein, as elements B1, B2 and/or B3 of the presently disclosed template oligonucleotide of general formula (I). Accordingly, certain of the herein described template oligonucleotides of general formula (I) may also in certain embodiments comprise one, two or all three of barcodes B1, B2 and B3, while in certain other embodiments some or all of these barcodes may be absent. In certain embodiments all barcode sequences will have identical or similar GC content (e.g., differing in GC content by no more than 20%, or by no more than 19, 18, 17, 16, 15, 14, 13, 12, 11 or 10%).

In the template compositions according to certain herein disclosed embodiments the barcode-containing element B (e.g., B1, B2, B3, and/or B4) comprises the oligonucleotide sequence that uniquely identifies a single paired V-J combination. Optionally and in certain embodiments the barcode-containing element B may also include a random nucleotide, or a random polynucleotide sequence of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 70, 80, 90, 100, 200, 300, 300, 500 or more contiguous nucleotides, situated upstream and/or downstream of the specific barcode sequence that uniquely identifies each specific paired V-J combination. When present both upstream and downstream of the specific barcode sequence, the random nucleotide or random polynucleotide sequence are independent of one another, that is, they may but need not comprise the same nucleotide or the same polynucleotide sequence.

Samples

Samples used in the methods of the invention can include, any tissue from a subject. In certain embodiments, the tissue comprises infiltrating lymphocytes or a lymphoid infiltrate in the tissue. The lymphoid infiltrate can be malignant or benign. Samples can be obtained from a bodily fluid from a subject, such as a peripheral blood sample.

With respect to embodiments utilizing adaptive immune receptor bearing cells (e.g. T cells or B cells), any peripheral tissue can be sampled for the presence of B and T cells and is therefore contemplated for use in the methods described herein. Tissues and biological fluids from which adaptive immune cells may be obtained include, but are not limited to skin, epithelial tissues, colon, spleen, a mucosal secretion, oral mucosa, intestinal mucosa, vaginal mucosa or a vaginal secretion, cervical tissue, ganglia, saliva, cerebrospinal fluid (CSF), bone marrow, cord blood, serum, serosal fluid, plasma, lymph, urine, ascites fluid, pleural fluid, pericardial fluid, peritoneal fluid, abdominal fluid, culture medium, conditioned culture medium or lavage fluid. In certain embodiments, adaptive immune cells may be isolated from an apheresis sample. Peripheral blood samples may be obtained by phlebotomy from subjects. Peripheral blood mononuclear cells (PBMC) are isolated by techniques known to those of skill in the art, e.g., by Ficoll-Hypaque® density gradient separation. In certain embodiments, whole PBMCs are used for analysis. In some embodiments, the sample comprises solid tumor tissue, a circulating blood mononuclear cell fraction, or cells collected from urinary sediment.

In some embodiments, the subject is a mammalian subject, for example, a human subject. In one embodiment, the subject is a healthy subject. In other embodiments, the subject has a disease or condition of interest, such as cancer, autoimmune disease, etc. In another embodiment, samples from the subject are obtained prior to and after a medical event, such as a treatment, immunotherapy, surgery, or vaccination. In yet another embodiment, samples are obtained from the subject and analyzed before and after a stimulation event, such as an enrichment (in vitro stimulation of lymphocytes with an antigen), or a mixed lymphocyte reaction.

As used herein, the term "obtaining from a subject" encompasses both directly obtaining a sample or tissue from a subject (i.e. by blood draw or biopsy) or indirectly obtaining a sample or tissue wherein a third party (i.e. a medical professional) obtains the sample or tissue from the subject and transfers the sample in a processed or unprocessed state to a different party to carry out the multiplex PCR. Similarly, the term "obtained from a biological sample" includes both directly obtaining something, for example DNA, from the biological sample or indirectly obtaining, for example DNA, from the sample by processing of the sample by a third party. It will also be understood that the methods of the current invention may be practiced by several different parties, for example, a medical practitioner may obtain the samples and a laboratory technician may process the samples to obtain DNA from the sample which may then be transferred to another lab technician who may run the multiplex PCR and/or HTS, or transmit the amplicons from the multiplex PCR to still another party who may perform the HTS. In some embodiments, the person who performs the multiplex PCR and/or HTS may also be the actor responsible for the quantitative methods, in another embodiment; still a different person may perform the quantitative methods described herein.

The sample includes any cells that will be the subject of multiplex PCR and HTS, for example the samples may include T cells and/or B cells. T cells (T lymphocytes) include, for example, cells that express T cell receptors. T cells include Helper T cells (effector T cells or Th cells), cytotoxic T cells (CTLs), memory T cells, and regulatory T cells. The sample can include one or more expanded clones, including one or more dominant clones (e.g., a top T cell clone), among a number of T cells or a total number of nucleated cells. The sample can include at least 1,000, at least 10,000, at least 100,000, at least 250,000, at least 500,000, at least 750,000, or at least 1,000,000 T cells.

B cells include, for example, plasma B cells, memory B cells, B1 cells, B2 cells, marginal-zone B cells, and follicular B cells. B cells express immunoglobulins (Igs, antibodies, B cell receptor). The sample can include one or more expanded clones, including a dominant clone (e.g., a top B cell clone), among a number of benign B cells or a total number of nucleated cells. The sample can include a single B cell in some applications or more generally at least 1,000, at least 10,000, at least 100,000, at least 250,000, at least 500,000, at least 750,000, or at least 1,000,000 B-cells.

The sample can include nucleic acid molecules extracted from a cell, for example, DNA (e.g., genomic DNA or mitochondrial DNA) or RNA (e.g., messenger RNA or microRNA). The nucleic acid can be cell-free DNA or RNA. In other embodiments, the sample comprises complementary DNA (cDNA) that has been reverse transcribed from mRNA. In the methods of the provided invention, the amount of RNA or DNA from a subject that can be analyzed includes, for example, as low as a single cell in some applications and as many as 10 millions of cells or more, translating to a range of DNA of 6 pg-60 µg, and RNA of approximately 1 pg-10 µg.

Cells

B cells and T cells can be obtained from a biological sample, as described above.

In other embodiments, specific subpopulations of T or B cells may be isolated prior to analysis using the methods described herein. Various methods and commercially available kits for isolating different subpopulations of T and B cells are known in the art and include, but are not limited to, subset selection immunomagnetic bead separation or flow immunocytometric cell sorting using antibodies specific for one or more of any of a variety of known T and B cell surface markers. Illustrative markers include, but are not limited to, one or a combination of CD2, CD3, CD4, CD8, CD14, CD19, CD20, CD25, CD28, CD45RO, CD45RA, CD54, CD62, CD62L, CDw137 (41BB), CD154, GITR, FoxP3, CD54, and CD28. For example, and as is known to the skilled person, cell surface markers, such as CD2, CD3, CD4, CD8, CD14, CD19, CD20, CD45RA, and CD45RO may be used to determine T, B, and monocyte lineages and subpopulations in flow cytometry. Similarly, forward light-scatter, side-scatter, and/or cell surface markers such as CD25, CD62L, CD54, CD137, and CD154 may be used to determine activation state and functional properties of cells.

Illustrative combinations useful in certain of the methods described herein may include $CD8^+CD45RO^+$ (memory cytotoxic T cells), $CD4^+CD45RO^+$ (memory T helper), $CD8^+CD45RO^-$ ($CD8^+CD62L^+CD45RA^+$ (naïve-like cytotoxic T cells); $CD4^+CD25^+CD62L^{hi}GITR^+FoxP3^+$ (regulatory T cells). Illustrative antibodies for use in immunomagnetic cell separations or flow immunocytometric cell sorting include fluorescently labeled anti-human antibodies, e.g., CD4 FITC (clone M-T466, Miltenyi Biotec), CD8 PE (clone RPA-T8, BD Biosciences), CD45RO ECD (clone UCHL-1, Beckman Coulter), and CD45RO APC (clone UCHL-1, BD Biosciences). Staining of total PBMCs may be done with the appropriate combination of antibodies, followed by washing cells before analysis. Lymphocyte subsets can be isolated by fluorescence activated cell sorting (FACS), e.g., by a BD FACSAria™ cell-sorting system (BD Biosciences) and by analyzing results with FlowJo™ software (Treestar Inc.), and also by conceptually similar methods involving specific antibodies immobilized to surfaces or beads.

Nucleic Acid Extraction

In some embodiments, total genomic DNA can be extracted from cells by methods known to those of skill in the art. Examples include using the QIAamp® DNA blood Mini Kit (QIAGEN®). The approximate mass of a single haploid genome is 3 pg. Preferably, at least 100,000 to 200,000 cells are used for analysis of diversity, i.e., about 0.6 to 1.2 µg DNA from diploid T cells. Using PBMCs as a source, the number of T cells can be estimated to be about 30% of total cells.

In some embodiments, RNA can be extracted from cells in a sample, such as a sample of blood, lymph, tissue, or other sample from a subject known to contain lymphoid cells, using standard methods or commercially available kits known in the art. In other embodiments, cDNA can be transcribed from mRNA obtained from the cells and then used as templates in a multiplex PCR.

Alternatively, total nucleic acid can be isolated from cells, including both genomic DNA and mRNA. If diversity is to be measured from mRNA in the nucleic acid extract, the mRNA can be converted to cDNA prior to measurement. This can readily be done by methods of one of ordinary skill, for example, using reverse transcriptase according to known procedures.

In certain embodiments, DNA can be isolated from frozen, OCT embedded or formalin fixed paraffin embedded (FFPE) skin samples. For OCT embedded tissue samples, cryosections can be cut and DNA extraction can be carried extracted using known techniques. For FFPE samples, paraffin is first removed from the tissue scrolls and DNA can then be extracted by known techniques.

Multiplex Quantitative PCR

"Multiplex PCR" or "multiplexed PCR" refers to a PCR wherein multiple target sequences are simultaneously amplified by a set of primers in the same reaction mixture. Multiplex quantitative PCR is described herein and in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. Ser. No. 13/217,126, U.S. Ser. No. 12/794,507, WO/2010/151416, WO/2011/106738 (PCT/US2011/026373), WO2012/027503 (PCT/US2011/049012), U.S. Ser. No. 61/550,311, and U.S. Ser. No. 61/569,118, which are each incorporated by reference in its entirety. In one embodiment, a single multiplex PCR method uses a set of forward primers that specifically hybridize to V segments and a set of reverse primers that specifically hybridize to the J segments of a TCR or IG locus, where a single multiplex PCR reaction using the primers allows amplification of all the possible VJ (and VDJ) combinations within a given population of T or B cells.

A single multiplex PCR system can be used to amplify rearranged adaptive immune cell receptor loci from genomic DNA, preferably from a CDR3 region. In certain embodiments, the CDR3 region is amplified from a TCRA, TCRG, TCRG or TCRD CDR3 region or similarly from an IGH or IGL (lambda or kappa) locus. Compositions are provided that comprise a plurality of V segment and J segment primers that are capable of promoting amplification in a multiplex polymerase chain reaction (PCR) of substantially all productively rearranged adaptive immune receptor CDR3-encoding regions in the sample for a given class of such receptors to produce a multiplicity of amplified rearranged DNA molecules from a population of T cells (for TCR) or B cells (for IG) in the sample. In certain embodiments, primers are designed so that each amplified rearranged DNA molecule is less than 600 nucleotides in length, thereby excluding amplification products from non-rearranged adaptive immune receptor loci.

In some embodiments, the method uses two pools of primers to provide for a highly multiplexed, single tube PCR reaction. A "forward" pool of primers can include a plurality of V segment oligonucleotide primers used as "forward" primers and a plurality of J segment oligonucleotide primers used as "reverse" primers. In other embodiments, J segment primers can be used as "forward" primers, and V segment can be used "reverse" primers. In some embodiments, an oligonucleotide primer that is specific to (e.g., having a nucleotide sequence complementary to a unique sequence region of) each V-region encoding segment ("V segment") in the respective TCR or IG gene locus can be used. In other embodiments, primers targeting a highly conserved region are used to simultaneously amplify multiple V segments or multiple J segments, thereby reducing the number of primers required in the multiplex PCR. In certain embodiments, the J segment primers anneal to a conserved sequence in the joining ("J") segment.

Each primer can be designed such that a respective amplified DNA segment is obtained that includes a sequence portion of sufficient length to identify each J segment unambiguously based on sequence differences amongst known J-region encoding gene segments in the human genome database, and also to include a sequence portion to which a J segment specific primer can anneal for resequencing. This design of V and J segment specific primers enables direct observation of a large fraction of the somatic rearrangements present in the adaptive immune receptor gene repertoire within an individual. This feature in turn enables rapid comparison of the TCR and/or IG repertoires in individuals pre-transplant and post-transplant, for example.

In some embodiments, the primers comprise a universal tag. In one embodiment, the universal tag is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, or 50 nucleotides in length. In one embodiment the universal tag is at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, or at least 50 nucleotides in length.

In some embodiments, more than one universal tag is present on the same primer. In some embodiments, two universal tags occur on the same primer. In some embodiments, a primer to one target sequence will utilize a different universal tag from a primer to another target sequence. In some embodiments, each different forward and/or reverse primer to a particular target will utilize a different universal tag from the forward and/or reverse primer to another target. In some embodiments, each primer and/or set of primers comprise(s) a different universal tag.

In one embodiment, the present disclosure provides a plurality of V segment primers and a plurality of J segment primers, wherein the plurality of V segment primers and the plurality of J segment primers amplify all or substantially all combinations of the V and J segments of a rearranged immune receptor locus. In some embodiments, the method provides amplification of substantially all of the rearranged adaptive immune receptor (ATR) sequences in a lymphoid cell and is capable of quantifying the diversity of the TCR or IG repertoire of at least $10^6$, $10^5$, $10^4$, or $10^3$ unique rearranged AIR sequences in a sample. "Substantially all combinations" can refer to at least 80%, 85%, 90%, 91%, 92%, 93%, 94%, 95%, 96%, 97%, 98%, 99% or more of all the combinations of the V and J segments of a rearranged immune receptor locus. In certain embodiments, the plurality of V segment primers and the plurality of J segment primers amplify all of the combinations of the V and J segments of a rearranged adaptive immune receptor locus.

In general, a multiplex PCR system can use 2, 3, 4, 5, 6, 7, 8, 9, 10, 11, 12, 13, 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments, 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to or is complementary to a sequence corresponding to one or more V region segments. The multiplex PCR system also uses at least 2, 3, 4, 5, 6, or 7, and in certain embodiments, 8, 9, 10, 11, 12 or 13 reverse primers, or 14, 15, 16, 17, 18, 19, 20, 21, 22, 23, 24, or 25 or more primers, in which each reverse primer specifically hybridizes to or is complementary to a sequence corresponding to one or more J region segments. In some embodiments, each reverse J primer is specific to a different J gene segment. In other embodiments, there is no common J primer that binds to all J gene segments.

The V segment and J segment primers have certain characteristics to amplify the total diversity of TCR or IG repertoires. In certain embodiments, the V segment primers have similar melting temperatures within a range of 0.1° C., 0.2° C., 0.3° C., 0.4° C., 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.5° C., 5.0° C. In some embodiments, the J segment primers have similar melting temperatures within a range of 0.1° C., 0.2° C., 0.3° C., 0.4° C., 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.5° C., 5.0° C.

In certain embodiments, the plurality of V segment and J segment primers are not consensus primers. The V segment and J segment primers are not universal, degenerate primers. In some embodiments, each V segment primer is complementary to a single V segment or a family of V segments. In some embodiments, each J segment primer is complementary to a single J segment or a family of J segments. In other embodiments, each J segment primer is complementary and specific to a single J segment gene.

In other embodiments, the plurality of V segment and J segment primers sit outside a region of untemplated deletions in the TCR or IG locus. In some embodiments, the 3' end of the V segment primers are complementary to a target region that is at least 10, 11, 12, 13, 14, 15, 16, 17, 18, 19, 20, 21, 22, 23, 24, 25, 26, 27, 28, 29, 30 or more nucleotides upstream from the V-RSS. In some embodiments, the 3' end of the J segment primers are complementary to a target region that is at least 10, 11, 12, 13, 14, 15, 16, 17, 18, 19, 20, 21, 22, 23, 24, 25, 26, 27, 28, 29, 30 or more nucleotides downstream from the J-RSS.

Various combinations of V and J segment primers can be used to amplify the full diversity of TCR and IG sequences in a repertoire. For details on the multiplex PCR system, including exemplary primer oligonucleotide sequences for amplifying substantially all TCR and/or IG sequences, see, e.g., Robins et al., 2009 *Blood* 114, 4099; Robins et al., 2010 *Sci. Translat. Med.* 2:47ra64; Robins et al., 2011 *J. Immunol. Meth*. doi:10.1016/j.jim.2011.09. 001; Sherwood et al. 2011 *Sci. Translat. Med.* 3:90ra61; U.S. Ser. No. 13/217,126, U.S.

Ser. No. 12/794,507, WO/2010/151416, WO/2011/106738 (PCT/US2011/026373), WO2012/027503 (PCT/US2011/049012), U.S. Ser. No. 61/550,311, U.S. Ser. No. 61/569,118, WO/2013/188831 (PCT/US2013/045994), which is each incorporated by reference in its entirety.

Oligonucleotides or polynucleotides that are capable of specifically hybridizing or annealing to a target nucleic acid sequence by nucleotide base complementarity can do so under moderate to high stringency conditions. For purposes of illustration, suitable moderate to high stringency conditions for specific PCR amplification of a target nucleic acid sequence would be between 25 and 80 PCR cycles, with each cycle consisting of a denaturation step (e.g., about 10-30 seconds (s) at greater than about 95° C.), an annealing step (e.g., about 10-30 s at about 60-68° C.), and an extension step (e.g., about 10-60 s at about 60-72° C.), optionally according to certain embodiments with the annealing and extension steps being combined to provide a two-step PCR. As would be recognized by the skilled person, other PCR reagents can be added or changed in the PCR reaction to increase specificity of primer annealing and amplification, such as altering the magnesium concentration, optionally adding DMSO, and/or the use of blocked primers, modified nucleotides, peptide-nucleic acids, and the like.

In certain embodiments, nucleic acid hybridization techniques can be used to assess hybridization specificity of the primers described herein. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the primers are designed not to cross an intron/exon boundary. The forward primers in certain embodiments anneal to the V segments in a region of relatively strong sequence conservation between V segments so as to maximize the conservation of sequence among these primers. Accordingly, this minimizes the potential for differential annealing properties of each primer, and so that the amplified region between V and J primers contains sufficient TCR or Ig V sequence information to identify the specific V gene segment used. In one embodiment, the J segment primers hybridize with a conserved element of the J segment and have similar annealing strength. In one particular embodiment, the J segment primers anneal to the same conserved framework region motif. In certain embodiments, the J segment primers have a melting temperature range within 10° C., 7.5° C., 5° C., or 2.5° C. or less.

Oligonucleotides (e.g., primers) can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Lett.* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

A primer is preferably a single-stranded oligonucleotide. The appropriate length of a primer depends on the intended use of the primer but typically ranges from 6 to 50 nucleotides, 15-50 nucleotides, or in certain embodiments, from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

As described herein, primers can incorporate additional features which allow for the detection or immobilization of the primer, but do not alter the basic property of the primer, that of acting as a point of initiation of DNA synthesis. For example, primers can contain an additional nucleic acid sequence at the 5' end, which does not hybridize to the target nucleic acid, but which facilitates cloning, detection, or sequencing of the amplified product. The region of the primer which is sufficiently complementary to the template to hybridize is referred to herein as the hybridizing region.

As used herein, a primer is "specific" for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences which contain the target primer binding sites. In other terms, the primers of the invention are each complementary to a target sequence and can include 1, 2, or more mismatches without reducing complementarity or hybridization of the primer to the target sequence.

In particular embodiments, primers for use in the methods described herein comprise or consist of a nucleic acid of at least about 15 nucleotides long that has the same sequence as, or is substantially complementary to, a contiguous nucleic acid sequence of the target V or J segment. Longer primers, e.g., those of about 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80 or more nucleotides long that have the same sequence as, or sequence complementary to, a contiguous sequence of the target V or J segment, will also be of use in certain embodiments. Various mismatches (1, 2, 3, or more) to the target sequence can be contemplated in the primers, while preserving complementarity to the target V or J segment. All intermediate lengths of the aforementioned primers are contemplated for use herein. As would be recognized by the skilled person, the primers can have additional sequence added (e.g., nucleotides that cannot be the same as or complementary to the target V or J segment), such as restriction enzyme recognition sites, adaptor sequences for sequencing, bar code sequences, and the like (see e.g., primer sequences provided herein and in the sequence listing). Therefore, the length of the primers can be longer, such as 55, 56, 57, 58, 59, 60, 65, 70, 75, or 80 or more nucleotides in length or more, depending on the specific use or need.

For example, in one embodiment, the forward and reverse primers are both modified at the 5' end with the universal forward primer sequence compatible with a DNA sequencing nucleic acid sequence. Such universal primers sequences can be adapted to those used in the Illumina GAII single-end read sequencing system. Exemplary universal primer sequences and sequencing oligonucleotides are provided in U.S. Ser. No. 13/217,126, U.S. Ser. No. 12/794,507, PCT/US2011/049012, PCT/US2013/045994, which are incorporated by reference in their entireties.

In some embodiments, the forward and reverse primers are both modified at the 5' end with an adaptor sequence that is not complementary to the V segment, J segment, or C segment (target sequence) and can be a region that is identical to or complementary to a second set of primers or a sequencing oligonucleotide. A first multiplex PCR using the forward and reverse primers modified with adaptor sequences produce a first set of amplicons comprising the adaptor sequences.

In a second PCR reaction, a set of tailing primers is used to amplify the first set of amplicons. The tailing primers include regions that are complementary to the adaptor sequence of the first set of amplicons. The tailing primers may also include other sequences at their 5' ends, such as a barcode sequence, random nucleotide sequences, platform specific sequencing oligonucleotides (Illumina compatible sequence), or other sequence tags. In some embodiments, the barcode sequence can be used to identify the source of the sample and/or identify the well or cell from which the sequence originated. In other embodiments, the random sequences can be used to track and quantify individual sequence molecules.

In some embodiments, the barcode sequence acts as an index for multiple polynucleotide samples. In some embodiments, the barcode sequence is 2, 3, 4, 5, 6, 7, 8, 9, 10, 11, 12, 13, 14, or 15 nucleotides in length. In some embodiments, the barcode sequence is at least 2, at least 3, at least 4, at least 5, at least 6, at least 7, at least 8, at least 9, at least 10, at least 11, at least 12, at least 13, at least 14, or at least 15 nucleotides in length.

In some embodiments, the random nucleotide sequence is a nucleic acid sequence that comprises random bases. In some embodiments, the random nucleotide sequence is 2, 3, 4, 5, 6, 7, 8, 9, 10, 11, 12, 13, 14, or 15 nucleotides in length. In some embodiments, the barcode sequence is at least 2, at least 3, at least 4, at least 5, at least 6, at least 7, at least 8, at least 9, at least 10, at least 11, at least 12, at least 13, at least 14, or at least 15 nucleotides in length.

The adaptor sequence of the forward and reverse primers can be a universal adaptor oligonucleotide sequence. In another embodiment, the adaptor sequence can be a sequencing platform-specific oligonucleotide sequence that is specific to a single-molecule sequencing technology being employed. Examples of sequencers include the HiSeq™ or GeneAnalyzer™-2 (GA-2) systems (Illumina, Inc., San Diego, Calif.) or another suitable sequencing suite of instrumentation, reagents and software. Inclusion of such platform-specific adaptor sequences permits direct quantitative sequencing of amplification products. This feature therefore advantageously permits qualitative and quantitative characterization of the composition. In one example, dsDNA amplification products may be generated that have universal adaptor sequences at both ends, so that the adaptor sequences can be used to further incorporate sequencing platform-specific oligonucleotides at each end of each template.

As would be recognized by the skilled person, in certain embodiments, other modifications may be made to the primers, such as the addition of restriction enzyme sites, fluorescent tags, and the like, depending on the specific application.

Also contemplated are adaptive immune receptor V segment or J segment oligonucleotide primer variants that can share a high degree of sequence identity to the oligonucleotide primers. Thus, in these and related embodiments, adaptive immune receptor V segment or J segment oligonucleotide primer variants can have substantial identity to the adaptive immune receptor V segment or J segment oligonucleotide primer sequences disclosed herein. For example, such oligonucleotide primer variants can comprise at least 70% sequence identity, preferably at least 75%, 80%, 85%, 90%, 91%, 92%, 93%, 94%, 95%, 96%, 97%, 98%, or 99% or higher sequence identity compared to a reference polynucleotide sequence such as the oligonucleotide primer sequences disclosed herein, using the methods described herein (e.g., BLAST analysis using standard parameters). One skilled in this art will recognize that these values can be appropriately adjusted to determine corresponding ability of an oligonucleotide primer variant to anneal to an adaptive immune receptor segment-encoding polynucleotide by taking into account codon degeneracy, reading frame positioning and the like. Typically, oligonucleotide primer variants will contain one or more substitutions, additions, deletions and/or insertions, preferably such that the annealing ability of the variant oligonucleotide is not substantially diminished relative to that of an adaptive immune receptor V segment or J segment oligonucleotide primer sequence that is specifically set forth herein. As noted herein, in preferred embodiments, adaptive immune receptor V segment and J segment oligonucleotide primers are designed to be capable of amplifying a rearranged TCR or IGH sequence that includes the coding region for CDR3.

According to certain embodiments, the primers for use in the multiplex PCR methods of the present disclosure can be functionally blocked to prevent non-specific priming of non-T or B cell sequences. For example, the primers can be blocked with chemical modifications as described in U.S. Publication No. 2010/0167353.

In some embodiments, the V and J segment primers are used to produce a plurality of amplicons from the multiplex PCR reaction. In certain embodiments, the V segment primer sand J segment primers can produce at least $10^6$ amplicons representing the diversity of TCR or IG rearranged CDR3 molecules in the sample.

In some embodiments, the amplicons range in size from 10, 20, 30, 40, 50, 75, 100, 200, 300, 400, 500, 600, 700, 800, 900, 1000, 1100, 1200, 1300, 1400, 1500 to 1600 nucleotides in length. In preferred embodiments, the amplicons have a size between 50-600 nucleotides in length.

According to non-limiting theory, these embodiments exploit current understanding in the art that once an adaptive immune cell (e.g., a T or B lymphocyte) has rearranged its adaptive immune receptor-encoding (e.g., TCR or Ig) genes, its progeny cells possess the same adaptive immune receptor-encoding gene rearrangement, thus giving rise to a clonal population that can be uniquely identified by the presence therein of rearranged (e.g., CDR3-encoding) V and J-gene segments that can be amplified by a specific pairwise combination of V and J-specific oligonucleotide primers as herein disclosed.

Amplification Bias Control

Multiplex PCR assays can result in a bias in the total numbers of amplicons produced from a sample, given that certain primer sets are more efficient in amplification than others. Multiplex PCR poses unique challenges because all primers must function under the same reaction conditions, which should not only allow each primer to anneal to its true target sequence, but minimize non-specific amplification and avoid production of primer-dimers. Small variations in annealing kinetics can have a large impact on primer amplification efficiency, producing biased PCR product libraries where the observed frequency of each amplicon is not proportional to the original frequency of the input template. In extreme cases, such bias can result in undetectable levels of specific under-amplifying target templates.

In some embodiments, the present disclosure overcomes the problem of biased utilization of subpopulations of amplification primers with methods that can be used to provide spiked-in synthetic template compositions for standardizing the amplification efficiencies of the members of an oligonucleotide primer set, where the primer set is capable of amplifying rearranged DNA encoding a plurality of adaptive immune receptors (TCR or Ig) in a biological sample that comprises DNA from lymphoid cells. See Carlson C S, Emerson R O, Sherwood A M, Desmarais C, Chung M-W, Parsons J M, et al. Using synthetic templates to design an unbiased multiplex PCR assay. Nature Communications. 2013; 4:2680, which is incorporated in its entirety by reference.

For example, a method can be developed for using a synthetic analogue of a somatically rearranged immune receptor locus (human TCRG) to quantify and correct multiplex PCR amplification bias. As the actual in vivo TCRG repertoire is a priori impossible to know, a synthetic repertoire that includes a template for every possible V/J combination can be developed. Using these synthetic templates, the amplification bias present in the biological assay can be identified and corrected. The precise composition of the reference template pool is measured before and after amplification. The effect of primer concentration on amplification rates is then measured, and these data are used to titre the relative concentration of each primer in the multiplex reaction, such that all V/J combinations amplified with similar efficiencies. Residual differences in amplification efficiency are removed computationally using experimentally derived normalization factors. The method for amplification bias control for the TCRG locus is described previously in Carlson et al. Nature Communications. 2013; 4:2680.

The same method can be used for amplification bias control of other adaptive immune receptor loci. For example, in TCRB, each potential VDJ rearrangement of the TCRB locus contains one of thirteen J segments, one of 2 D segments and one of 52 V segments, many of which have disparate nucleotide sequences. In order to amplify all possible VDJ combinations, a multiplex PCR assay with 45 V forward and 13 J reverse primers can be used. To remove potential PCR bias, every possible V-J pair is chemically synthesized as a template with specific barcodes. These synthetic templates are engineered to be recognized as non-biologic and have universal 3' and 5' ends to permit amplification with universal primers and subsequent quantification by HTS. This "synthetic immune system" can then be used to calibrate the multiplex PCR assay. Iteratively, the multiplex pool of templates is amplified and sequenced with TCRB V/J-specific primers, as described above, and the primer concentrations are adjusted to re-balance PCR amplification. Once the multiplex primer mixture amplifies each V and J template nearly equivalently, residual bias is removed computationally.

To identify the overall baseline amplification bias of our multiplex primers, the synthetic template pool is amplified with an equimolar mixture of each V and J primer, in PCR replicates. Input templates can be identified that are over-represented, under-represented and severely under-represented. Using an ANOVA analysis, Carlson et al. found that while each V and J primer has a characteristic amplification bias, no significant evidence for specific interactions was observed ($P \frac{1}{4}$ 0.11 by F-test), allowing the conclusion that the V and J primer amplification biases can be treated independently when adjusting primer concentrations to reduce amplification bias.

Minimizing primer amplification bias and measuring robustness. To ensure that each primer is sensitive to changes in concentration, primer titration tests can be performed (one V or J primer at a time is increased two-fold or four-fold in concentration) to show that increasing the concentration of an individual primer within the PCR mix increases the post-amplification template representation of the targeted templates.

Computational adjustments to normalize amplification bias. Amplification bias factors derived from the multiplex primer mix using the synthetic template pool allow a straight-forward normalization procedure to computationally remove residual amplification bias from libraries amplified using the same multiplex primer mix. The residual scaling factors can be calculated using the ratio of pre- to post-amplification frequency for each of the synthetic templates. Each V or J gene segment is assigned the mean ratio of its constituent templates (that is, for each V segment, the mean amplification bias is calculated among the templates using that gene segment), and these are used as the final normalization factors to correct sequencing output (that is, the number of reads) for increased accuracy.

In some embodiments, the synthetic target templates comprise a template composition of general formula (I):

$$5'\text{-}U1\text{-}B1\text{-}V\text{-}B2\text{-}X\text{-}J\text{-}B3\text{-}U2\text{-}3' \quad (I)$$

The constituent template oligonucleotides, of which the template composition is comprised, are diverse with respect to the nucleotide sequences of the individual template oligonucleotides. The individual template oligonucleotides can vary in nucleotide sequence considerably from one another as a function of significant sequence variability among the large number of possible TCR or BCR variable (V) and joining (J) region polynucleotides. Sequences of individual template oligonucleotide species can also vary from one another as a function of sequence differences in U1, U2, B (B1, B2 and B3) and R oligonucleotides that are included in a particular template within the diverse plurality of templates.

In certain embodiments, V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of template oligonucleotide sequences V comprises a unique oligonucleotide sequence. In embodiments where cells other than T cells or B cells are amplified and sequenced, the "V" in formula I corresponds to the biological template that is amplified by the forward primer(s) in the reaction.

In some embodiments, J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of template oligonucleotide sequences J comprises a unique oligonucleotide sequence. In embodiments where cells other than T cells or B cells are amplified and sequenced, the "J" in formula I corresponds to the biological template that is amplified by the reverse primer(s) in the reaction.

U1 and U2 can be each either nothing or each comprise an oligonucleotide having, independently, a sequence that is selected from (i) a universal adaptor oligonucleotide sequence, and (ii) a sequencing platform-specific oligonucleotide sequence that is linked to and positioned 5' to the universal adaptor oligonucleotide sequence.

B1, B2 and B3 can be each either nothing or each comprise an oligonucleotide B that comprises a first and a second oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 contiguous nucleotides (including all integer values therebetween), wherein in each of the plurality of template oligonucleotide sequences B comprises a unique oligonucleotide sequence in which (i) the first barcode sequence uniquely identifies the unique V oligonucleotide sequence of the template oligonucleotide and (ii) the second barcode sequence uniquely identifies the unique J oligonucleotide sequence of the template oligonucleotide.

X can be either nothing or comprises a restriction enzyme recognition site that comprises an oligonucleotide sequence that is absent from V, J, U1, U2, B1, B2 and B3.

The template compositions can also include random (R) sequences of length N. Random sequences R can include 2, 3, 4, 5, 6, 7, 8, 9, 10, 11, or more random contiguous nucleotides in each template composition and can be unique to each template composition. There can be one or more R sequences in each synthetic template composition. The random sequences may be inserted in various sections between or within the components in the general formula I (5'-U1-B1-V-B2-X-B3-J-B4-U2-3') and be of various lengths in size. For example, the general formula can be 5'-U1-B1-V-R-B2-X-B3-J-B4-U2-3' and R can be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 70, 80, 90, 100, 200, 300, 300, 500 or more contiguous nucleotides. The random sequence can be used to uniquely identify each specific paired V-J combination or to quantify or estimate the number of molecules in a sample. Each unique random sequence identifies a single molecule comprising a paired V-J combination.

Methods of the invention include using the synthetic template compositions for determining non-uniform nucleic acid amplification potential among members of a set of oligonucleotide amplification primers that are capable of amplifying productively rearranged DNA encoding one or a plurality of adaptive immune receptors in a biological sample that comprises DNA from lymphoid cells of a subject. The method can include the step of amplifying DNA of a template composition for standardizing amplification efficiency of an oligonucleotide primer set in a multiplex polymerase chain reaction (PCR) that comprises (i) the template composition (I) described above and (ii) an oligonucleotide amplification primer set that is capable of amplifying productively rearranged DNA encoding one or a plurality of adaptive immune receptors in a biological sample that comprises DNA from lymphoid cells of a subject. In some embodiments, each template oligonucleotide in the plurality of template oligonucleotides is present in a substantially equimolar amount.

The primer set can include: (1) in substantially equimolar amounts, a plurality of V segment oligonucleotide primers that are each independently capable of specifically hybridizing to at least one polynucleotide encoding an adaptive immune receptor V-region polypeptide or to the complement thereof, wherein each V segment primer comprises a nucleotide sequence of at least 15 contiguous nucleotides that is complementary to at least one functional adaptive immune receptor V region-encoding gene segment and wherein the plurality of V segment primers specifically hybridize to substantially all functional adaptive immune receptor V region-encoding gene segments that are present in the template composition, and (2) in substantially equimolar amounts, a plurality of J segment oligonucleotide primers that are each independently capable of specifically hybridizing to at least one polynucleotide encoding an adaptive immune receptor J-region polypeptide or to the complement thereof, wherein each J segment primer comprises a nucleotide sequence of at least 15 contiguous nucleotides that is complementary to at least one functional adaptive immune receptor J region-encoding gene segment and wherein the plurality of J segment primers specifically hybridize to substantially all functional adaptive immune receptor J region-encoding gene segments that are present in the template composition.

The V segment and J segment oligonucleotide primers are capable of promoting amplification in the multiplex polymerase chain reaction (PCR) of substantially all template oligonucleotides in the template composition to produce a multiplicity of amplified template DNA molecules, the multiplicity of amplified template DNA molecules being sufficient to quantify diversity of the template oligonucleotides in the template composition, and wherein each amplified template DNA molecule in the multiplicity of amplified template DNA molecules is less than 1000, 900, 800, 700, 600, 500, 400, 300, 200, 100, 90, 80 or 70 nucleotides in length.

The method also includes steps of: (b) sequencing all or a sufficient portion of each of the multiplicity of amplified template DNA molecules to determine, for each unique template DNA molecule in the multiplicity of amplified template DNA molecules, (i) a template-specific oligonucleotide DNA sequence and (ii) a relative frequency of occurrence of the template oligonucleotide; and (c) comparing the relative frequency of occurrence for each unique template DNA sequence from the template composition, wherein a non-uniform frequency of occurrence for one or more template DNA sequences indicates non-uniform nucleic acid amplification potential among members of the set of oligonucleotide amplification primers. The amounts for each V segment and J segment primer set used in subsequent amplification assays can be adjusted to reduce amplification bias across the primer sets based on the relative frequency of occurrence for each unique template DNA sequence in the template composition.

Further description about bias control compositions and methods are provided in U.S. Provisional Application No. 61/726,489, filed Nov. 14, 2012, U.S. Provisional Application No. 61/644,294, filed on May 8, 2012, U.S. Provisional Application 61/949,069 filed on Mar. 6, 2014, and PCT/US2013/040221, filed on May 8, 2013, PCT/US2013/045994 (WO/2013/188831), filed on Jun. 14, 2013, and Carlson et al. Nature Communications. 2013; 4:2680, which are incorporated by reference in their entireties.

In some embodiments, multiplex PCR assays can result in problems with identifying and sequencing targets that occur in very low copy numbers. This may not be ideal for a number of reasons, foremost is that many sequencing reads would be generated for the more prevalent targets in the input material for each sequencing read observed from the rarer targets. If a certain sequencing coverage for the rare targets is required, this could mandate immense over-sequencing of the common targets, which would in turn lead to a tremendous inflation in the costs associated with running the assay.

The present disclosure presents methods that may be used to mitigate the underrepresentation of low frequency amplicons. The disclosure sets forth the use of two primers (forward, reverse, or both) at each position in place of a single primer at each position. In some embodiments, the two primers have identical gene-specific sequences, but comprise different universal tags. In some embodiments, the two primers share at least 95%, 96%, 97%, 98%, or 99% identify with one another or the reverse complement. In some embodiments, the two primers differ by no more than 5, 4, 3, 2, or 1 nucleotides in sequence length and/or identity.

In some embodiments, only two universal tags are used across all primers in the multiplex amplification; one tag for each primer in the pair of said two primers.

In one embodiment, assuming Gene 1, Gene 2, and Gene 3 transcripts are targets in the amplification, and further assuming that Gene 1 transcripts occur at a 1:10 ratio to each of Gene 2 and Gene 3 transcripts, the multiplex primers for amplifying all three gene transcripts comprises (1) 100% primer Gene 1 with universal tag A; (2) 10% primer Gene 2 with universal tag A, and 90% primer Gene 2 with universal tag B; and (3) 10% primer Gene 3 with universal tag A, and 90% primer Gene 3 with universal tag B. The resulting product of this amplification produces amplicons of Genes 1, 2, and 3 comprising universal tag A at a 1:1:1 ratio. The resulting amplicons are then mixed with primers that comprise a universal sequencing adaptor, wherein the primers anneal to universal tag A. Regardless of the prevalence of the transcripts, the method provides for equal sequencing coverage of the transcripts without having to waste the resources of sequencing the each of the amplicons of the transcripts of Genes 2 and 3 that are 10× more prevalent than the amplicons of the transcripts of Gene 1.

In some embodiments, the number of unique targets amplified may be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1,000, 3,000, 6,000, 9,000, 12,000, or 15,000.

In general, a multiplex PCR system can use 2, 3, 4, 5, 6, 7, 8, 9, 10, 11, 12, 13, 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments, 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to or is complementary to a sequence corresponding to one or more V region segments. The multiplex PCR system also uses at least 2, 3, 4, 5, 6, or 7, and in certain embodiments, 8, 9, 10, 11, 12 or 13 reverse primers, or 14, 15, 16, 17, 18, 19, 20, 21, 22, 23, 24, or 25 or more primers, in which each reverse primer specifically hybridizes to or is complementary to a sequence corresponding to one or more J region segments. In some embodiments, each reverse J primer is specific to a different J gene segment. In other embodiments, there is no common J primer that binds to all J gene segments.

Multiplex PCR assays can result in a bias in the total numbers of amplicons produced from a sample, given that certain primer sets are more efficient in amplification than others. Multiplex PCR poses unique challenges because all primers must function under the same reaction conditions, which should not only allow each primer to anneal to its true target sequence, but minimize non-specific amplification and avoid production of primer-dimers.

Sequencing

Sequencing can be performed using any of a variety of available high throughput sequencing machines and systems.

DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, nanopore sequencing, chemical-sensitive field effect transistor array sequencing, or sequencing by electron microscope, and SOLiD sequencing. Sequencing of separated molecules has been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. Thus, these sequencing approaches can be used to study the repertoire of T-cell receptor (TCR) and/or B-cell receptor (BCR).

Certain sequencing technologies require specific DNA sequences on both ends of the target molecules to be sequenced. These sequences are added either by synthesis using PCR or by ligation. The sample preparation steps can differ significantly across sequencing technologies. One instrument, the 454 sequencer (Roche) provides long reads which are amenable to capturing full-length IgH cDNA sequences including all somatic hypermutations; however, the 454 sequencer has a high cost per read and high rate of insertions and deletions (indels) from homopolymers. The indels from homopolymers are a large problem for sequencing TCRs and BCRs because the D segments often contain homopolymer stretches of G nucleotides. The Ion Torrent sequencing technology (Life Technologies) has a similar drawback of high indel rates. However, the Ion technology is very fast and inexpensive. The MiSeq and HiSeq 2500 technology (Illumina) is also fast and inexpensive. Although, Illumina's technology has much less issues with indels, the errors can be position dependent (higher as read length increases). As sequencing of TCR and BCRs begin from similar nucleotide positions, the higher error rates are consistently in the same regions. Additionally, both the Ion and Illumina technology have read lengths that are presently too short to cross the full TCR or BCR genes. However, sequencing technology is improving very rapidly, with longer, more accurate, and less expensive reads.

In a preferred embodiment, sequencing is achieved using a reversible-terminator sequencing by synthesis technology. Illustrative sequence by synthesis systems include, but are not limited to, the Illumina Genome Analyzer, MiSEQ, HiSEQ, and associated instruments (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.). In a preferred embodiment, the sequence by synthesis system used for sequencing is a MiSeq or HiSeq 2500 technology (Illumina).

In some embodiments, amplicons are amplified by PCR with a set of tailing primers that include sequencing oligonucleotides. These sequencing oligonucleotides are complimentary to sequencing platform-specific oligonucleotide sequences used on the sequencing platform. These sequencing oligonucleotides can be specific to a single-molecule sequencing technology, for example, the HiSeq™, MiSeq™, or GeneAnalyzer™-2 (GA-2) systems (Illumina, Inc., San Diego, Calif.) or another suitable sequencing suite of instrumentation, reagents and software. Inclusion of sequencing platform-specific oligonucleotide sequences permits direct quantitative sequencing of the amplicons, using a nucleotide sequencing methodology such as the HiSeq™ or GA2 or equivalent.

Exemplary sequencing oligonucleotides are described in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. Ser. No. 13/217,126, U.S. Ser. No. 12/794,507, WO/2010/151416, WO/2011/106738 (PCT/US2011/026373), WO2012/027503 (PCT/US2011/049012), U.S. Ser. No. 61/550,311, U.S. Ser. No. 61/569,118, and PCT/US2013/045994 (WO/2013/188831), filed on Jun. 14, 2013, which are incorporated by reference in their entireties.

The sequencing technique used in the methods of the invention can generate least 1000 reads per run, at least 10,000 reads per run, at least 100,000 reads per run, at least 500,000 reads per run, or at least 1,000,000 reads per run. The sequencing technique used in the methods of the invention can generate about 30 bp, about 40 bp, about 50 bp, about 60 bp, about 70 bp, about 80 bp, about 90 bp, about 100 bp, about 110 bp, about 120 bp, about 150 bp, about 200 bp, about 250 bp, about 300 bp, about 350 bp, about 400 bp, about 450 bp, about 500 bp, about 550 bp, or about 600 bp per read. The sequencing technique used in the methods of the invention can generate at least 30, 40, 50, 60, 70, 80, 90, 100, 110, 120, 150, 200, 250, 300, 350, 400, 450, 500, 550, or 600 bp per read.

In some embodiments, bias-controlled V segment and J segment gene primers are used to amplify rearranged V(D)J segments to produce a plurality of amplicons for high throughput sequencing at ~20× coverage. Coverage means the number of copies sequenced of each synthetic template.

Processing Sequence Data

As presently disclosed, there are provided methods for analyzing the sequences of the diverse pool of uniquely rearranged CDR3-encoding regions that are generated using the compositions and methods that are described herein. As described above, amplification bias can be corrected using bias control synthetic templates.

Both PCR amplification and high throughput sequencing methods generate errors in the resultant sequences. The PCR errors can propagate, with the potential for errors to compound at each PCR cycle. Fortunately, these compound errors effect an exponentially smaller fraction of the total reads at each step. Effectively, the PCR errors can be modeled as a phylogenetic tree. Since these trees do not undergo selection, the number of elements strictly decreases along each branch. And, the PCR error rate is sufficiently small that the probability of multiple errors in the same molecule at a given cycle is negligible. So, each branch of the tree represents a single nucleotide change.

Sequencing errors are highly machine specific. The primary strategy for correcting errors is the use of redundancy. As long as any particular type of error is rare, then sequencing multiple copies from the same original template allows accurate error correction using parsimony. The key is to identify which sequence reads originated from the same template by clustering or coalescing. The step of clustering or coalescing is a process of combining sequence reads with error rates (for example, from sequencing and/or amplification errors) to produce clonotypes that are correct with a high degree of likelihood, such as with a 99% confidence level.

Although, historically this was very difficult, the improved accuracy of the sequencing technology has vastly simplified this problem. A large fraction of sequences are error free, which allows for easy identification of the primary nodes in each cluster, by simply identifying the sequences with multiple copies in the data. For the case of larger clones, there is a probability that the same error occurs multiple times, either independently with the same sequencing errors, or dependently through PCR. So, an additional rule is added for clustering, which simply asserts that if two primary nodes are different by a single nucleotide and one node is far larger than the other, the smaller node is moved into the tree anchored by the larger primary node. Then, all additional sequences are placed into the tree structure based on distance to the primary nodes. In the corrected output, each primary node is the sequence of a unique clone, and the copy number, or relative abundance, is the number of sequence reads in the tree. The different sequencing technologies determine the choice of distance metric. Additionally, the software associated with the sequencing technologies report accuracy rates at each base, and this information can be incorporated into the clustering algorithm to improve accuracy.

In some embodiments, the sequencing results are experimentally validated. Each processing algorithm makes an assumption about the likely sources of error and their form, so these assumptions must be tested. This requires a known input library. Given a known starting set of templates, they can be run through the full protocol and the output can be compared back to input sequences. The starting template can either be a synthetic set of templates, or a well studied library.

In some embodiments, the sequenced reads are filtered for those including CDR3 sequences. Sequencer data processing involves a series of steps to remove errors in the primary sequence of each read, and to compress the data. A complexity filter removes approximately 20% of the sequences that are misreads from the sequencer. Then, sequences were required to have a minimum of a six base match to both one of the TCR or IG J-regions and one of the TCR or IG V-regions. Applying the filter to the control lane containing phage sequence, on average only one sequence in 7-8 million passed these steps. Finally, a nearest neighbor algorithm is used to collapse the data into unique sequences by merging closely related sequences, in order to remove both PCR error and sequencing error.

In some embodiments, methods are used for estimating the true distribution of specific clonotypes (e.g., a TCR or IG having a uniquely rearranged CDR3 sequence) in blood or in a sample derived from other peripheral tissue or bodily fluid. For example, the ratio of sequences in the PCR product can be derived by working backward from the sequence data before estimating the true distribution of clonotypes (e.g., unique clonal sequences) in the blood. For each sequence observed a given number of times in the data herein, the probability that that sequence was sampled from a particular size PCR pool is estimated. Because the CDR3 regions sequenced are sampled randomly from a massive pool of PCR products, the number of observations for each sequence are drawn from Poisson distributions. The Poisson parameters are quantized according to the number of T cell genomes that provided the template for PCR. A simple Poisson mixture model both estimates these parameters and places a pairwise probability for each sequence being drawn from each distribution. This is an expectation maximization method, which reconstructs the abundances of each sequence that was drawn from the blood.

In some embodiments, to estimate the total number of unique adaptive immune receptor CDR3 sequences that are present in a sample, a computational approach employing the "unseen species" formula may be employed (Efron and Thisted, 1976 *Biometrika* 63, 435-447). This approach estimates the number of unique species (e.g., unique adaptive immune receptor sequences) in a large, complex population (e.g., a population of adaptive immune cells such as T cells or B cells), based on the number of unique species observed in a random, finite sample from a population (Fisher et al., 1943 *J. Anim. Ecol.* 12:42-58; Ionita-Laza et al., 2009 *Proc. Nat. Acad. Sci. USA* 106:5008). The method employs an expression that predicts the number of "new" species that would be observed if a second random, finite and identically sized sample from the same population were to be analyzed. "Unseen" species refers to the number of new adaptive immune receptor sequences that would be detected if the steps of amplifying adaptive immune receptor-encoding sequences in a sample and determining the frequency of occurrence of each unique sequence in the sample were repeated an infinite number of times. By way of non-limiting theory, it is operationally assumed for purposes of these estimates that adaptive immune cells (e.g., T cells, B cells) circulate freely in the anatomical compartment of the subject that is the source of the sample from which diversity is being estimated (e.g., blood, lymph, etc.).

To apply this formula, unique adaptive immune receptors (e.g., TCRβ, TCRα, TCRγ, TCRδ, IgH) clonotypes takes the place of species. The mathematical solution provides that for S, the total number of adaptive immune receptors having unique sequences (e.g., TCRβ, TCRγ, IgH "species" or clonotypes, which may in certain embodiments be unique CDR3 sequences), a sequencing experiment observes $x_s$ copies of sequence s. For all of the unobserved clonotypes, $x_s$ equals 0, and each TCR or Ig clonotype is "captured" in the course of obtaining a random sample (e.g., a blood draw) according to a Poisson process with parameter $\lambda_s$. The number of T or B cell genomes sequenced in the first measurement is defined as 1, and the number of T or B cell genomes sequenced in the second measurement is defined as t.

Because there are a large number of unique sequences, an integral is used instead of a sum. If $G(\lambda)$ is the empirical distribution function of the parameters $\lambda_1, \ldots, \lambda_S$, and $n_x$ is the number of clonotypes (e.g., unique TCR or Ig sequences, or unique CDR3 sequences) observed exactly x times, then the total number of clonotypes, i.e., the measurement of diversity E, is given by the following formula (I):

$$E(n_x) = S \int_0^\infty \left(\frac{e^{-\lambda}\lambda^x}{x!}\right) dG(\lambda). \tag{I}$$

Accordingly, formula (I) may be used to estimate the total diversity of species in the entire source from which the identically sized samples are taken. Without wishing to be bound by theory, the principle is that the sampled number of clonotypes in a sample of any given size contains sufficient information to estimate the underlying distribution of clonotypes in the whole source. The value for $\Delta(t)$, the number of new clonotypes observed in a second measurement, may be determined, preferably using the following equation (II):

$$\Delta(t) = \sum_x E(n_x)_{msmt1+msmt2} - \sum_x E(n_x)_{msmt1} = S \int_0^\infty e^{-\lambda}(1-e^{-\lambda t}) dG(\lambda) \tag{II}$$

in which msmt1 and msmt2 are the number of clonotypes from measurements 1 and 2, respectively. Taylor expansion of $1-e^{-\lambda t}$ and substitution into the expression for $\Delta(t)$ yields:

$$\Delta(t) = E(x_1)t - E(x_2)t^2 + E(x_3)t^3 - \tag{III}$$

which can be approximated by replacing the expectations ($E(n_x)$) with the actual numbers sequences observed exactly x times in the first sample measurement. The expression for $\Delta(t)$ oscillates widely as t goes to infinity, so $\Delta(t)$ is regularized to produce a lower bound for $\Delta(\infty)$, for example, using the Euler transformation (Efron et al., 1976 *Biometrika* 63:435).

In one example, using the numbers observed in a first measurement of TCRβ sequence diversity in a blood sample, this formula (II) predicted that $1.6*10^5$ new unique sequences should be observed in a second measurement. The actual value of the second measurement was $1.8*10^5$ new TCRβ sequences, which suggested according to non-limiting theory that the prediction provided a valid lower bound on total TCRβ sequence diversity in the subject from whom the sample was drawn.

Additional description about the unseen species model and processing sequence data are described in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. Ser. No. 13/217,126, U.S. Ser. No. 12/794,507, WO/2010/151416, WO/2011/106738 (PCT/US2011/026373), WO2012/027503 (PCT/US2011/049012), U.S. Ser. No. 61/550,311, and U.S. Ser. No. 61/569,118, which are incorporated by reference in their entireties.

In certain embodiments, after correcting for sequencing errors via a clustering algorithm, CDR3 segments can be annotated according to the International ImMunoGeneTics collaboration. See Lefranc, M.-P., Giudicelli, V., Ginestoux, C., Jabado-Michaloud, J., Folch, G., Bellahcene, F., Wu, Y., Gemrot, E., Brochet, X., Lane, J., Regnier, L., Ehrenmann, F., Lefranc, G. and Duroux, P. IMGT®, the International ImMunoGeneTics Information System®. Nucl. Acids Res, 37, D1006-D1012 (2009); doi:10.1093/nar/gkn838. PMID: 18978023; Lefranc, M.-P., IMGT, the International ImMunoGeneTics Information System. Cold Spring Harb Protoc.

2011 Jun. 1. 2011(6). pii: pdb.top115. doi: 10.1101/pdb.top115. PMID: 21632786.

Clonotype Determination

In some embodiments, a clonotype is defined when at least two identical sequence reads are obtained. Briefly, after exclusion of low quality reads, sequence data can be analyzed to determine the clonotype sequences including mapping to germline V and J consensus sequences. In one embodiment, the sample index sequences were used to identify which of the sequences originate from which of the pooled samples. Sequences whose index are not a perfect match to one of the indices used in a specific run are excluded. Next the forward read is used to map the J segment. Since all the sequences started from the same position of the J segments, all the J segments started at a predefined sequencing position. The first 25 bp of the J segments are used to map the J segment. Any read with more than 5 high quality mismatches to the known J segments are excluded from further analysis.

After J segment identification, V segments are mapped. The reverse read is used for this purpose. First, the V primer is mapped and excluded. Thereafter, the next 70 bases of the reverse read are mapped to the known V segments. Reads that do not map to J and V segments are excluded. The next step in mapping involves identifying the frame that related the forward and reverse reads and this allows a continuous sequence from J to V to be constructed. This is done using the last 15 bases of the forward read which are reliably within the V segment regardless of NDN length. While these bases could be of relatively lower sequence quality as they are at the terminal end of a long read, they can be used to map within a single identified V segment in order to identify the position at which the two reads could be joined. Finally, the known V and J sequences to which the reads map are used to identify the point in the forward read at which the sequences at the junctions diverged from these mapped segments.

Other methods known to one of skill in the art can be used to identify and remove sequence errors and cluster sequences.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Method of Determining Total Number of Sampled Genomes Using Biological and Synthetic Templates In this example, the methods depicted in FIG. 1 were used to determine the number of total input biological TCRB molecules in a sample and the total input genomes in the sample. The hypothesis of whether sequencing only a portion of synthetic and biologic housekeeping templates with the methods depicted in FIG. 1 can accurately estimate the total number of input templates in the same way as sequencing all of the synthetic and biologic housekeeping templates was tested.

In a first experiment, a composition comprising genomic biological templates and synthetic templates was generated. The genomic biological templates (i.e., genomic DNA or gDNA) were isolated from PBMCs from two individuals, and included TCRB CDR3 rearranged genes and housekeeping genes ER Membrane Protein Complex Subunit 7 (EMC7), Ras-Related Protein Rab-7a (RAB7A) and Receptor Accessory Protein 5 (REEP5). The synthetic templates were generated for each of the TCRB CDR3 rearranged gene segments and the housekeeping gene (HKG) segments. Approximately 6000 molecules of synthetic housekeeping genes were added to the tube, such that there were approximately 2000 molecules each of EMC7, RAB71, and REEP5. Approximately 130 gblock synthetic TCRB molecules and approximately 8000 vblock TCRB molecules were added per rxn for a total of about 8130 TCRB synthetic templates per reaction.

Further, the synthetic TCRB CDR3 templates and the synthetic HKG templates each comprised a unique random sequence that was 8 base pairs in length (N8). The N8 sequence allowed for quantification of each unique molecule in the sample. The synthetic HKG templates further comprised an additional synthetic sequence, designated SYN, that was not complementary to any other sequence within the composition. It should be noted that for this experiment, the N8 sequence was incorporated into both the synthetic HKG template and the separate SYN sequence. However, only the N8 sequence in the SYN sequences were utilized for calculations. It is also possible to use an HKG-SYN synthetic template where the N8 sequence is present in only the SYN sequence.

In a first multiplex PCR assay, the following primer sets were added to the composition described above: 1.) a set of primers that included a pGEX tail and sequence complementary to the TCRB biological and synthetic templates; 2.) a set of primers that included a pGEX tail and sequence complementary to the HKG biological and synthetic templates (50% of primers for HKG); 3.) a set of primers that include a non-pGex tail and sequence complementary to the HKG (50% of primers for HKG); and 4.) a set of primers that include a pGEX tail and sequence complementary to the SYN portion of the HGK synthetic molecules.

The first multiplex PCR produced the following amplicons: 1.) Amplicons comprising a biological TCRB sequence and pGEX sequences on the 5' and 3' ends; 2.) Amplicons comprising a SYN sequence and pGEX sequences on the 5' and 3' ends; 3.) Amplicons comprising a biologic or synthetic HKG sequence and pGEX sequences on the 5' and 3' ends; 4.) Amplicons comprising a biologic or synthetic HKG sequence and non-pGEX sequences on the 5' and 3' ends; 5.) Amplicons comprising a biologic or synthetic HKG sequence, non-pGEX sequence on the 5' end and pGEX on the 3' end; and 6.) Amplicons comprising a synthetic or biologic HKG sequence, pGEX sequence on the 5' and non-pGEX sequence on the 3' end. As a result, approximately 25% of the resulting biologic and synthetic HKG amplicons included pGEX adaptors on the 5' and 3' end.

Subsequently, a second tailing PCR was performed on the resulting amplicons using primers that include a sequence complementary to the pGEX sequence and an Illumina sequencing adaptor. Only the amplicons with the pGEX sequence on both the 5' and 3' end of the molecule are amplified.

The amplicons from the second PCR were sequenced using high-throughput sequencing described herein. The method comprised sequencing the TCRB CDR3 biological templates at high sequence coverage and the biological HKG genes (EMC7, RAB7A and REEP5) at low sequence coverage and then using the sequence reads obtained to determine the total number of TCRB and HKG templates in the starting sample.

The number of input HKG biological templates was calculated as follows: (number of sequencing reads from biological HKG templates)/((number of sequencing reads from synthetic HKG templates)/(number of unique random oligonucleotide tag sequences observed in SYN molecules)).

Experiment 2: In another experiment, a multiplex PCR was performed where all of the amplicons included the same adaptor sequences, such that all of the amplicons were sequenceable. Again, approximately 6000 molecules of synthetic housekeeping genes were added to the tube, such that there were approximately 2000 molecules each of EMC7, RAB71, and REEP5.

The following primers were used:
1.) One set of primers that included a pGEX tail and can amplify TCRB biological and synthetic templates; 2.) One set of primers that include a pGEX tail and can amplify HKG biological and synthetic templates; and 3.) One set of primers that include a pGEX tail and can amplify SYN synthetic templates.

The resulting amplicons in the assay had a pGEX sequence and were as follows:
1.) Amplicons comprising a biological TCRB sequence and pGEX sequences on the 5' and 3' ends;
2.) Amplicons comprising a synthetic or a biologic HKG sequence and pGEX sequences on the 5' and 3' ends; and
3.) Amplicons comprising a SYN sequence and pGEX sequences on the 5' and 3' ends.

A second tailing PCR was then performed on the resulting amplicons using primers that include a sequence complementary to the pGEX sequence and an Illumina sequencing adaptor.

The amplicons from the second PCR were sequenced using high-throughput sequencing described herein. In this assay, sequencing of the TCRB locus and the HKG genes (EMC7, RAB7A and REEP5) were both at high sequence coverage.

The number of input HKG biological templates was calculated as follows: (number of sequencing reads from biological HKG templates)/((number of sequencing reads from synthetic HKG templates)/(number of unique random oligonucleotide tag sequences observed in SYN templates)).

Figure 2:
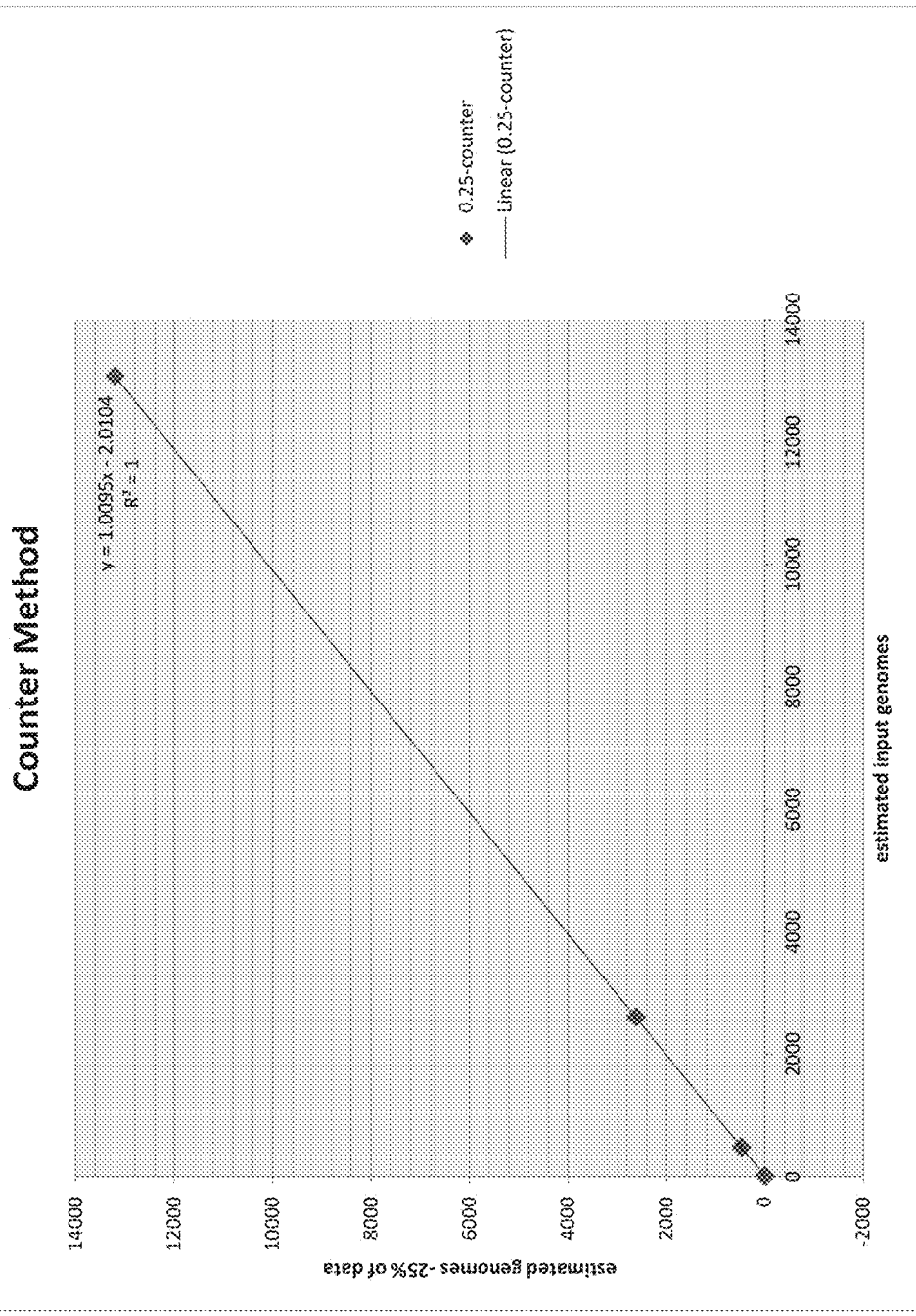
FIG. 2 illustrates the data from the two down-sampling experiments. On the X axis, the estimated number of genomes as calculated when sequencing all input molecules is shown. On the Y axis, the estimated number of genomes as calculated after only sequencing 25% of the molecules added to the PCR reaction. The linear correlation indicates that sampling only 25% of the input synthetic HKG molecules provides an accurate estimation of the total input genome molecules, similar to the estimated number of input genomes from sequencing all of the synthetic HKG molecules in the sample.

The data from the two experiments is shown in FIG. 2. On the X axis, the estimated number of genomes as calculated when sequencing all input molecules is shown. On the Y axis, the estimated number of genomes as calculated after only sequencing 25% of the molecules added to the PCR reaction. The linear correlation indicates that sampling only 25% of the input synthetic HKG molecules provides an accurate estimation of the total input genome molecules, similar to the estimated number of input genomes from sequencing all of the synthetic HKG molecules in the sample.

Additional experiments were performed using the same methods described above, except the concentrations of primers for a particular adaptor were varied in order to test the effect of down-sampling in this manner.

In one experiment, 30% of the primers in the first PCR assay had an alternative adaptor (not complementary to the adaptor sequence in the second set of primers used in the second tailing reaction as described above). This resulted in 9% of the amplicons having the correct adaptor on the 5' and 3' ends (down-sampling of 9%=$0.3^2$) as opposed to the 25% noted in the experiments above.

In another experiment, 20% of the primers in the first PCR assay had an alternative adaptor. This resulted in 4% of the amplicons having the correct adaptor on the 5' and 3' ends (down-sampling of 4%=$0.2^2$).

Figure 3:
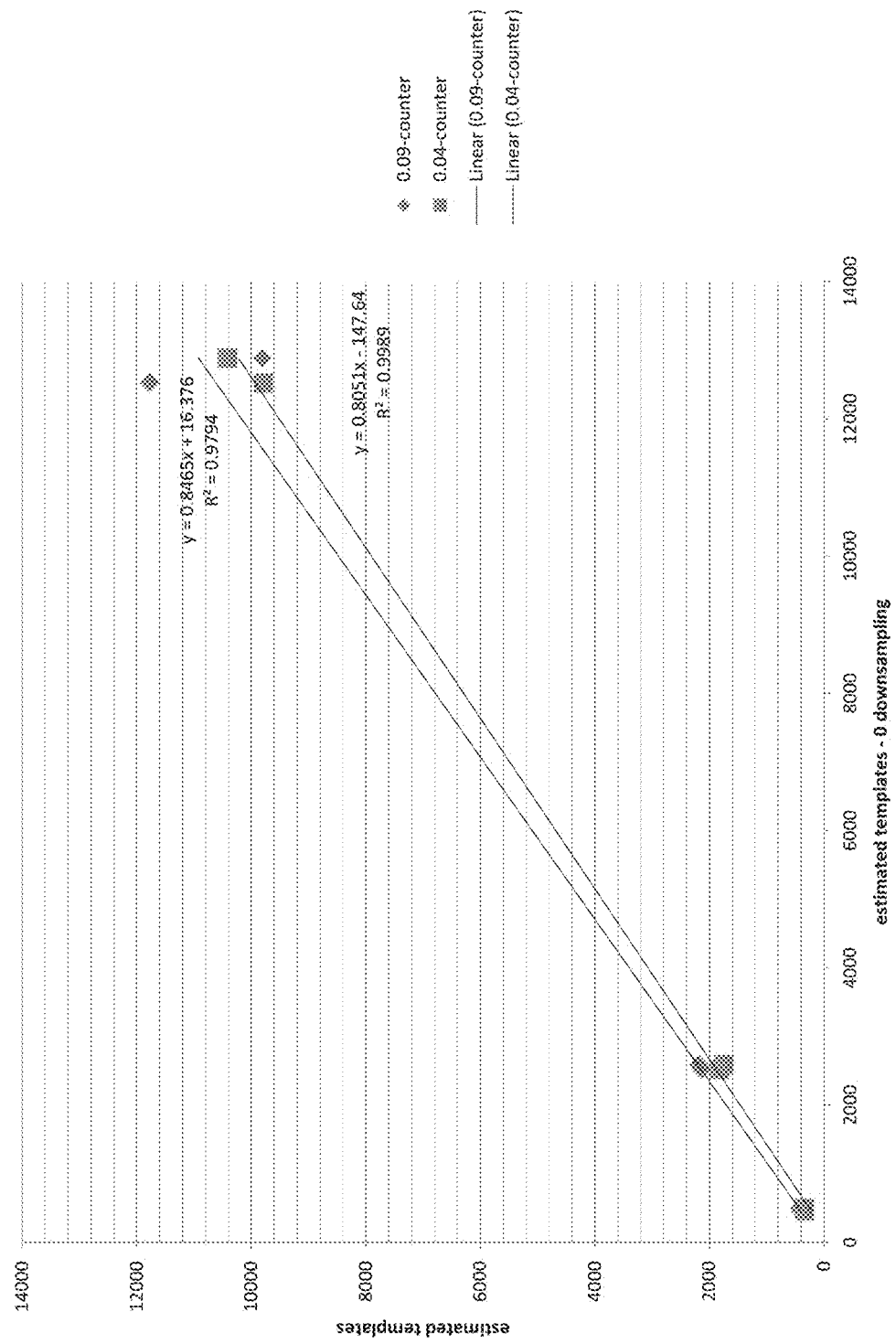
FIG. 3 illustrates data from two down-sampling experiments.

These two down-sampling experiments were compared to the data from an assay where all of the primers had the same adaptor sequence and all of the resulting amplicons could be sequenced. FIG. 3 shows the number of estimated templates using all templates (no down-sampling) compared with the number of estimated templates using 30% of the primers with the correct adaptor sequence (0.09-counter; diamonds) or using 20% of the primers with the correct adaptor sequence (0.04-counter; squares). The linear correlation shows that sampling only 30% or 20% of the input synthetic HKG molecules provides an accurate estimation of the total input genome molecules, similar to the estimated number of input genomes from sequencing all of the synthetic HKG molecules in the sample.

In three additional independent experiments, 20% of the primers in the first PCR assay had an alternative adaptor (not complementary to the adaptor sequence in the second set of primers used in the tailing reaction). This resulted in 4% of the amplicons having the correct adaptor on the 5' and 3' ends (down-sampling of 4%=$0.2^2$).

Figure 4:
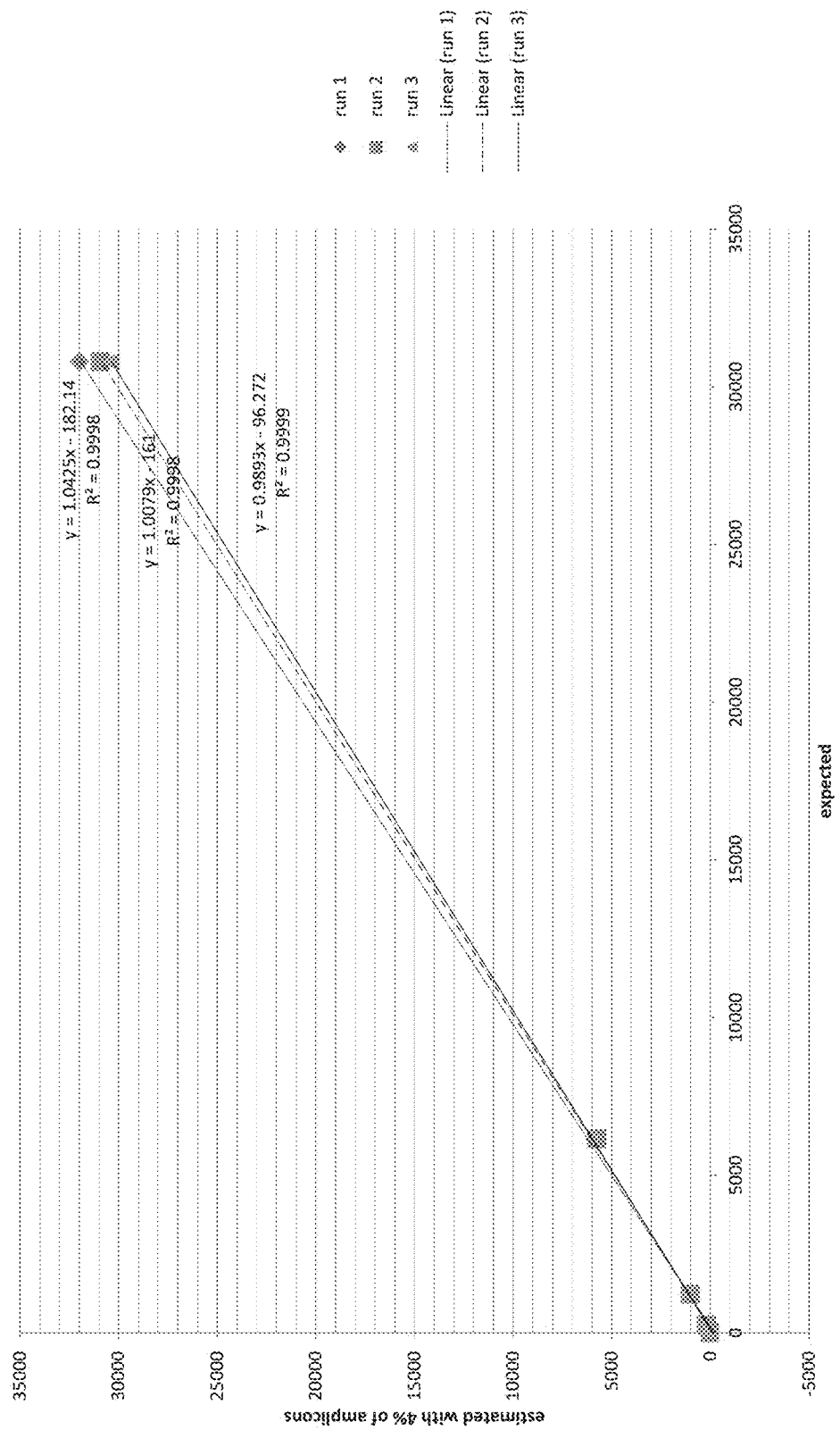
FIG. 4 illustrates the template estimates calculated using three down-sampling experiments compared to the expected number of observable templates.

The template estimates calculated using these three down-sampling experiments were compared to the expected number of observable templates. FIG. 4 shows the number of estimated templates (X-axis) compared with the number of estimated templates using 20% of the primers with the correct adaptor sequence for each experiment (run 1, run 2, run 3). Each experiment used a separate set of DNA and a separate PCR and sequencing setup. The linear correlation shows that sampling only 20% of the input synthetic and biologic HKG molecules provides an accurate estimation of the total input genome molecules, similar to the estimated number of input genomes from sequencing all of the synthetic HKG molecules in the sample.

Example 2: Method of Increasing Copy Number of Amplified Targets Over Naïve Multiplex PCR Obtain a sample of starting material comprising mRNA transcripts. Prepare an assay using a multiplex of primers that amplify multiple targets from the starting material, e.g., GeneA, GeneB, GeneC, GeneD, GeneE. The aforementioned gene designations are merely exemplary and each may represent a separate gene or gene variant found in a sample.

GeneA transcripts and GeneB transcripts are determined to be present in the mRNA sample at a ratio of 1:10.

Utilizing a naïve approach to capture at least 100 reads from each of GeneA and GeneB transcripts, the targets that occur in the greatest frequency would require immense over-sequencing, which translates to greatly inflated costs to capture at least 100 amplicons from the considerably less common transcripts of GeneA.

The present approach utilizes two primers (forward, reverse, or both) in lieu of the single primer at each position that would be used in the naïve multiplex PCR. Each of these two primers have similar or identical target-specific sequences, e.g., two forward primers targeting the same gene, but would have two different universal tags attached. The two different universal tags are consistent across all primers in the multiplex reaction(s).

The primers comprise a first set of primers and a second set of primers. The first set of primers for each target are identical to the second set of primers with the exception of universal tags. The first set of primers for each target comprise a first universal tag (universal tag X), and the second set of primers for each target comprise a second universal tag (universal tag Y).

A first PCR is performed on the sample by combining (1) a mixture of primers to GeneB that comprise 10% universal tag X and 90% tag Y, and (2) primers to GeneA that comprise 100% universal tag X. A second PCR is performed on the amplicons of the first PCR by utilizing primers that anneal to universal tag X and add sequencing adaptors only to amplicons comprising tag X.

The result is a pool of amplicons of transcripts of GeneA and GeneB, wherein the amplicons comprising sequencing adaptors occur at a ratio of 1:1. The result of sequencing 100 amplicons from each gene transcript that occurred in the sample at considerably different frequencies is achieved without having to spend the time and resources to sequence the thousands upon thousands of amplicons of the transcripts that occurred in the sample at the greatest frequency.

REFERENCES CITED

1. Robins H S, Campregher P V, Srivastava S K, Wacher A, Turtle C J, Kahsai O, Riddell S R, Warren E H, Carlson C S: Comprehensive assessment of T-cell receptor beta-chain diversity in alphabeta T cells. Blood 2009, 114: 4099-4107.
2. Weinstein J A, Jiang N, White R A 3rd, Fisher D S, Quake S R: High throughput sequencing of the zebrafish antibody repertoire. Science 2009, 324:807-810.
3. Boyd S D, Marshall E L, Merker J D, Maniar J M, Zhang L N, Sahaf B, Jones C D, Simen B B, Hanczaruk B, Nguyen K D et al.: Measurement and clinical monitoring of human lymphocyte clonality by massively parallel VDJ pyrosequencing. Sci Transl Med 2009, 1:12ra23.
4. Freeman J D, Warren R L, Webb J R, Nelson B H, Holt R A: Profiling the T-cell receptor beta-chain repertoire by massively parallel sequencing. Genome Res 2009, 19:1817-1824.
5. Arstila T P, Casrouge A, Baron V, Even J, Kanellopoulos J, Kourilsky P: A direct estimate of the human alphabeta T cell receptor diversity. Science 1999, 286:958-961.
6. Boyd, S. D., Gaeta, B. A., Jackson, K. J., Fire, A. Z., Marshall, E. L., Merker, J. D., Maniar, J. M., Zhang, L. N., Sahaf, B., Jones, C. D., Simen, B. B., Hanczaruk, B., Nguyen, K. D., Nadeau, K. C., Egholm, M., Miklos, D. B., Zehnder, J. L., Collins, A. M., 2010. Individual variation in the germline Ig gene repertoire inferred from variable region gene rearrangements. J. Immunol. 184, 6986.
7. Boyd, S. D., Marshall, E. L., Merker, J. D., Maniar, J. M., Zhang, L. N., Sahaf, B., Jones, C. D., Simen, B. B., Hanczaruk, B., Nguyen, K. D., Nadeau, K. C., Egholm, M., Miklos, D. B., Zehnder, J. L., Fire, A. Z., 2009. Measurement and clinical monitoring of human lymphocyte clonality by massively parallel VDJ pyrosequencing. Sci. Transl. Med. 1, 12ra23.
8. Wang, C., Sanders, C. M., Yang, Q., Schroeder Jr., H. W., Wang, E., Babrzadeh, F., Gharizadeh, B., Myers, R. M., Hudson Jr., J. R., Davis, R. W., Han, J., 2010. High throughput sequencing reveals a complex pattern of dynamic interrelationships among human T cell subsets. Proc. Natl. Acad. Sci. U.S.A. 107, 1518.
9. Warren, R. L., Freeman, J. D., Zeng, T., Choe, G., Munro, S., Moore, R., Webb, J. R., Holt, R. A., 2011. Exhaustive T-cell repertoire sequencing of human peripheral blood samples reveals signatures of antigen selection and a directly measured repertoire size of at least 1 million clonotypes. Genome Res. 21 (5), 790.
10. Weinstein, J. A., Jiang, N., White III, R. A., Fisher, D. S., Quake, S. R., 2009. High-throughput sequencing of the zebrafish antibody repertoire. Science 324, 807.
11. Freeman, J. D., Warren, R. L., Webb, J. R., Nelson, B. H., Holt, R. A., 2009. Profiling the T-cell receptor beta-chain repertoire by massively parallel sequencing. Genome Res. 19 (19), 1817.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method for quantifying the number of input genomes in a sample, comprising:
   (A) performing a first polymerase chain reaction (PCR) on a composition comprising:
      1) one or more biological nucleotide molecules from a sample obtained from a subject, wherein each biological nucleotide molecule from the one or more biological nucleotide molecules comprises two biological nucleotide sequence priming sites;
      2) a set of synthetic nucleotide molecules representing the one or more biological nucleotide molecules, wherein each synthetic nucleotide molecule in the set is present only once and comprises:
         (a) a first synthetic nucleotide sequence identical to a biological nucleotide molecule from the one or more biological nucleotide molecules from (A)(1) and comprising the same two biological nucleotide sequence priming sites as the biological nucleotide molecule from the one or more biological nucleotide molecules from (A)(1));
         (b) a barcode sequence located between the two biological nucleotide sequence priming sites;
         (c) a second synthetic nucleotide sequence that is not found in any biological nucleotide molecule from the one or more biological nucleotide molecules in (A)(1) and comprising two synthetic nucleotide sequence priming sites; and
         (d) a random oligonucleotide sequence located between the two synthetic nucleotide sequence priming sites, wherein substantially every synthetic nucleotide molecule from the set of synthetic nucleotide molecules comprises a unique random oligonucleotide sequence;
      3) a first set of primers comprising a first adapter sequence and a sequence capable of hybridizing to one of the two biological nucleotide sequence priming sites found in each biological nucleotide molecule from the one or more biological nucleotide molecules of (A)(1) and the first synthetic nucleotide sequence in the set of synthetic nucleotide molecules of (A)(2) and a second set of primers comprising a second adapter sequence or no adapter sequence and a sequence capable of hybridizing to one of the two biological nucleotide sequence priming sites found in each biological nucleotide molecule from the one or more biological nucleotide molecules of (A)(1) and the first synthetic nucleotide sequence in the set of synthetic nucleotide molecules of (A)(2), wherein the first set of primers and the second set of primers are present in equal amounts; and
      4) a third set of primers comprising the first adapter sequence and a sequence capable of hybridizing to one of the two synthetic nucleotide sequence priming sites found in the second synthetic nucleotide sequence in the set of synthetic nucleotide molecules of (A)(2), wherein the one or more biological nucleotide molecules in (A)(1) and the set of synthetic nucleotide molecules in (A)(2) are amplified with the first set of primers, the second set of primers, and the third set of primers, thereby producing a plurality of first amplicons comprising the first adapter sequence and a plurality of second amplicons comprising the second adapter sequence or no adapter sequence;
   (B) amplifying the plurality of first amplicons in a second PCR using a set of tailing primers, wherein each tailing primer comprises a sequence complementary to the first adapter sequence and a sequencing adapter oligonucleotide sequence to produce a plurality of third amplicons;
   (C) performing high throughput sequencing of the plurality of third amplicons to produce a plurality of sequence reads;
   (D) quantifying a total number of input second synthetic nucleotide sequences of (A)(2)(c) from the first PCR by counting a total number of unique random oligonucleotide sequences observed in the plurality of sequence reads;
   (E) determining a sequencing coverage for the first synthetic nucleotide sequences of (A)(2)(a) by dividing a total number of observed sequence reads containing the barcode by the total number of input second synthetic nucleotide sequences obtained in (D); and
   (F) quantifying the number of input genomes in the sample by dividing a total number of observed sequence reads from the one or more biological nucleotide molecules in (A)(1) by the sequence coverage determined in (E).

2. A method for quantifying the number of input genomes in a sample, comprising:
   (A) amplifying by a first polymerase chain reaction (PCR) a composition comprising:
      1) one or more biological nucleotide molecules from a sample obtained from a subject, wherein each biological nucleotide molecule from the one or more biological nucleotide molecules comprises two biological nucleotide sequence priming sites;
      2) a set of synthetic nucleotide molecules representing the one or more biological nucleotide molecules, wherein each synthetic nucleotide molecule in the set is present only once and comprises:
         (a) a first synthetic nucleotide sequence identical to a biological nucleotide molecule from the one or more biological nucleotide molecules from (A)(1) and comprising the same two biological nucleotide sequence priming sites as the biological nucleotide molecule from the one or more biological nucleotide molecules from (A)(1);
         (b) a barcode sequence located between the two biological nucleotide sequence priming sites;
         (c) a second synthetic nucleotide sequence that is not found in any of the one or more biological nucleotide molecules in (A)(1) and comprising two synthetic nucleotide sequence priming sites; and
         (d) a random oligonucleotide sequence located between the two synthetic nucleotide sequence priming sites, wherein substantially every synthetic nucleotide molecule from the set of synthetic nucleotide molecules comprises a unique random oligonucleotide sequence;
      3) a first set of primers comprising a first adapter sequence and a sequence capable of hybridizing to one of the two biological nucleotide sequence priming sites found in each biological nucleotide molecule from the one or more biological nucleotide molecules of (A)(1) and the first synthetic nucleotide sequence in the set of synthetic nucleotide molecules of (A)(2) and a second set of primers comprising a second adapter sequence or no adapter sequence and a sequence capable of hybridizing to one of the two biological nucleotide sequence priming sites found in each biological nucleotide molecule from the one or more the biological nucleotide molecules of (A)

(1) and the first synthetic nucleotide sequence in the set of synthetic nucleotide molecules of (A)(2), wherein the first set of primers is present at a lower amount than the second set of primers; and
4) a third set of primers comprising the first adapter sequence and a sequence capable of hybridizing to one of the two synthetic nucleotide sequence priming sites found in the second synthetic nucleotide sequence in the set of synthetic nucleotide molecules of (A)(2), wherein the one or more biological nucleotide molecules in (A)(1) and the set of synthetic nucleotide molecules in (A)(2) are amplified with the first set of primers, the second set of primers, and a third set of primers, thereby producing a plurality of first amplicons comprising the first adapter sequence and a plurality of second amplicons comprising the second adapter sequence or no adapter sequence;
(B) amplifying the plurality of first amplicons in a second PCR using a set of tailing primers, wherein each tailing primer comprises a sequence complementary to the first adapter sequence and a sequencing adapter oligonucleotide sequence to produce a plurality of third amplicons;
(C) performing high throughput sequencing of the plurality of third amplicons to produce a plurality of sequence reads;
(D) quantifying a total number of input second synthetic nucleotide sequences of (A)(2)(c) from the first PCR by counting a total number of unique random oligonucleotide sequences observed in the plurality of sequence reads;
(E) determining a sequencing coverage for the first synthetic nucleotide sequences of (A)(2)(a) by dividing a total number of observed sequence reads containing the barcode by the total number of input second synthetic nucleotide sequences obtained in (D); and
(F) quantifying the number of input genomes in the sample by dividing a total number of observed sequence reads from the one or more biological nucleotide molecules in (A)(1) by the sequence coverage determined in (E).

3. The method of claim 2, wherein the first set of primers is present at an amount or concentration 70% lower than the second set of primers.

4. The method of claim 2, wherein the first set of primers is present at an amount or concentration 80% lower than the second set of primers.

5. The method of any one of the above claims, wherein the sample comprises T cells and provides an estimate of the number of input T cell genomes, wherein the sample comprises B cells and provides an estimate of the number of input B cell genomes, or wherein the sample comprises T cells and B cells and provides an estimate of the number of input T cell and B cell genomes.

6. The method of claim 5, wherein the one or more biological nucleotide molecules in step A(1) is one or more rearranged CDR3 oligonucleotide sequences from T cell receptor (TCR) loci from T cells and/or Immunoglobulin (Ig) loci from B cells, wherein each CDR3 oligonucleotide sequence comprises a V segment and a J segment.

7. The method of any one of claims 1-4, wherein the one or more biological nucleotide molecules in step A(1) comprises one or more genomic control regions.

8. The method of claim 7, wherein the one or more genomic control regions are selected from one or more of ACTB, B2M, C1orf34, CHMP2A, GPI, GUSB, HMBS, HPRT1, PSMB4, RPL13A, RPLPO, SDHA, SNRPD3, UBC, VCP, VPS29, PPIA, PSMB2, RAB7A, REEP5 and EMC7.

9. The method of claim 8, wherein the one or more genomic control regions are PSMB2, RAB7A, PPIA, REEP5, and EMC7.

10. The method of any one of claims 1-4, wherein the random oligonucleotide sequence comprises from 4 to 50 nucleotides.

11. The method of claim 10, wherein the random oligonucleotide sequence comprises 8 nucleotides.

12. The method of claim 1, wherein the second synthetic nucleotide sequence further comprises a spacer between the sequences of (A)(2)(a) and (A)(2)(c).

13. The method of claim 12, wherein the spacer is about 200 base pairs in length.

14. The method of claim 13, wherein the spacer comprises a nucleotide sequence known to have secondary structure under conditions for PCR.

15. The method of claim 7, further comprising:
(G) amplifying by multiplex PCR, sequencing, and quantifying output reads from: (1) an additional set of biological nucleotide molecules comprising rearranged T cell receptor (TCR) loci from T cells or Immunoglobulin (Ig) loci from B cells and (2) an additional set of synthetic nucleotide molecules each comprising one TCR or Ig V segment, one TCR or Ig J or C segment, and a unique barcode which identifies said synthetic nucleotide molecules as synthetic, an internal marker oligonucleotide sequence, and a random oligonucleotide sequence, wherein each random oligonucleotide sequence comprises a unique nucleotide sequence, and wherein each synthetic nucleotide molecule comprises a unique combination of V and J or C segments;
(H) determining an amplification factor for each synthetic nucleotide molecule from the additional set of synthetic nucleotide molecules, wherein the amplification factor is represented by a total number of synthetic nucleotide molecules amplified and sequenced in step (G)(2) as evidenced by the number of sequencing reads from the additional set of synthetic nucleotide molecules divided by the total input number of unique synthetic nucleotide molecules amplified and sequenced in step (G)(2) as evidenced by the number of unique random oligonucleotide sequences observed for the additional set of synthetic nucleotide molecules; and
(I) quantifying a total number of T cells or B cells in the sample by dividing a total number of output biological sequences from step (G)(1) as evidenced by the number of sequencing reads obtained from the additional set of biological nucleotide molecules by the corresponding amplification factor from step (H).

16. The method of claim 15, wherein the sample comprises a mixture of cells comprising T cells and/or B cells and cells that are not T cells and/or B cells.

17. The method of claim 16, further comprising determining a ratio of T cells to genomic control regions in the sample by comparing the total number of T cells in the sample determined in step (I) to the total number of one or more genomic control regions determined in step (F) or determining a ratio of B cells to genomic control regions in the sample by comparing the total number of B cells in the sample determined in step (I) to the total number of one or more genomic control regions determined in step (F).

18. The method of claim 15, wherein the additional set of synthetic nucleotide molecules comprises a sequence of formula I: 5'-U1-B1-V-I-B2-N-J-B3-U2-3', wherein (i) V is an oligonucleotide sequence comprising at least 20 and not more than 1000 contiguous nucleotides of a TCR or Ig variable (V) region encoding gene sequence, or the complement thereof, and each synthetic nucleotide molecule comprises a unique V-region oligonucleotide sequence;

(ii) J is an oligonucleotide sequence comprising at least 15 and not more than 600 contiguous nucleotides of a TCR or Ig joining (J) region encoding gene sequence, or the complement thereof, and each synthetic nucleotide molecule comprises a unique J-region oligonucleotide sequence;

(iii) U1 comprises an oligonucleotide sequence that is selected from: (a) a first universal adaptor oligonucleotide sequence, and (b) a first sequencing platform oligonucleotide sequence that is linked to and positioned 5' to a first universal adaptor oligonucleotide sequence;

(iv) U2 comprises an oligonucleotide sequence that is selected from: (a) a second universal adaptor oligonucleotide sequence, and (b) a second sequencing platform oligonucleotide sequence that is linked to and positioned 3' to a second universal adaptor oligonucleotide sequence;

(v) I is an internal marker oligonucleotide sequence comprising at least 2 and not more than 100 nucleotides;

(vi) N is a random oligonucleotide sequence comprising at least 2 and not more than 100 nucleotides; and (vii) B1, B2, and B3 each independently comprise either nothing or an oligonucleotide barcode sequence of at least 2 and not more than 100 nucleotides that uniquely identify, as a pair combination, (a) said unique V-region oligonucleotide sequences; and (b) said unique J-region oligonucleotide sequences, wherein at least one of B1, B2, and B3 are present in each synthetic nucleotide molecule contained in said additional set of synthetic nucleotide molecules.

19. The method of claim 15, wherein the random oligonucleotide sequence comprises at least 4 and not more than 15 nucleotides.

20. The method of claim 19, wherein the random oligonucleotide sequence comprises 8 nucleotides.

21. The method of any one of claims 1-4, wherein the first adaptor sequence comprises a molecular tag.

22. The method of claim 21, wherein the molecular tag is a mosaic tag.

* * * * *

UNITED STATES PATENT AND TRADEMARK OFFICE
CERTIFICATE OF CORRECTION

PATENT NO. : 11,254,980 B1
APPLICATION NO. : 16/197629
DATED : February 22, 2022
INVENTOR(S) : Ryan O. Emerson et al.

It is certified that error appears in the above-identified patent and that said Letters Patent is hereby corrected as shown below:

In the Specification

In Column 28, Line 1, "FIGS. 1A and 1$i$," should read --FIGS. 1A and 1B,--.

Signed and Sealed this
Twenty-sixth Day of April, 2022

Katherine Kelly Vidal
*Director of the United States Patent and Trademark Office*